(12) United States Patent
Mortimer et al.

(10) Patent No.: US 11,643,694 B2
(45) Date of Patent: May 9, 2023

(54) METHODS FOR EARLY DETECTION OF CANCER

(71) Applicant: GUARDANT HEALTH, INC., Redwood City, CA (US)

(72) Inventors: Stefanie Ann Ward Mortimer, Morgan Hill, CA (US); AmirAli Talasaz, Atherton, CA (US); Darya Chudova, San Jose, CA (US); Helmy Eltoukhy, Atherton, CA (US)

(73) Assignee: GUARDANT HEALTH, INC., Palo Alto, CA (US)

( * ) Notice: Subject to any disclaimer, the term of this patent is extended or adjusted under 35 U.S.C. 154(b) by 0 days.

(21) Appl. No.: 17/688,762

(22) Filed: Mar. 7, 2022

(65) Prior Publication Data

US 2022/0186323 A1 Jun. 16, 2022

Related U.S. Application Data

(63) Continuation of application No. 17/507,109, filed on Oct. 21, 2021, which is a continuation of application No. 17/367,245, filed on Jul. 2, 2021, which is a continuation of application No. 16/093,916, filed as application No. PCT/US2017/027809 on Apr. 14, 2017, now abandoned.

(60) Provisional application No. 62/324,287, filed on Apr. 18, 2016, provisional application No. 62/322,784, filed on Apr. 14, 2016, provisional application No. 62/322,786, filed on Apr. 14, 2016, provisional application No. 62/322,775, filed on Apr. 14, 2016, provisional application No. 62/322,783, filed on Apr. 14, 2016, provisional application No. 62/322,773, filed on Apr. 14, 2016.

(51) Int. Cl.

| | |
|---|---|
| C12Q 1/6886 | (2018.01) |
| G01N 33/574 | (2006.01) |
| G16B 30/10 | (2019.01) |
| G16B 20/20 | (2019.01) |
| C12Q 1/6806 | (2018.01) |
| C12Q 1/6869 | (2018.01) |
| C12M 1/34 | (2006.01) |
| C12M 1/00 | (2006.01) |
| G16H 50/30 | (2018.01) |
| G16H 50/20 | (2018.01) |

(52) U.S. Cl.
CPC ............ *C12Q 1/6886* (2013.01); *C12M 1/00* (2013.01); *C12M 1/34* (2013.01); *C12Q 1/6806* (2013.01); *C12Q 1/6869* (2013.01); *G01N 33/57407* (2013.01); *G16B 20/20* (2019.02); *G16B 30/10* (2019.02); *G16H 50/20* (2018.01); *G16H 50/30* (2018.01); *C12Q 2600/118* (2013.01); *C12Q 2600/154* (2013.01); *C12Q 2600/156* (2013.01); *C12Q 2600/166* (2013.01)

(58) Field of Classification Search
CPC .. C12Q 1/6886; C12Q 1/6806; C12Q 1/6869; C12Q 2600/118; C12Q 2600/154; C12Q 2600/156; C12Q 2600/166; C12M 1/00; C12M 1/34; G01N 33/57407; G16B 20/20; G16B 30/10; G16H 50/20; G16H 50/30

See application file for complete search history.

(56) References Cited

U.S. PATENT DOCUMENTS

| | | |
|---|---|---|
| 5,712,126 A | 1/1998 | Weissman et al. |
| 7,537,897 B2 | 5/2009 | Brenner et al. |
| 7,723,103 B2 | 5/2010 | Mead et al. |
| 7,803,929 B2 | 9/2010 | Melkonyan et al. |
| 8,420,319 B2 | 4/2013 | Mikawa |
| 8,603,749 B2 | 12/2013 | Gillevet |
| 8,741,606 B2 | 6/2014 | Casbon et al. |
| 8,835,358 B2 | 9/2014 | Fodor et al. |
| 8,999,634 B2 | 4/2015 | Sanders et al. |
| 9,018,365 B2 | 4/2015 | Brenner |
| 9,080,210 B2 | 7/2015 | Eijk et al. |
| 9,260,753 B2 | 2/2016 | Xie et al. |
| 9,404,156 B2 | 8/2016 | Hicks et al. |
| 9,745,627 B2 | 8/2017 | Eijk et al. |
| 9,752,188 B2 | 9/2017 | Schmitt et al. |
| 9,850,523 B1 | 12/2017 | Chudova et al. |
| 10,450,611 B2 | 10/2019 | West et al. |
| 10,577,650 B2 | 3/2020 | Zimmermann et al. |
| 10,597,717 B2 | 3/2020 | Maguire et al. |
| 11,345,968 B2 | 5/2022 | Mortimer et al. |
| 11,408,033 B2 | 8/2022 | Bartha et al. |

(Continued)

FOREIGN PATENT DOCUMENTS

| | | |
|---|---|---|
| EP | 3433373 B1 | 1/2022 |
| WO | 2000058516 A2 | 10/2000 |

(Continued)

OTHER PUBLICATIONS

Guardant360 NIH Genetic Testing Registry (GTR)—NCBI, (GTR Test ID GTR000527948.1 https://www.ncbi.nlm.nih.gov/gtr/tests/527948.1/methodology/, sections methodology, performance characteristics and Interpretation, pp. 1-4, Last Updated: Aug. 28, 2015.*

Clark, T.A. et al. "Analytical Validation of a Hybrid Capture Based Next-Generation Sequencing Clinical Assay for Genomic Profiling of Cell-Free Circulating Tumor DNA," J. Mol. Diagnostics (2018) 20(5):686-702.

Co-Pending U.S. Appl. No. 17/507,109, filed Oct. 21, 2021.

Extended European search report and opinion dated Nov. 12, 2019 for EP Application No. 17783335.7.

(Continued)

*Primary Examiner* — Cynthia B Wilder

(74) *Attorney, Agent, or Firm* — Timothy A. Hott

(57) ABSTRACT

Disclosed herein are methods for use in detection of single nucleotide variants (SNVs) or indels. The methods may comprise enriching cell-free DNA molecules for a panel of genomic regions and deep sequencing the enriched cfDNA to detect the SNVs or indels.

17 Claims, 27 Drawing Sheets

(56) References Cited

U.S. PATENT DOCUMENTS

| | | | |
|---|---|---|---|
| 2001/0014451 A1 | 8/2001 | Shultz et al. | |
| 2004/0209299 A1 | 10/2004 | Pinter et al. | |
| 2006/0073506 A1 | 4/2006 | Christians et al. | |
| 2007/0065844 A1 | 3/2007 | Golub et al. | |
| 2007/0172839 A1 | 7/2007 | Smith et al. | |
| 2008/0070792 A1* | 3/2008 | Stoughton | C12Q 1/6874 435/6.12 |
| 2009/0036323 A1 | 2/2009 | Eijk et al. | |
| 2009/0105959 A1 | 4/2009 | Braverman et al. | |
| 2009/0298075 A1 | 12/2009 | Travers et al. | |
| 2010/0323348 A1 | 12/2010 | Hamady et al. | |
| 2011/0319299 A1 | 12/2011 | Osborne et al. | |
| 2012/0316074 A1 | 12/2012 | Saxonov | |
| 2013/0005585 A1 | 1/2013 | Anderson et al. | |
| 2013/0017549 A1 | 1/2013 | Hong | |
| 2014/0100121 A1 | 4/2014 | Lo et al. | |
| 2015/0024950 A1 | 1/2015 | Bielas et al. | |
| 2015/0087557 A1 | 3/2015 | Lubiene et al. | |
| 2016/0017419 A1 | 1/2016 | Chiu et al. | |
| 2016/0024576 A1 | 1/2016 | Chee | |
| 2016/0026758 A1 | 1/2016 | Jabara et al. | |
| 2016/0032396 A1* | 2/2016 | Diehn | C12Q 1/6827 506/26 |
| 2016/0046986 A1 | 2/2016 | Eltoukhy et al. | |
| 2016/0053301 A1 | 2/2016 | Raymond et al. | |
| 2016/0060691 A1 | 3/2016 | Giresi et al. | |
| 2016/0130649 A1 | 5/2016 | Xie et al. | |
| 2016/0319345 A1 | 11/2016 | Gnerre et al. | |
| 2017/0051347 A1 | 2/2017 | Vogelstein et al. | |
| 2017/0058332 A1 | 3/2017 | Kermani et al. | |
| 2017/0107576 A1 | 4/2017 | Babiarz et al. | |
| 2018/0179578 A1 | 6/2018 | Raymond et al. | |
| 2018/0251848 A1 | 9/2018 | Diehn et al. | |
| 2019/0085406 A1 | 3/2019 | Mortimer et al. | |
| 2020/0165678 A1 | 5/2020 | Mitchell et al. | |
| 2022/0025469 A1 | 1/2022 | Mortimer et al. | |

FOREIGN PATENT DOCUMENTS

| | | |
|---|---|---|
| WO | 2012129363 A2 | 9/2012 |
| WO | 2013019075 A2 | 2/2013 |
| WO | 2014039556 A1 | 3/2014 |
| WO | 2014113204 A1 | 7/2014 |
| WO | 2014149134 A2 | 9/2014 |
| WO | 2014151117 A1 | 9/2014 |
| WO | 2014182521 A1 | 11/2014 |
| WO | 2015100427 A1 | 7/2015 |
| WO | 2015159293 A2 | 10/2015 |
| WO | 2015175705 A1 | 11/2015 |
| WO | 2015164432 | 12/2015 |
| WO | 2016019360 A1 | 2/2016 |
| WO | 2016040901 A1 | 3/2016 |
| WO | 2016179049 A1 | 11/2016 |
| WO | 2017062867 A1 | 4/2017 |
| WO | 2017100441 A1 | 6/2017 |
| WO | 2017165463 A1 | 9/2017 |
| WO | 2017181146 A1 | 10/2017 |
| WO | 2017181202 A2 | 10/2017 |
| WO | 2017205823 A1 | 11/2017 |
| WO | 2018064629 A1 | 4/2018 |
| WO | 2019200228 A1 | 10/2019 |

OTHER PUBLICATIONS

Final Office Action in U.S. Appl. No. 17/507,109, dated Feb. 28, 2022.
Hamady, et al. Error-correcting barcoded primers for pyrosequencing hundreds of samples in multiplex. Nat Methods. Mar. 2008;5(3):235-7. doi: 10.1038/nmeth.1184. Epub Feb. 10, 2008.
Hensel, et al. Simultaneous identification of bacterial virulence genes by negative selection. Science. Jul. 21, 1995;269(5222):400-3.
Hiatt, et al. Single molecule molecular inversion probes for targeted, high-accuracy detection of low-frequency variation. Genome Res. May 2013;23(5):843-54. doi: 10.1101/gr.147686.112. Epub Feb. 4, 2013.
International search report and written opinion dated Sep. 13, 2017 for PCT/US2017/027809.
Kinde, et al. Detection and quantification of rare mutations with massively parallel sequencing. Proc Natl Acad Sci U S A. Jun. 7, 2011;108(23):9530-5. doi: 10.1073/pnas.1105422108. Epub May 17, 2011.
Kinde, et al. Supplemental Information, Detection and quantification of rare mutations with massively parallel sequencing. Proc Natl Acad Sci U S A. Jun. 7, 2011;108(23):1-10.
Lanman, et al., Analytical and Clinical Validation of a Digital Sequencing Panel for Quantitative, Highly Accurate Evaluation of Cell-Free Circulating Tumor DNA PLoS One, Oct. 2015, 10(10), e0140712. doi:10.1371/journal.pone.0140712.
Lizardi, et al. Mutation detection and single-molecule counting using isothermal rolling-circle amplification. Nat Genet. Jul. 1998;19(3):225-32.
Lodes, M.J. "Chimera-Free Library Prep for NGS Platforms" GenEngNews (2012) https://www.genengnews.com/magazine/173/chimera-free-library-prep-for-ngs-platforms/.
Lodes, M.J. et al. "Novel Chimera-Free, High Efficiency Library Preparation for NGS Platforms" Lucigen Corporation—Scientific Poster Sep. 16, 2011, http://www.lucigen.com/docs/posters/Chimera-Free-NGS-Libraries-Poster_091611.pdf.
Makrigiorgos, et al., A PCR-Based amplification method retaining quantative difference between two complex genomes. Nature Biotech, vol. 20, No. 9, pp. 936-939 (Sep. 2002).
Newman, et al. An ultrasensitive method for quantitating circulating tumor DNA with broad patient coverage. Nat Med. May 2014;20(5):548-54. doi: 10.1038/nm.3519. Epub Apr. 6, 2014.
Ng, S.B. et al. "Individualised multiplexed circulating tumour DNA assays for monitoring of tumour presence in patients after colorectal cancer surgery." Sci. Rep. 7, 40737; doi: 10.1038/ srep40737 (2017).
Office Action in U.S. Appl. No. 16/093,916, dated Jul. 28, 2021.
Office Action in U.S. Appl. No. 17/507,109, dated Dec. 8, 2021.
Office Action in U.S. Appl. No. 17/367,245, dated Oct. 14, 2021.
Ohtsubo et al. "Efficient N-tailing of blunt DNA ends by Moloney murine leukemia virus reverse transcriptase" Scientific Reports (Feb. 2, 2017) 7:41769 (pp. 1-10).
Paweletz, C.P. et al. "Bias-corrected targeted next-generation sequencing for rapid, multiplexed detection of actionable alterations in cell-free DNA from advanced lung cancer patients" Clin Cane Res (2016) 22(4):915-922.
Phallen, J. et al. "Direct detection of early-stage cancers using circulating tumor DNA" Sci Trans Med (2017) vol. 9, Issue 403, eaan2415DOI: 10.1126/scitranslmed.aan2415.
Schmitt et al. Supplemental Information http://www.pnas.org/content/suppl/2012/08/01/1208715109.DCSupplemental (2012).
Schmitt, et al. Detection of ultra-rare mutations by next-generation sequencing. Proc Natl Acad Sci U S A. Sep. 4, 2012;109(36):14508-13. doi: 10.1073/pnas.1208715109. Epub Aug. 1, 2012.
Shiroguchi, et al. Digital RNA sequencing minimizes sequence-dependent bias and amplification noise with optimized single-molecule barcodes. Proc Natl Acad Sci U S A. Jan. 24, 2012;109(4):1347-52. doi: 10.1073/pnas.1118018109. Epub Jan. 9, 2012.
Zhang, et al. The impact of next-generation sequencing on genomics. J Genet Genomics. Mar. 20, 2011;38(3):95-109. doi: 10.1016/j.jgg.2011.02.003. Epub Mar. 15, 2011.
Zill, O.A. et al. "Cell-Free DNA Next-Generation Sequencing in Pancreatobiliary Carcinomas" Cancer Discovery (2015) 5(10):1040-1048.
Office Action for U.S. Appl. No. 18/047,979, dated Jan. 19, 2023.
Office Action in U.S. Appl. No. 17/837,375, dated Sep. 9, 2022.

* cited by examiner

| Patient | Stage | Gene | Mutation | MAF (%) Pre-op | Intra-op / Follow-up | Tumor |
|---|---|---|---|---|---|---|
| SMC2016_1 | II | KRAS | G13D | - | 0.06 | 19.55 |
| SMC2016_2 | II | APC | P183T | 0.07 | - | - |
| | | KRAS | G12V | - | - | 25.07 |
| | | TP53 | C141Y | - | - | 41.30 |
| SMC2016_3 | II | APC | T252T | - | 0.03 | - |
| | | APC | R1589H | - | 0.07 | - |
| | | KRAS | G12V | 0.12 | 0.19 | 17.10 |
| | | TP53 | Y126C | - | 0.14 | 25.13 |
| SMC2016_4 | II | NRAS | Y4Y | 0.06 | - | - |
| | | TP53 | P278S | 0.03 | - | 61.69 |
| SMC2016_5 | II | APC | R1386* | - | - | 18.78 |
| | | TP53 | P152L | - | - | 34.80 |
| SMC2016_6 | II | APC | K523* | - | - | 29.66 |
| | | APC | R1589H | - | 0.11 | - |
| | | KRAS | G12D | - | - | 16.00 |
| | | TP53 | L252P | 0.04 | - | 22.50 |
| A0097 | III | APC | Q1378* | 2.86 | 0.17 | 61.8 |
| | | TP53 | R213* | 3.47 | 0.20 | 59.4 |
| A0098 | III | APC | F1396F | 0.3 | - | 47.6 |
| | | KRAS | G12V | 0.5 | - | 47.3 |
| | | APC | R283* | 0.2 | - | 23.6 |
| A0101 | II | TP53 | W91* | 0.07 | - | 56.2 |
| A0102 | IV | TP53 | I195T | - | 0.03 | - |
| | | KRAS | G12V | 0.27 | 0.07 | 29.7 |
| | | TP53 | H214R | - | 0.09 | - |
| A0105 | II | KRAS | G12D | - | - | 30.4 |
| | | APC | R2525H | - | 0.03 | - |
| | | APC | R1640Q | 0.08 | - | - |
| | | TP53 | R273C | 0.14 | - | 64.4 |

FIG. 5A

|  |  |  |  | MAF (%) | | |
|---|---|---|---|---|---|---|
| A0106 | II | APC | R2204Q | 0.04 | - | - |
|  |  | TP53 | R181C | 0.28 | 0.23 | - |
|  |  | KRAS | G12V | - | - | 13.2 |
|  |  | TP53 | H214R | 0.28 | 0.04 | 22.8 |
|  |  | APC | S1356* | 0.29 | - | 23.7 |
| A111 | unknown | NRAS | E76K | - | 0.03 | N/A |
|  |  | TP53 | R158H | 0.38 | 0.40 |  |
| 1 SMC | II | APC | E1306* | 0.4 | - | N/A |
|  |  | TP53 | G245S | 0.5 | - |  |
|  |  | KRAS | D173D | 2.1 | - |  |
| 2 SMC | II | TP53 | R273H | 0.07 | - | N/A |
| 3 SMC | II | KRAS | G12D | 0.2 | - | N/A |
|  |  | TP53 | G245D | 0.4 | 0.3 |  |
|  |  | TP53 | C242Y | 0.6 | 0.8 |  |
| 4 SMC | II | APC | E1397* | 0.2 | - | N/A |
|  |  | APC | R213* | 0.3 | - |  |
|  |  | TP53 | H179R | 1.1 | - |  |
| 6 SMC | II | TP53 | R282Q | 0.49 | - | N/A |
|  |  | TP53 | T125M | 0.34 | - |  |
| 7 SMC | II | APC | S2586D | 0.17 | 0.15 | N/A |
| 8 SMC | II | KRAS | G12D | 0.25 | - | N/A |

FIG. 5B

| % of patients with driver mutation detected | | |
|---|---|---|
|  | overall | stage II only |
| pre-op | 75% | 67% |
| intra-op | 50% | 33% |
| follow-up | 38% | 31% |

FIG. 6

| pre-op/tumor concordance | | |
|---|---|---|
|  | Overall | stage II only |
| sensitivity | 57% | 41% |
| specificity | 99.997% | 99.995% |
| accuracy | 99.990% | 99.986% |

FIG. 7

| Total Plasma (mL) | | cfDNA Yield (ng/mL) | | Library Input (ng) | |
|---|---|---|---|---|---|
| Pre | Intra-op / Follow-up | Pre | Intra-op / Follow-up | Pre | Intra-op / Follow-up |
| 4.9 | 4.4 | 10 | 24 | 40 | 100 |

FIG. 8

SNVs

| AKT1 | ALK | APC | ATM | BRAF |
|---|---|---|---|---|
| CTNNB1 | EGFR | ERBB2 | ESR1 | FGFR2 |
| GATA3 | GNAS | IDH1 | IDH2 | KIT |
| KRAS | MET | NRAS | PDGFRA | PIK3CA |
| PTEN | RB1 | SMAD4 | STK11 | TP53 |

Indels

| APC | EGFR | ERBB2 | GATA3 |
|---|---|---|---|
| MET | STK11 | TP53 | |

Fusions

| ALK |
|---|

FIG. 15

| Domain | Exon | SNVs |
|---|---|---|
| Extracellular | 8 | G309R, S310F/Y |
| Transmembrane | | |
| Juxtamembrane | | |
| Tyrosine kinase | 19 | L755P/S/V, E757K/Q, I767M, D769Y |
| | 20 | G776I/V, V777L |
| | 21 | V842I |
| | 22 | E930D |
| C-Terminal | | |

FIG. 20

METHODS FOR EARLY DETECTION OF CANCER

CROSS-REFERENCE

This application is a continuation of U.S. application Ser. No. 17/507,109, filed Oct. 21, 2021, which is a continuation of U.S. application Ser. No. 17/367,245, filed Jul. 2, 2021, which is a continuation of U.S. application Ser. No. 16/093,916, filed Oct. 15, 2018 (now abandoned), which is a National Stage Entry of International Application No. PCT/US2017/027809, filed Apr. 14, 2017, which claims the benefit of U.S. Provisional Application No. 62/322,773, filed Apr. 14, 2016, U.S. Provisional Application No. 62/322,775, filed Apr. 14, 2016, U.S. Provisional Application No. 62/322,783, filed Apr. 14, 2016, U.S. Provisional Application No. 62/322,784, filed Apr. 14, 2016, U.S. Provisional Application No. 62/322,786, filed Apr. 14, 2016, and U.S. Provisional Application No. 62/324,287, filed Apr. 18, 2016, each of which is incorporated by reference in its entirety.

BACKGROUND

Cancer is a major cause of disease worldwide. Each year, tens of millions of people are diagnosed with cancer around the world, and more than half of the patients eventually die from it. In many countries, cancer ranks the second most common cause of death following cardiovascular diseases. Early detection is associated with improved outcomes for many cancers.

To detect cancer, several screening tests are available. A physical exam and history survey general signs of health, including checking for signs of disease, such as lumps or other unusual physical symptoms. A history of a patient's health habits and past illnesses and treatments will also be taken. Laboratory tests are another type of screening test and may include medical procedures to procure samples of tissue, blood, urine, or other substances in the body before conducting laboratory testing. Imaging procedures screen for cancer by generating visual representations of areas inside the body. Genetic tests detect certain gene deleterious mutations linked to some types of cancer. Genetic testing is particularly useful for a number of diagnostic methods.

SUMMARY

The present disclosure provides methods and systems that may be used for early cancer detection. Such methods may provide for high sensitivity detection of one or more genetic variants.

In an aspect, a method comprises (a) providing a sample comprising cfDNA from a subject, wherein the subject does not detectably exhibit a cancer; (b) capturing from the sample cfDNA molecules covered by a sequencing panel, wherein the sequencing panel comprises one or more regions from each of a plurality of different genes, wherein: (i) the sequencing panel is no greater than 50,000 nucleotides; (ii) the presence of a tumor marker in any one of the different genes indicates that the subject has the cancer; and (iii) at least 80% of subjects having the cancer have a tumor marker present in at least one of the plurality of different genes; and (c) sequencing the captured cfDNA molecules to a read depth sufficient to detect the tumor markers at a frequency in the sample as low as 0.01%.

In some embodiments, the cfDNA is derived from blood, serum or plasma. In some embodiments, the sample comprises between 10 nanograms and 300 nanograms cfDNA. In some embodiments, the cancer is selected from the group consisting of ovarian cancer, pancreatic cancer, breast cancer, colorectal cancer, and non-small cell lung carcinoma. In some embodiments, the cancer is non-small cell lung carcinoma, and the non-small cell lung carcinoma is squamous cell carcinoma or adenocarcinoma.

In some embodiments, the subject does not detectably exhibit the cancer as shown by one or more imaging methods selected from the group consisting of positron emission tomography scan, magnetic resonance imaging, X-ray, computerized axial tomography scan, and ultrasound. In some embodiments, the subject has previously undergone treatment for the cancer.

In some embodiments, enriching comprises sequence capture of cfDNA molecules covered by the panel. In some embodiments, the plurality of genes is between 2 to 30 different genes. In some embodiments, the plurality of genes is no more than any of 10, 9, 8, 7, 6, or 5 different genes. In some embodiments, the panel comprises a plurality of genes selected from the group consisting of AKT1, ALK, APC, ATM, BRAF, CTNNB1, EGFR, ERBB2, ESR1, FGFR2, GATA3, GNAS, IDH1, IDH2, KIT, KRAS, MET, NRAS, PDGFRA, PIK3CA, PTEN, RB1, SMAD4, STK11, and TP53. In some embodiments, the panel comprises a plurality of genes selected from the group consisting of ABL1, AKT1, ALK, APC, AR, ATM, BRAF, CDH1, CDKN2A, CSF1R, CTBBB1, EGFR, ERBB2, ERBB4, EZH2m, FBXW7, FGFR1, FGFR2, FGFR3, FLT3, GNA11, GNAQ, GNAS, HNF1A, HRAS, IDH1, IDH2, JAK2, JAK3, KDR, KIT, KRAS, MET, MLH1, MPL, MYC, NOTCH1, NPM1, NRAS, PDGFRA, PIK3CA, PTPN11, PTEN, PROC, RB1, RET, SMAD4, SMARCB1, SMO, SRC, STK11, TERT, TP53, and VHL. In some embodiments, the sequencing panel is about 15,000 nucleotides to about 30,000 nucleotides.

In some embodiments, a tumor marker is selected from the group consisting of a single base substitution, a copy number variation, an indel, a gene fusion, a transversion, a translocation, an inversion, a deletion, aneuploidy, partial aneuploidy, polyploidy, chromosomal instability, chromosomal structure alterations, chromosome fusions, a gene truncation, a gene amplification, a gene duplication, a chromosomal lesion, a DNA lesion, abnormal changes in nucleic acid chemical modifications, abnormal changes in epigenetic patterns and abnormal changes in nucleic acid methylation.

In some embodiments, at least 85%, at least 90%, at least 93%, at least 95%, at least 97%, at least 98% or at least 99% of subjects having the cancer have a tumor marker present in at least one of the plurality of different genes.

Some embodiments comprise sequencing the captured cfDNA molecules to a read depth sufficient to detect the tumor markers at a frequency in the sample as low as 0.005%, 0.001% or 0.0005%.

In some embodiments, the one or more regions are selected for the panel to detect one or more differentially methylated regions. In some embodiments, the one or more regions comprise sequences differentially transcribed across one or more tissues of the subject. In some embodiments, the panel is selected to detect the one or more tumor markers with a theoretical sensitivity of 85% or greater. In some embodiments, the panel is selected to achieve a sensitivity of 85% or greater for one or more cancers selected from the group consisting of colorectal cancer, ovarian cancer, lung cancer, and pancreatic cancer.

In some embodiments, assaying the cell-free nucleic acid molecules comprises subjecting the cell-free nucleic acid molecules to sequencing in the one or more regions in the panel to generate sequence reads.

In some embodiments, sequencing is performed at a read depth of at least 1000, at least 5000 at least 10,000, at least 20,000, at least 30,000, at least 50,000, at least 75,000, at least 100,000 unique reads per base. In some embodiments, subjecting to sequencing comprises sequencing from about 1.2 billion to about 6.5 billion base pairs.

In some embodiments, one or more of the cell-free nucleic acid molecules are isolated from one or more exosomes in the biological sample. In some embodiments, one or more of the cell-free nucleic acid molecules are isolated from one or more cell surface bound nucleic acids.

In some embodiments, the cell-free nucleic acid molecules comprise RNA. In some embodiments, the cell-free nucleic acid molecules comprise DNA. In some embodiments, the cell-free nucleic acid molecules comprise methylated DNA.

In some embodiments comprise selecting the panel based on nucleosome binding patterns. In some embodiments, a nucleosome binding pattern is determined based on size or number of cfNA (e.g., cfDNA) fragments, for example, mapping to particular genomic regions.

In some embodiments, one or more regions comprise one or more sequences selected from the group consisting of exons, introns, promoters, 3' untranslated regions, 5' untranslated regions, and splice sites. In some embodiments, the one or more tumor markers is detected at a sensitivity of about 80% or greater. In some embodiments, the one or more tumor markers is detected at a specificity of about 95% or greater. In some embodiments, the one or more tumor markers is detected at a sensitivity of about 80% or greater and a specificity of about 95% or greater. In some embodiments, the one or more tumor markers is detected at an accuracy of about 95% or greater.

In an aspect, disclosed herein is a method comprising: a. providing a sample comprising cell-free nucleic acid (cfNA) molecules from a subject, wherein the subject does not detectably exhibit a cancer; b. capturing from the sample cfNA molecules covered by a sequencing panel, wherein the sequencing panel comprises one or more regions from each of a plurality of different genes, wherein: i. the sequencing panel is no greater than 50,000 nucleotides; ii. a presence of a tumor marker in any one of the different genes indicates that the subject has the cancer; and iii. at least 80% of subjects having the cancer have a tumor marker present in at least one of the plurality of different genes; and c. sequencing the captured cfNA molecules to a read depth sufficient to detect the tumor markers at a frequency in the sample as low as 1.0%, 0.75%, 0.5%, 0.25%, 0.1%, 0.075%, 0.05%, 0.025%, 0.01%, or 0.005%.

In some embodiments, the cfNA molecules are derived from blood, serum, or plasma. In some embodiments, the sample comprises between 10 nanograms and 300 nanograms of cfNA, and wherein the cfNA is circulating cell-free DNA (cfDNA).

In some embodiments, the cancer is selected from the group consisting of ovarian cancer, pancreatic cancer, breast cancer, colorectal cancer, and non-small cell lung carcinoma (NSCLC), or a combination thereof. In some embodiments, the cancer is non-small cell lung carcinoma (NSCLC), and the non-small cell lung carcinoma (NSCLC) is squamous cell carcinoma or adenocarcinoma. In some embodiments, the subject does not detectably exhibit the cancer as shown by one or more imaging methods selected from the group consisting of positron emission tomography scan, magnetic resonance imaging, X-ray, computerized axial tomography scan, and ultrasound. In some embodiments, the subject has previously undergone treatment for the cancer. In some embodiments, enriching comprises sequence capture of cfNA molecules covered by the panel.

In some embodiments, the plurality of genes is between 2 to 30 different genes. In some embodiments, the plurality of genes is no more than any of 10, 9, 8, 7, 6, or 5 different genes. In some embodiments, the panel comprises a plurality of genes selected from the group consisting of AKT1, ALK, APC, ATM, BRAF, CTNNB1, EGFR, ERBB2, ESR1, FGFR2, GATA3, GNAS, IDH1, IDH2, KIT, KRAS, MET, NRAS, PDGFRA, PIK3CA, PTEN, RB1, SMAD4, STK11, and TP53. In some embodiments, the sequencing panel is about 15,000 nucleotides to about 30,000 nucleotides.

In some embodiments, the tumor marker is selected from the group consisting of a single base substitution, an insertion or deletion (indel), a gene fusion, a transversion, a translocation, an inversion, a deletion, aneuploidy, partial aneuploidy, polyploidy, chromosomal instability, chromosomal structure alterations, chromosome fusions, a gene truncation, a gene amplification, a gene duplication, a chromosomal lesion, a DNA lesion, abnormal changes in nucleic acid chemical modifications, abnormal changes in epigenetic patterns and abnormal changes in nucleic acid methylation.

In some embodiments, at least 85%, at least 90%, at least 93%, at least 95%, at least 97%, at least 98%, or at least 99% of subjects having the cancer have a tumor marker present in at least one of the plurality of different genes. In some embodiments, the method comprises sequencing the captured cfNA molecules to a read depth sufficient to detect the tumor markers at a frequency in the sample as low as 0.005%, 0.001%, or 0.0005%.

In some embodiments, the one or more regions are selected for the sequencing panel to detect one or more differentially methylated regions. In some embodiments, the one or more regions comprise sequences differentially transcribed across one or more tissues of the subject. In some embodiments, the sequencing panel is selected to detect the one or more tumor markers with a theoretical sensitivity of 85% or greater. In some embodiments, the panel is selected to achieve a sensitivity of 85% or greater for one or more cancers selected from the group consisting of colorectal cancer, ovarian cancer, lung cancer, and pancreatic cancer.

In some embodiments, assaying the cfNA molecules comprises subjecting the cfNA molecules to sequencing in the one or more regions in the sequencing panel to generate sequence reads. In some embodiments, sequencing is performed at a read depth of at least 1000, at least 5000, at least 10,000, at least 20,000, at least 30,000, at least 50,000, at least 75,000, or at least 100,000 unique reads per base. In some embodiments, the subjecting to sequencing comprises sequencing from about 1.2 billion to about 6.5 billion nucleotides.

In some embodiments, one or more of the cfNA molecules are isolated from one or more exosomes in the biological sample. In some embodiments, one or more of the cfNA molecules are isolated from one or more cell surface bound nucleic acids. In some embodiments, the cfNA molecules comprise RNA. In some embodiments, the cfNA molecules comprise DNA. In some embodiments, the cfNA molecules comprise methylated DNA.

In some embodiments, the method further comprises selecting the panel based on nucleosome binding patterns. In some embodiments, the one or more regions comprise one or more sequences selected from the group consisting of exons, introns, promoters, 3' untranslated regions, 5' untranslated regions, and splice sites.

In some embodiments, the cancer is detected at a sensitivity of about 80% or greater. In some embodiments, the cancer is detected at a specificity of about 95% or greater. In some embodiments, the cancer is detected at a sensitivity of about 80% or greater and a specificity of about 95% or greater. In some embodiments, the cancer is detected at an accuracy of about 95% or greater.

In some embodiments, the cfNA molecules are uniquely tagged with respect to one another. In some embodiments, the cfNA molecules are non-uniquely tagged with respect to one another. In some embodiments, the cfNA molecules are not tagged.

In another aspect, disclosed herein is a method for detecting cancer in a subject comprising: sequencing circulating cell-free DNA (cfDNA) from the subject at a depth of at least 50,000 reads per base to detect one or more genetic variants associated with cancer. In some embodiments, the sequencing is at a depth of at least 100,000 reads per base. In some embodiments, the sequencing is at a depth of about 120,000 reads per base. In some embodiments, the sequencing is at a depth of about 150,000 reads per base. In some embodiments, the sequencing is at a depth of about 200,000 reads per base.

In some embodiments, the reads per base represent at least 5,000 original nucleic acid molecules, at least 10,000 original nucleic acid molecules, at least 20,000 original nucleic acid molecules, at least 30,000 original nucleic acid molecules, at least 40,000 original nucleic acid molecules, or at least 50,000 original nucleic acid molecules.

In some embodiments, the one or more genetic variants associated with cancer are selected from the group consisting of an SNV, CNV, indel, fusion, or nucleosome binding pattern. In some embodiments, the SNV is detected in a gene selected from the group consisting of AKT1, ALK, APC, ATM, BRAF, CTNNB1, EGFR, ERBB2, ESR1, FGFR2, GATA3, GNAS, IDH1, IDH2, KIT, KRAS, MET, NRAS, PDGFRA, PIK3CA, PTEN, RB1, SMAD4, STK11, and TP53. In some embodiments, the nucleosome binding pattern is determined based on size or number of cfDNA fragments.

In some embodiments, the sequencing is performing on an enriched set of cfDNA molecules. In some embodiments, the enriched set of cfDNA molecules are representative of less than 60,000 bp across the human genome. In some embodiments, the enriched set of cfDNA molecules are representative of less than 35,000 bp across the human genome. In some embodiments, the enriched set of cfDNA molecules are representative of 10,000-30,000 bp across the human genome. In some embodiments, the enriched set of cfDNA molecules are representative of nucleosome regions associated with cancer. In some embodiments, the enriched set of cfDNA molecules comprises one or more genes selected from the group consisting of: AKT1, ALK, APC, ATM, BRAF, CTNNB1, EGFR, ERBB2, ASR1, FGFR2, GATA3, GNAS, IDH1, IDH2, KIT, KRAS, MET, NRAS, PDGFRA, PIK3CA, PTEN, RB1, RB1, SMAD4, STK11, and TP53. In some embodiments, the enriched set of cfDNA molecules comprises one or more enhancer sequences or promoter sequences. In some embodiments, the enriched set of cfDNA molecules comprises one or more genomic loci, and further wherein at least 80% of subjects having the cancer have a tumor marker present in at least one of the one or more genomic loci. In some embodiments, the cancer is colorectal cancer, ovarian cancer, lung cancer, pancreatic cancer, or liver cancer.

In some embodiments, the method further comprises comparing sequence information from the cfDNA to sequence information obtained from a cohort of healthy individuals, a cohort of cancer patients, or germline DNA from the subject. In some embodiments, the germline DNA from the subject is obtained from leukocytes from the subject. In some embodiments, the cohort of cancer patients has the same stage of cancer, the same type of cancer, or both. In some embodiments, the cohort of healthy individuals may be chosen for certain risk factors such as demographic risk factors or lifestyle risk factors (e.g., smoking).

In some embodiments, the method further comprises amplifying the cfDNA prior to sequencing, and determining a consensus sequence from sequence reads obtained from the sequencing to reduce errors from amplification or sequencing. In some embodiments, determining the consensus sequence is performed on a molecule-by-molecule basis. In some embodiments, determining the consensus sequence is performed on a base by base basis. In some embodiments, detection of consensus sequence is based on assessing probabilities of each of the potential nucleotides based on the observed sequencing output, as well as sequencing and amplification error profile characteristics of an individual sample, a batch of samples, or a reference set of samples. In some embodiments, determining the consensus sequence is performed using molecular barcodes that tag individual cfDNA molecules derived from the subject. In some embodiments, a set of molecules with a consensus sequence deviant from the human reference is compared to those observed in other samples processed in the laboratory to determine and exclude any potential contaminating event. In some embodiments, determining the consensus sequence is optimized by comparing the consensus sequence to those obtained from the cohort of healthy individuals, the cohort of cancer patients, or the germline DNA from the subject.

In some embodiments, the method further comprises tagging the cfDNA molecules with a barcode such that at least 20% of the cfDNA in a sample derived from the subject are tagged. In some embodiments, the tagging is performed by attaching adaptors comprising a barcode. In some embodiments, the adaptors comprise any or all of blunt end adaptors, restriction enzyme overhang adaptors, or adaptors with a single nucleotide overhang. In some embodiments, the adaptors with a single nucleotide overhang comprise C-tail adaptors, A-tail adaptors, T-tail adaptors, and/or G-tail adaptors. In some embodiments, the tagging is performed by PCR amplification using primers with barcodes. In some embodiments, the barcode is single stranded. In some embodiments, the barcode is double stranded.

In some embodiments, the method further comprises dividing the cfDNA into partitions. In some embodiments, the cfDNA in each partition is uniquely tagged with respect to each other partition. In some embodiments, the cfDNA in each partition is non-uniquely tagged with respect to each other partition. In some embodiments, the cfDNA in each partition is not tagged.

In some embodiments, at least 10 ng of cfDNA is obtained from the subject. In some embodiments, at least 200 or 300 ng or cfDNA is obtained from the subject. In some embodiments, the cfDNA comprises at least 4000, at least 5000, at least 7,000, at least 10,000, or at least 15,000 unique molecules for every base to be sequenced or analyzed.

In some embodiments, the method further comprises obtaining a sample of at least 10 mL of blood or plasma from the subject. In some embodiments, the method further comprises performing epigenomic or nucleosomal profiling analysis of the cfDNA. In some embodiments, the method further comprises determining a tissue of origin of the cfDNA.

In some embodiments, the method further comprises performing circular sequencing on the cfDNA or amplification products thereof. In some embodiments, the method further comprises batching cfDNA from two or more different subjects into a single sequencing instruments at a ratio based on the amount of cfDNA obtained from each of the different subjects.

In another aspect, disclosed herein is a method for detecting a tumor in a subject suspected of having cancer or having cancer, comprising: (a) sequencing cell-free DNA (cfDNA) molecules derived from a cell-free DNA (cfDNA) sample obtained from the subject; (b) analyzing sequence reads derived from the sequencing to identify (i) circulating tumor DNA (ctDNA) among the cfDNA molecules and (ii) one or more driver mutations in the ctDNA; and (c) using information about the presence, absence, or amount of the one or more driver mutations in the ctDNA molecules to identify (i) the tumor in the subject and (ii) actions for treatment of the tumor to be taken by the subject, wherein the method detects the tumor in the subject with a sensitivity of at least 85%, a specificity of at least 99%, and a diagnostic accuracy of at least 99%.

In some embodiments, the cfDNA sample is derived from a blood sample obtained from the subject.

In some embodiments, the one or more driver mutations comprises a somatic variant detected at a mutant allele frequency (MAF) of no more than 0.05%. In some embodiments, the one or more driver mutations comprises a fusion detected at a mutant allele frequency (MAF) of no more than 0.1%. In some embodiments, the one or more driver mutations comprises a driver mutation present in EGFR, KRAS, MET, BRAF, RET, ALK, ERBB2, or ROS1.

In some embodiments, the method further comprises detecting mutation distributions for each of one or more driver mutations, wherein the mutation distribution for each of the one or more driver mutations is detected with a correlation of at least 0.99 to a mutation distribution of the driver mutation detected in a cohort of the subject by tissue genotyping. In some embodiments, the one or more driver mutations comprises a KRAS mutation. In some embodiments, the one or more driver mutations comprises a PIK3CA mutation.

In another aspect, disclosed herein is a method for identifying treatment for a subject with non-small cell lung carcinoma (NSCLC), comprising: (a) sequencing cell-free DNA (cfDNA) molecules derived from a cell-free DNA (cfDNA) sample obtained from the subject; (b) analyzing sequence reads derived from the sequencing to identify (i) circulating tumor DNA (ctDNA) among the cfDNA molecules and (ii) a copy number amplification (CNA) of the MET gene in the ctDNA with a specificity of at least 99%; and (c) identifying, based at least on the identified CNA of the MET gene, an anti-MET therapy to be administered to the subject to treat the NSCLC.

In some embodiments, the cfDNA sample is derived from a blood sample obtained from the subject.

In some embodiments, the NSCLC comprises a stage III cancer.

In some embodiments, the subject was previously treated with an EGFR tyrosine kinase inhibitor (TKI) treatment prior to (a). In some embodiments, the subject was previously treated with chemotherapy, radiotherapy, or chemoradiotherapy prior to (a).

In some embodiments, the CNA comprises an amplification of at least about 20. In some embodiments, the CNA comprises an amplification of at least about 30. In some embodiments, the CNA comprises an amplification of at least about 40. In some embodiments, the CNA comprises an amplification of at least about 50.

In some embodiments, the CNA is identified with a sensitivity of at least 80%. In some embodiments, the CNA is identified with a specificity of at least 99.9%. In some embodiments, the CNA is identified with a specificity of at least 99.99%. In some embodiments, the CNA is identified with a specificity of at least 99.999%. In some embodiments, the CNA is identified with a specificity of at least 99.9999%.

In some embodiments, the method further comprises administering the anti-MET therapy to the subject to treat the NSCLC.

In another aspect, disclosed herein is a method for monitoring breast cancer in a subject, comprising: (a) sequencing cell-free DNA (cfDNA) molecules derived from a cell-free DNA (cfDNA) sample obtained from the subject; and (b) analyzing sequence reads derived from the sequencing to identify (i) circulating tumor DNA (ctDNA) among the cfDNA molecules and (ii) one or more mutations in the ctDNA from the subject selected from: EGFR, Exon 19 deletion; ERBB2, Exon 20 insertion; TP53, E286K mutation; AR, N706S mutation; ALK, G1137R mutation; MAP2K2, E66K mutation; and TP53, K164E mutation.

In some embodiments, the cfDNA sample is derived from a blood sample obtained from the subject.

In some embodiments, the breast cancer is metastatic breast cancer. In some embodiments, the metastatic breast cancer is treatment refractory.

In some embodiments, the subject was previously treated with a tyrosine kinase inhibitor (TKI) therapy prior to (a). In some embodiments, the subject was previously treated with chemotherapy, radiotherapy, or chemoradiotherapy prior to (a).

In some embodiments, the one or more mutations in the ctDNA from the subject are identified with a sensitivity of at least 80%. In some embodiments, the one or more mutations in the ctDNA from the subject are identified with a specificity of at least 99%. In some embodiments, the one or more mutations in the ctDNA from the subject are identified with a specificity of at least 99.9%. In some embodiments, the one or more mutations in the ctDNA from the subject are identified with a specificity of at least 99.99%. In some embodiments, the one or more mutations in the ctDNA from the subject are identified with a specificity of at least 99.999%. In some embodiments, the one or more mutations in the ctDNA from the subject are identified with a specificity of at least 99.9999%.

In some embodiments, the method further comprises identifying, based at least on the identified one or more mutations in the ctDNA from the subject, a treatment to be administered to the subject to treat the breast cancer. In some embodiments, the treatment comprises an anti-HER2 monoclonal antibody. In some embodiments, the treatment comprises a tyrosine kinase inhibitor (TKI) therapy. In some embodiments, the TKI therapy comprises a dual anti-EGFR/ERBB2 TKI therapy. In some embodiments, the method further comprises administering the treatment to the subject to treat the breast cancer.

In another aspect, disclosed herein is a method for identifying ERBB2 driver mutations in a subject with non-small cell lung cancer (NSCLC), the method comprising: (a) sequencing cell-free DNA (cfDNA) molecules derived from a cell-free DNA (cfDNA) sample obtained from the subject;

(b) analyzing sequence reads derived from the sequencing to identify (i) circulating tumor DNA (ctDNA) among the cfDNA molecules and (ii) the ERBB2 driver mutations in the ctDNA from the subject, wherein the ERBB2 driver mutations comprise one or more ERBB2 insertions or deletions (indels).

In some embodiments, the ERBB2 indels are selected from the group consisting of: p.Ala775 Gly776insTyrValMetAla (YVMA), p. Gly776delinsValCys, p.Pro780 Tyr781insGlySerPro, p.Ala775 Gly776insSerValMetAla, p.Ala775 Gly776insValAlaAla, p.Glu812 Arg814delinsGly, p. Gly776delinsLeuCys, p.Arg756 Glu757delinsLys, and p.Leu755 Glu757delinsProGln.

In some embodiments, the cfDNA sample is derived from a blood sample obtained from the subject.

In some embodiments, the NSCLC is immunohistochemistry (IHC) negative for HER2 overexpression.

In some embodiments, the subject was previously treated with a tyrosine kinase inhibitor (TKI) therapy prior to (a). In some embodiments, the subject was previously treated with chemotherapy, radiotherapy, or chemoradiotherapy prior to (a).

In some embodiments, the one or more ERBB2 indels in the ctDNA from the subject comprise a variant detected at a mutant allele frequency (MAF) of no more than 0.05%.

In some embodiments, the one or more ERBB2 indels in the ctDNA from the subject are identified with a sensitivity of at least 80%. In some embodiments, the one or more ERBB2 indels in the ctDNA from the subject are identified with a specificity of at least 99%. In some embodiments, the one or more ERBB2 indels in the ctDNA from the subject are identified with a specificity of at least 99.9%. In some embodiments, the one or more ERBB2 indels in the ctDNA from the subject are identified with a specificity of at least 99.99%.

In some embodiments, the method further comprises identifying, based at least on the one or more ERBB2 driver mutations in the ctDNA from the subject, a treatment to be administered to the subject to treat the NSCLC. In some embodiments, the method further comprises identifying a copy number amplification (CNA) of ERBB2 in the cfDNA sample.

In some embodiments, the method further comprises identifying one or more ERBB2 single nucleotide variants (SNVs) in the cfDNA sample. In some embodiments, the one or more ERBB2 SNVs are selected from the group consisting of: G309R, S310F/Y, L755P/S/V, E757K/Q, I767M, D769Y, G776I/V, V777L, V842I, and E930D.

In some embodiments, the method further comprises identifying, based at least on the identified one or more ERBB2 indels, a treatment to be administered to the subject. In some embodiments, the method further comprises administering the treatment to the subject to treat the NSCLC.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material. This application incorporates by reference International Patent Application No. PCT/US2013/058061, filed Sep. 4, 2013, International Application Patent No. PCT/US2014/ 072383, filed Dec. 24, 2014, International Patent Application No. PCT/US2014/000048, filed Mar. 15, 2014, U.S. patent application Ser. No. 15/254,363, filed Sep. 1, 2016, and U.S. patent application Ser. No. 15/426,668, filed Feb. 7, 2017.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings (also "fig." and "FIG." herein), of which:

FIGS. 5A and 5B show all reported SNVs from the study of example 1. SNVs with MAF >0.02% are reported. Dash indicates that the variant was not detected.

FIG. 6 shows detection rates using tumor next generation sequencing on cfDNA with surgically resected tumor as reference.

FIG. 7 shows concordance analysis for SNV results for pre-op blood draws using tumor NGS on surgically resected tumor as reference.

FIG. 8 shows key sample preparation values.

FIG. 9A depicts a Stage II CRC patient time course. FIG. 9B depicts a Stage II CRC patient time course. FIG. 9C depicts a Stage II CRC patient time course. FIG. 9D depicts a Stage IV CRC patient time course.

FIGS. 14A and 14B demonstrate successful removal of cancer tissue by surgery. FIGS. 14C and 14D show the evidence of molecular residual disease.

FIG. 15 shows genes selected for detection of major cancer types with >90% theoretical sensitivity. Bolded genes indicate genes with complete exon coverage.

FIG. 16A shows diversity across cfDNA input for analytical samples. FIG. 16B shows two genes with significant coverage improvements with assay optimization.

FIG. 20 depicts functional ERBB2 single nucleotide variants (SNVs).

DETAILED DESCRIPTION

Figure 1:
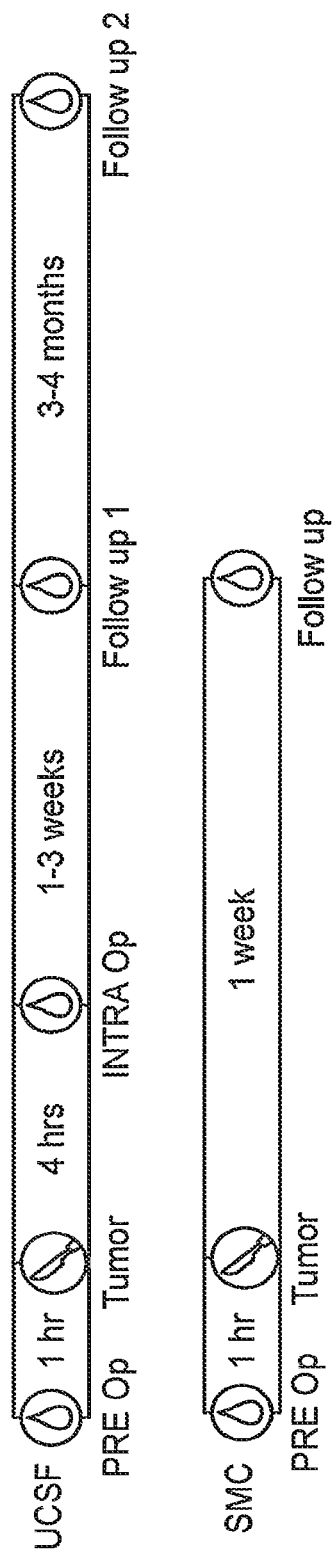
FIG. 1 depicts an example of the study design described herein. PRE Op: blood draw immediately before surgery; Tumor: Next-generation sequencing (NGS) on surgically resected tumor; INTRA Op: blood draw immediately after surgical resection of tumor; Follow up: blood draw >1 week after surgical resection of tumor.

While various embodiments of the disclosure have been shown and described herein, those skilled in the art will understand that such embodiments are provided by way of example only. Numerous variations, changes, and substitutions may occur to those skilled in the art without departing from the disclosure. It should be understood that various alternatives to the embodiments of the disclosure described herein may be employed.

The term "about" and its grammatical equivalents in relation to a reference numerical value can include a range of values up to plus or minus 10% from that value. For example, the amount "about 10" can include amounts from 9 to 11. The term "about" in relation to a reference numerical value can include a range of values plus or minus 10%, 9%, 8%, 7%, 6%, 5%, 4%, 3%, 2%, or 1% from that value.

The term "at least" and its grammatical equivalents in relation to a reference numerical value can include the reference numerical value and greater than that value. For example, the amount "at least 10" can include the value 10 and any numerical value above 10, such as 11, 100, and 1,000.

The term "at most" and its grammatical equivalents in relation to a reference numerical value can include the reference numerical value and less than that value. For example, the amount "at most 10" can include the value 10 and any numerical value under 10, such as 9, 8, 5, 1, 0.5, and 0.1.

As used herein the singular forms "a", "an", and "the" can include plural referents unless the context clearly dictates otherwise. Thus, for example, reference to "a cell" can include a plurality of such cells and reference to "the culture" can include reference to one or more cultures and equivalents thereof known to those skilled in the art, and so forth. All technical and scientific terms used herein can have the same meaning as commonly understood to one of ordinary skill in the art to which this disclosure belongs unless clearly indicated otherwise.

The term "subject," as used herein, generally refers to an animal, such as a mammalian species (e.g., human) or avian (e.g., bird) species, or other organism, such as a plant. More specifically, the subject can be a vertebrate, e.g., a mammal such as a mouse, a primate, a simian or a human. Animals include, but are not limited to, farm animals, sport animals, and pets. A subject can be a healthy individual, an individual that has or is suspected of having a disease or a predisposition to the disease, or an individual that is in need of therapy or suspected of needing therapy. A subject can be a patient.

The term "polynucleotide," as used herein, generally refers to a molecule comprising one or more nucleic acid subunits. A polynucleotide can include one or more subunits selected from adenosine (A), cytosine (C), guanine (G), thymine (T) and uracil (U), or variants thereof. A nucleotide can include A, C, G, T or U, or variants thereof. A nucleotide (nt) can include any subunit that can be incorporated into a growing nucleic acid strand. Such subunit can be an A, C, G, T, or U, or any other subunit that is specific to one or more complementary A, C, G, T or U, or complementary to a purine (i.e., A or G, or variant thereof) or a pyrimidine (i.e., C, T or U, or variant thereof). A subunit can enable individual nucleic acid bases or groups of bases (e.g., AA, TA, AT, GC, CG, CT, TC, GT, TG, AC, CA, or uracil-counterparts thereof) to be resolved. In some examples, a polynucleotide is deoxyribonucleic acid (DNA) or ribonucleic acid (RNA), or variants or derivatives thereof. A polynucleotide can be single-stranded or double-stranded.

The term "genome" generally refers to an entirety of an organism's hereditary information. A genome can be encoded either in DNA or in RNA. A genome can comprise coding regions that code for proteins as well as non-coding regions. A genome can include the sequence of all chromosomes together in an organism. For example, the human genome has a total of 46 chromosomes. The sequence of all of these together constitutes a human genome.

The terms "reference genome" and "reference sequence" as used herein, generally refers a sequence to which an analyzed sequence is compared. In some cases, a reference genome or reference sequence can be included with the population of cell-free polynucleotides to be analyzed. A reference genome may be, for example, a nucleic acid with a known sequence and a known quantity. A reference genome can be of the subject or another individual. A reference genome can be a digital construct, assembled to be representative of a species' set of genes, and stored on a database. The database can be internal or external. A reference genome can include the genome of any species of interest. Human genome sequences useful as references can include the hg19 assembly or any previous or available assembly. Such sequences can be interrogated using the genome browser available at genom.ucsc.edu/index.html. Other species genomes include, for example PanTro2 (chimp) and mm9 (mouse).

The term "genetic variant," as used herein, generally refers to an alteration, variant or polymorphism in a nucleic acid sample or genome of a subject. Such alteration, variant or polymorphism can be with respect to a reference genome, which may be a reference genome of the subject or other individual. Single nucleotide polymorphisms (SNPs) are a form of polymorphisms. In some examples, one or more polymorphisms comprise one or more single nucleotide variations (SNVs), insertions, deletions, repeats, small insertions, small deletions, small repeats, structural variant junctions, variable length tandem repeats, and/or flanking sequences. Copy number variants (CNVs), transversions and other rearrangements are also forms of genetic variation. A genomic alternation may be a base change, insertion, deletion, repeat, copy number variation, transversion, or a combination thereof.

The term "tumor marker", as used herein refers to a genetic variant associated with a cancer. A tumor marker and a cancer may be associated such that detection of a tumor marker is indicative of a subject having the cancer. A tumor marker may be indicative of a probability that a subject has a cancer. A tumor marker may be a cancer driver mutation. A cancer driver mutation may be a somatic mutation that causes, or "drives", cancer progression.

The terms "adaptor(s)", "adapter(s)" and "tag(s)" are used synonymously throughout this specification. An adaptor or tag can be coupled to a polynucleotide sequence to be "tagged" by any approach including ligation, hybridization, or other approaches.

The term "library adaptor" or "library adapter" as used herein, generally refers to a molecule (e.g., polynucleotide) whose identity (e.g., sequence) can be used to differentiate polynucleotides in a sample (e.g., a biological sample).

The term "sequencing adaptor," as used herein, generally refers to a molecule (e.g., polynucleotide) that is adapted to permit a sequencing instrument to sequence a target polynucleotide, such as by interacting with the target polynucleotide to enable sequencing. The sequencing adaptor permits the target polynucleotide to be sequenced by the sequencing instrument. In an example, the sequencing adaptor comprises a nucleotide sequence that hybridizes or binds to a capture polynucleotide attached to a solid support of a sequencing system, such as a flow cell. In another example, the sequencing adaptor comprises a nucleotide sequence that hybridizes or binds to a polynucleotide to generate a hairpin loop, which permits the target polynucleotide to be sequenced by a sequencing system. The sequencing adaptor can include a sequencer motif, which can be a nucleotide sequence that is complementary to a flow cell sequence of other molecule (e.g., polynucleotide) and usable by the sequencing system to sequence the target polynucleotide. The sequencer motif can also include a primer sequence for use in sequencing, such as sequencing by synthesis. The sequencer motif can include the sequence(s) needed to couple a library adaptor to a sequencing system and sequence the target polynucleotide.

The terms "sensitivity", "specificity", and "accuracy" as used herein refer to measures of agreement. Sensitivity generally refers to the percentage of actual positives identified in a test as positive. Sensitivity includes, for example, instances in which one should have found (diagnosed) a cancer (e.g., by detecting a variant) and did (e.g., as verified by sampling cellular DNA or tumor tissue). Sensitivity can be calculated using the following equation: Sensitivity=TP/(TP+FN). Specificity generally refers to the percentage of actual negatives identified in a test as negative. Specificity includes, for example, instances in which one should have found (diagnosed) no cancer (e.g., found no variants indicating cancer) and did not (e.g., as verified by sampling cellular DNA or tumor tissue). Specificity can be calculated using the following equation: Specificity=TN/(TN+FP). Subjects identified as positive in a test that are in reality positive are referred to as true positives (TP). Subjects identified as positive in a test that are in reality negative are referred to as false positives (FP). Subjects identified as negative in a test that are in reality negative are referred to as true negatives (TN). Subjects identified as negative in a test that are in reality positive are referred to as false negatives (FN).

Positive predictive value (PPV) can be measured by the percentage of subjects who test positive that are true positives. PPV can be calculated using the following equation: PPV=TP/(TP+FP), where TP are true positives and FP are false positives.

Negative predictive value (NPV) can be measured by the percentage of subjects who test negative that are true negatives. NPV can be calculated using the following equation: NPV=TN/(TN+FN), where TN are true negatives and FN are false negatives.

Accuracy can be measured by the percentage of subjects who test positive or negative that are true positives or true negatives, respectively. Accuracy can be calculated using the following formula: Accuracy=(TP+TN)/(TP+TN+FP+FN).

Precision can be measured by the percentage of subjects who test positive that are true positives and not false positives. Precision can be calculated using the following formula: precision=TP/(TP+FP).

I. Overview:

With improvements in sequencing and techniques to manipulate nucleic acids, there is a need in the art for improved methods and systems for using cell free DNA to detect and monitor disease. In particular, there is a need to balance efficient use of sequenced base pairs with high accuracy and sensitivity variant detection. Provided herein are methods for detecting cancer in a subject. The methods provided herein can be used to detect genetic variation with high sensitivity and accuracy in heterogeneous polynucleotide samples, such as cell-free DNA ("cfDNA").

An aspect of the present disclosure provides methods for detecting a cancer in a subject by detecting one or more genetic variants in a panel of regions of cell-free DNA molecules obtained from a subject. The panels of regions can have relatively small sizes, e.g., 50 kilobases (kb) or less. A "region" as described herein may refer to a contiguous portion of a genome. As a non-limiting example, a region may be a contiguous sequence of at least 1000 base pairs (bp). A genomic region can be a contiguous segment of at least 1000 nucleotides, at least 2000 nucleotides, at least 5000 nucleotides, at least 10,000 nucleotides, at least 25,000 nucleotides, at least 50,000 nucleotides, at least 100,000 nucleotides, at least 250,000 nucleotides, at least 500,000 nucleotides, or at least 1 million nucleotides. A genomic region can include an exon, an intron, a gene, an intergenic regulatory element, gene promoter, gene transcription start site, or a multigene region. The sizes of the regions can allow for deeper sequencing orders of nucleic acid molecules in a sample on a per base-read basis, which in turn enables detection of low-frequency genetic variants (e.g., at a minor allele frequency of about 0.001% or about 0.01%) in the cell-free DNA sample. Thus, the methods herein can be used for detecting cancers at a high sensitivity and/or a high specificity at a low cost. In some cases, the methods can be used for detecting a cancer with a sample that has low concentration of cell-free DNA and/or low-frequency genetic variants, such as a sample from an early stage cancer patient. A "locus" as described herein can refer to a nucleotide, a sequence of nucleotides, or a gene.

Methods herein can also allow for interrogating methylation status and genetic variants (e.g., SNVs, indels) in cfDNA (double-stranded and/or single-stranded), cell-free RNA (cfRNA) (including exosomal RNA) in one sample. Assays herein can be performed with high input amounts (e.g., up to 250 nanograms (ng), up to 300 ng, up to 350 ng, at least 50 ng, at least 100 ng, at least 150 ng, at least 200 ng, at least 250 ng, at least 300 ng, at least 350 ng, at least 400 ng, at least 450 ng, at least 500 ng, at least 550 ng, at least 600 ng, at least 650 ng, or at least 700 ng) of cell-free nucleic acids without saturation. A cleanup step (e.g., after end-repair and/or prior to ligation) can be omitted from the method, thus preserving unique molecules and shorter fragments in the sample. Lower hybridization temperature in the amplification, differential bait concentrations, amplification with primers that selectively amply GC-rich regions at higher efficiency, and/or sequencing steps can also be used for more uniform coverage across guanine-cytosine (GC), and less frequency towards allele imbalance.

An aspect of the present disclosure provides methods for detecting a tumor marker or genetic variant among the sequence reads of a gene panel, wherein detection of the tumor marker or genetic variant indicates the presence of cancer. In some embodiments, detection of a single marker or genetic variant is associated with the presence of cancer, and detection of a plurality of markers or genetic variants indicates the presence of cancer.

The methods can comprise one or more of the following steps: a) obtaining cell-free nucleic acid molecules from a sample of the subject; b) selecting a panel of regions from each of a plurality of different genes; c) subject the cell-free nucleic acid molecules to sequencing in one or more of the regions; and d) detecting one or more genetic variants in the sequence read generated from c). The one or more genetic variants can be indicative of a cancer in the subject.

II. Test Samples

Methods disclosed herein can comprise isolating one or more polynucleotides.

A polynucleotide can comprise any type of nucleic acid, such as DNA and/or RNA. For example, if a polynucleotide is DNA, it can be genomic DNA, complementary DNA (cDNA), or any other deoxyribonucleic acid. A polynucleotide can also be a cell-free nucleic acid such as cell-free DNA (cfDNA). For example, the polynucleotide can be circulating cfDNA. Circulating cfDNA may comprise DNA shed from bodily cells via apoptosis or necrosis. cfDNA shed via apoptosis or necrosis may originate from normal bodily cells. Where there is abnormal tissue growth, such as for cancer, tumor DNA may be shed. The circulating cfDNA can comprise circulating tumor DNA (ctDNA).

A polynucleotide can be double-stranded or single-stranded. Alternatively, a polynucleotide can comprise a combination of a double-stranded portion and a single-stranded portion. Polynucleotides do not have to be cell-free.

A sample can be any biological sample isolated from a subject. For example, a sample can comprise, without limitation, bodily fluid, whole blood, platelets, serum, plasma, stool, red blood cells, white blood cells or leukocytes, endothelial cells, tissue biopsies, synovial fluid, lymphatic fluid, ascites fluid, interstitial or extracellular fluid, the fluid in spaces between cells, including gingival crevicular fluid, bone marrow, cerebrospinal fluid, saliva, mucous, sputum, semen, sweat, urine, fluid from nasal brushings, fluid from a pap smear, or any other bodily fluids. A bodily fluid can include saliva, blood, or serum. For example, a polynucleotide can be cell-free DNA isolated from a bodily fluid, e.g., blood or serum. A sample can also be a tumor sample, which can be obtained from a subject by various approaches, including, but not limited to, venipuncture, excretion, ejaculation, massage, biopsy, needle aspirate, lavage, scraping, surgical incision, or intervention or other approaches. A sample can be a cell-free sample (e.g., not comprising any cells).

A sample can comprise a volume of plasma containing cell free DNA molecules. A sample may comprise a volume of plasma sufficient to achieve a given read depth. A volume of sampled plasma may be at least 0.5 milliliters (mL), 1 mL, 5 mL 10 mL, 20 mL, 30 mL, or 40 mL. A volume of sampled plasma at most 0.5 mL, 1 mL, 5 mL 10 mL, 20 mL, 30 mL, or 40 mL. A volume of sampled plasma may be 5 to 20 mL. A volume of sampled plasma may be 10 ml to 20 mL.

A sample can comprise various amount of nucleic acid that contains genome equivalents. For example, a sample of about 30 ng DNA can contain about 10,000 ($10^4$) haploid human genome equivalents and, in the case of cfDNA, about 200 billion ($2\times10^{11}$) individual polynucleotide molecules. Similarly, a sample of about 100 ng of DNA can contain about 30,000 haploid human genome equivalents and, in the case of cfDNA, about 600 billion individual molecules.

A sample can comprise nucleic acids from different sources. For example, a sample can comprise germline DNA or somatic DNA. A sample can comprise nucleic acids carrying mutations. For example, a sample can comprise DNA carrying germline mutations and/or somatic mutations. A sample can also comprise DNA carrying cancer-associated mutations (e.g., cancer-associated somatic mutations). In some embodiments, a sample comprises one or more of: a single base substitution, a copy number variation, an indel, a gene fusion, a transversion, a translocation, an inversion, a deletion, aneuploidy, partial aneuploidy, polyploidy, chromosomal instability, chromosomal structure alterations, chromosome fusions, a gene truncation, a gene amplification, a gene duplication, a chromosomal lesion, a DNA lesion, abnormal changes in nucleic acid chemical modifications, abnormal changes in epigenetic patterns, abnormal changes in distributions of nucleic acid (e.g., cfDNA) fragments across genomic regions, abnormal changes in distributions of nucleic acid (e.g., cfDNA) fragment lengths, and abnormal changes in nucleic acid methylation.

Methods herein can comprise obtaining certain amount of nucleic acid molecules, e.g., cell-free nucleic acid molecules from a sample. For example, the method can comprise obtaining up to about 600 ng, up to about 500 ng, up to about 400 ng, up to about 300 ng, up to about 200 ng, up to about 100 ng, up to about 50 ng, or up to about 20 ng of cell-free nucleic acid molecules from a sample. The method can comprise obtaining at least 1 femtogram (fg), at least 10 fg, at least 100 fg, at least 1 picogram (pg), at least 10 pg, at least 100 pg, at least 1 ng, at least 10 ng, at least 100 ng, at least 150 ng, or at least 200 ng of cell-free nucleic acid molecules. The method can comprise obtaining at most 1 femtogram (fg), at most 10 fg, at most 100 fg, at most 1 picogram (pg), at most 10 pg, at most 100 pg, at most 1 ng, at most 10 ng, at most 100 ng, at most 150 ng, or at most 200 ng of cell-free nucleic acid molecules. The method can comprise obtaining 1 femtogram (fg) to 200 ng, 1 picogram (pg) to 200 ng, 1 ng to 100 ng, 10 ng to 150 ng, 10 ng to 200 ng, 10 ng to 300 ng, 10 ng to 400 ng, 10 ng to 500 ng, 10 ng to 600 ng, 10 ng to 700 ng, 10 ng to 800 ng, 10 ng to 900 ng, or 10 ng to 1000 ng of cell-free nucleic acid molecules. An amount of cell-free nucleic acid molecules may be equivalent to a number of haploid genome copies. Because a haploid genome copy has a mass of about 3.3 picograms (pg), each nanogram (ng) of cell-free nucleic molecules may be equivalent to about 300 haploid genome copies. For example, 5 ng of cell-free nucleic acid molecules may be equivalent to 1,500 genome copies.

A cell-free nucleic acid can be any extracellular nucleic acid that is not attached to a cell. A cell-free nucleic acid can be a nucleic acid circulating in blood. Alternatively, a cell-free nucleic acid can be a nucleic acid in other bodily fluid disclosed herein, e.g., urine. A cell-free nucleic acid can be a deoxyribonucleic acid ("DNA"), e.g., genomic DNA, mitochondrial DNA, or a fragment thereof. A cell-free nucleic acid can be a ribonucleic acid ("RNA"), e.g., mRNA, short-interfering RNA (siRNA), microRNA (miRNA), circulating RNA (cRNA), transfer RNA (tRNA), ribosomal RNA (rRNA), small nucleolar RNA (snoRNA), Piwi-interacting RNA (piRNA), long non-coding RNA (long ncRNA), or a fragment thereof. In some cases, a cell-free nucleic acid is a DNA/RNA hybrid. A cell-free nucleic acid can be double-stranded, single-stranded, or a hybrid thereof. A cell-free nucleic acid can be released into bodily fluid through secretion or cell death processes, e.g., cellular necrosis and apoptosis.

A cell-free nucleic acid can comprise one or more epigenetically modifications. For example, a cell-free nucleic acid can be acetylated, methylated, ubiquitylated, phosphorylated, sumoylated, ribosylated, and/or citrullinated. For example, a cell-free nucleic acid can be methylated cell-free DNA.

Cell-free DNA typically has a size distribution of about 110 to about 230 nucleotides, with a mode of about 168 nucleotides. A second, minor peak detected in assays quantifying cell-free nucleic acid molecule length has a range between 240 to 440 nucleotides. Additional higher order nucleotide peaks are present as well at longer lengths.

In some embodiments of the present disclosure, cell-free nucleic acids can be at most 1,000 nucleotides (nt) in length, at most 500 nucleotides in length, at most 400 nucleotides in length, at most 300 nucleotides in length, at most 250 nucleotides in length, at most 225 nucleotides in length, at most 200 nucleotides in length, at most 190 nucleotides in length, at most 180 nucleotides in length, at most 170 nucleotides in length, at most 160 nucleotides in length, at most 150 nucleotides in length, at most 140 nucleotides in length, at most 130 nucleotides in length, at most 120 nucleotides in length, at most 110 nucleotides in length, or at most 100 nucleotides in length.

In some embodiments of the present disclosure, cell-free nucleic acids can be at least 1,000 nucleotides in length, at least 500 nucleotides in length, at least 400 nucleotides in length, at least 300 nucleotides in length, at least 250 nucleotides in length, at least 225 nucleotides in length, at least 200 nucleotides in length, at least 190 nucleotides in length, at least 180 nucleotides in length, at least 170 nucleotides in length, at least 160 nucleotides in length, at least 150 nucleotides in length, at least 140 nucleotides in length, at least 130 nucleotides in length, at least 120 nucleotides in length, at least 110 nucleotides in length, or at least 100 nucleotides in length. Cell-free nucleic acids can be from 140 to 180 nucleotides in length.

In some embodiments of the present disclosure, cell free nucleic acids in a subject may derive from a tumor. For example cell-free DNA isolated from a subject can comprise circulating tumor DNA, (ctDNA). Next generation sequencing allows detection and measurement of rare mutations. Detection of mutations relative to germline sequence in a fraction of cell-free DNA can indicate the presence of ctDNA, thus indicating the presence of a tumor. Sequencing cell free DNA may allow detection a genetic variant that is known to indicate the presence of cancer. For example sequencing cell free DNA may allow detection of mutations in cancer related genes.

Isolation and Extraction

Cell-free polynucleotides may be fetal in origin (via fluid taken from a pregnant subject), or may be derived from tissue of the subject itself. Cell-free polynucleotides may derive from healthy tissue, from diseased tissue such as tumor tissue, or from a transplant organ.

In some embodiments, cell-free polynucleotides are derived from a blood sample or a fraction thereof. For example, a blood sample (e.g., about 10 to about 30 mls) can be taken from a subject, centrifuged to remove cells, and the resulting plasma used for cfDNA extraction.

Isolation and extraction of polynucleotides may be performed through collection of bodily fluids using a variety of techniques. In some cases, collection may comprise aspiration of a bodily fluid from a subject using a syringe. In other cases collection may comprise pipetting or direct collection of fluid into a collecting vessel.

After collection of bodily fluid, polynucleotides may be isolated and extracted using a variety of techniques utilized in the art. In some cases, cell-free DNA may be isolated, extracted and prepared using commercially available kits such as the Qiagen Qiamp® Circulating Nucleic Acid Kit protocol. In other examples, Qiagen Qubit™ dsDNA HS Assay kit protocol, Agilent™ DNA 1000 kit, or TruSeq™ Sequencing Library Preparation; Low-Throughput (LT) protocol may be used.

Generally, cell free polynucleotides may be extracted and isolated by from bodily fluids through a partitioning step in which cell-free DNAs, as found in solution, are separated from cells and other non-soluble components of the bodily fluid. Partitioning may include, but is not limited to, techniques such as centrifugation or filtration. In other cases, cells may not be partitioned from cell-free DNA first, but rather lysed. For instance, the genomic DNA of intact cells may be partitioned through selective precipitation. Sample partitioning may be combined with tagging nucleic acids with identifiers (such as identifiers comprising bar codes), or may be performed in a method without the use of an identifier. A sample can be divided into partitions such that each partition can be barcoded independently (e.g., with one unique bar code per partition), and sequencing data from the partitions can later be recombined. A sample can be divided into partitions, and the nucleic acid molecules non-uniquely tagged with respect to one another within a partition, or between partitions. In some embodiments, a sample can be divided into partitions without the use of identifiers. In one example, a cfDNA sample is divided into 4 or more partitions, wherein each partition is an a spatially addressable location. Sample preparation and sequencing is performed on each spatially addressable partition, and the bioinformatics pipeline utilizes the addressable location to further identify a unique molecule. In one example, nucleic acid molecules can be divided into partitions, for example, containing different types of nucleic acid molecules (e.g., double stranded nucleic acids such as DNA and/or single stranded nucleic acids such as RNA and/or single stranded DNA). Cell-free polynucleotides, including DNA, may remain soluble and may be separated from insoluble genomic DNA and extracted. Generally, after addition of buffers and other wash steps specific to different kits, DNA may be precipitated using isopropanol precipitation. Further clean up steps may be used such as silica based columns or beads (such as magnetic beads) to remove contaminants or salts. General steps may be optimized for specific applications. Non-specific bulk carrier polynucleotides, for example, may be added throughout the reaction to optimize certain aspects of the procedure such as yield.

In some embodiments, a plasma sample is treated to degrade proteinase K and DNA is precipitated with isopropanol and subsequently captured on a Qiagen column. The DNA then can be eluted (e.g., using 100 microliters (μl) of eluent such as water or Tris-EDTA (TE) elution buffer). In some embodiments, a portion of the DNA can be selected based on size (e.g., DNA of 500 nucleotides or fewer in length), for example, using Solid Phase Reversible Immobilization (SPRI) beads, such as AgenCourt®AMPure® beads. In some embodiments, the DNA can be resuspended in a smaller volume, such as 30 μl of water, and checked for size distribution of the DNA (e.g., to check for a major peak at 166 nucleotides and a minor peak at 330 nucleotides). Approximately 5 ng of DNA may be equivalent to about 1500 haploid genome equivalents ("HGE").

After extraction, samples may yield up to 1 microgram (μg) of DNA, up to 800 ng of DNA, up to 500 ng of DNA, up to 300 ng of DNA, up to 250 ng of DNA, up to 200 ng of DNA, up to 180 ng of DNA, up to 160 ng of DNA, up to 140 ng of DNA, up to 120 ng of DNA, up to 100 ng of DNA, up to 90 ng of DNA, up to 80 ng of DNA, up to 70 ng of DNA, up to 60 ng of DNA, up to 50 ng of DNA, up to 40 ng of DNA, up to 30 ng of DNA, up to 20 ng of DNA, up to 10 ng of DNA, up to 9 ng of DNA, up to 8 ng of DNA, up to 7 ng of DNA, up to 6 ng of DNA, up to 5 ng of DNA, up to 4 ng of DNA, up to 3 ng of DNA, up to 2 ng of DNA, or up to 1 ng of DNA.

After extraction, samples may yield at least 1 ng of DNA, at least 3 ng of DNA, at least 5 ng of DNA, at least 7 ng of DNA, at least 10 ng of DNA, at least 20 ng of DNA, at least 30 ng of DNA, at least 40 ng of DNA, at least 50 ng of DNA, at least 70 ng of DNA, at least 100 ng of DNA, at least 150 ng of DNA, at least 200 ng of DNA, at least 250 ng of DNA, at least 300 ng of DNA, at least 400 ng of DNA, at least 500 ng of DNA, or at least 700 ng of DNA.

One or more of the cell-free nucleic acids can be isolated from a cellular fragment in a sample. In some cases, one or more of the cell-free nucleic acids are isolated from membrane, cellular organelles, nucleosomes, exosomes, or nucleus, mitochondria, rough endoplasmic reticulum, ribosomes, smooth endoplasmic reticulum, chloroplasts, Golgi apparatus, Golgi bodies, glycoproteins, glycolipids, cisternaes, liposomes, peroxisomes, glyoxysomes, centriole, cytoskeleton, lysosomes, cilia, flagellum, contractile vacuole, vesicles, nuclear envelopes, vacuoles, microtubule, nucleoli, plasma membrane, endosomes, chromatins, or a combination thereof. One or more of the cell-free nucleic acids can be isolated from one or more exosomes. In some cases, one or more of the cell-free nucleic acids are isolated from one or more cell surface bound nucleic acids.

Purification of cell free DNA may be accomplished using any methodology, including, but not limited to, the use of commercial kits and protocols provided by companies such as Sigma Aldrich, Life Technologies, Promega, Affymetrix, IBI or the like. Kits and protocols may also be non-commercially available.

After isolation, in some cases, the cell free polynucleotides may be pre-mixed with one or more additional materials, such as one or more reagents (e.g., ligase, protease, polymerase) prior to sequencing.

Cell-free DNA can be sequenced at a read depth sufficient to detect a genetic variant at a frequency in a sample as low as 0.0005%. Cell-free DNA can be sequenced at a read depth sufficient to detect a genetic variant at a frequency in a sample as low as 0.001%. Cell-free DNA can be sequenced at a read depth sufficient to detect a genetic variant at a frequency in a sample as low as 1.0%, 0.75%, 0.5%, 0.25%, 0.1%, 0.075%, 0.05%, 0.025%, 0.01%, or 0.005%. Thus, sequencing cell free DNA allows very sensitive detection of cancer in a subject.

In some embodiments, cellular DNA can be used as an alternative to cell-free DNA. Exemplary cells include, but are not limited to, endothelial cells, cells from tissue biopsies, tumor cells, and cells from whole blood including platelets, red blood cells, and white blood cells or leukocytes. In some embodiments, sequence data from cellular DNA are obtained at the same or greater read depth than cell-free DNA sequence data.

Methods herein can be used to detect cancer in a subject. Cell free DNA can be sequenced in subjects not known to have cancer, or suspected of having cancer to diagnose the presence of absence of a cancer. Sequencing cell free DNA provides a noninvasive method for early detection of cancer or for 'biopsy' of a known cancer. Cell free DNA can be sequenced in subjects diagnosed with cancer to provide information about the cancer. Cell free DNA can be sequenced in subjects before and after treatment for cancer to determine the efficacy of the treatment.

A subject may be suspected of having cancer or may not be suspected of having cancer. A subject may have experienced symptoms consistent with a diagnosis of cancer. A subject may not have experienced any symptoms, or may have exhibited symptoms not consistent with cancer. A subject may have been diagnosed with a cancer based on biological imaging methods. A subject may not have a cancer that is detectable by imaging methods. The imaging methods can be positron emission tomography scan, magnetic resonance imaging, X-ray, computerized axial tomography scan, ultrasound, or a combination thereof.

A subject may exhibit a cancer. Alternatively, a subject may not detectably exhibit a cancer. In some cases, a subject who does not detectably exhibit a cancer can have a cancer, but have no detectable symptoms. Subjects not known to have cancer, or suspected of having cancer, can have cancer that is not detectable using various cancer screening methods. No cancer may be detected using various imaging methods. The imaging methods may include, for example, positron emission tomography scan, magnetic resonance imaging, X-ray, computerized axial tomography scan, endoscopy, ultrasound, or a combination thereof. For a subject not known to have cancer or suspected of having cancer, tests such as tissue biopsy, bone marrow aspiration, pap tests, fecal occult blood tests, protein biomarker detection, e.g., prostate-specific antigen test, alpha-fetoprotein blood test, or CA-125 test, or a combination thereof, may indicate that a subject does not have cancer, e.g., detect no cancer for the subject. In other cases, a subject who does not detectably exhibit a cancer may not have any cancer.

The subject may be at higher risk of having cancer than a general population. The subject may have a family history of cancer. The subject may have known genetic sources of cancer risk. The subject may have been exposed to environmental conditions known to increase or cause cancer risk. The subjects can be patients whose only risk factors for cancer are age and/or gender. The subject may have no known cancer risk factors.

The subject may have been diagnosed with a cancer. The cancer may be early stage or late stage. The cancer may be metastatic or may not be metastatic. Types of cancer that a subject may have been diagnosed with include, but are not limited to: carcinomas, sarcomas, lymphomas, leukemia's, germ cell tumors and blastomas. Types of cancer that a subject may have been diagnosed with include, but are not limited to: Acute lymphoblastic leukemia (ALL), Acute myeloid leukemia, Adrenocortical carcinoma, adult acute Myeloid leukemia, adult carcinoma of unknown primary site, adult malignant Mesothelioma, AIDS-related cancers, AIDS-related lymphoma, Anal cancer, Appendix cancer, Astrocytoma, childhood cerebellar or cerebral, Basal-cell carcinoma, Bile duct cancer, Bladder cancer, Bone tumor, osteosarcoma/malignant fibrous histiocytoma, Brain cancer, Brainstem glioma, Breast cancer, Bronchial adenomas/carcinoids, Burkitt Lymphoma, Carcinoid tumor, Carcinoma of unknown primary, Central nervous system lymphoma, cerebellar astrocytoma, cerebral astrocytoma/malignant glioma, Cervical cancer, childhood acute Myeloid leukemia, childhood cancer of unknown primary site, Childhood cancers, childhood cerebral astrocytoma, childhood Mesothelioma, Chondrosarcoma, Chronic lymphocytic leukemia, Chronic myelogenous leukemia, Chronic myeloproliferative disorders, Colon cancer, Cutaneous T-cell lymphoma, Desmoplastic small round cell tumor, Endometrial cancer, endometrial Uterine cancer, Ependymoma, Epitheliod Hemangioendothelioma (EHE), Esophageal cancer, Ewing family of tumors Sarcoma, Ewing's sarcoma in the Ewing family of tumors, Extracranial germ cell tumor, Extragonadal germ cell tumor, Extrahepatic bile duct cancer, Eye cancer, intraocular melanoma, Gallbladder cancer, Gastric (stomach) cancer, Gastric carcinoid, Gastrointestinal carcinoid tumor, Gastrointestinal stromal tumor (GIST), Gestational trophoblastic tumor, Glioma of the brain stem, Glioma, Hairy cell leukemia, Head and neck cancer, Heart cancer, Hepatocellular (liver) cancer, Hodgkin lymphoma, Hypopharyngeal cancer, Hypothalamic and visual pathway glioma, Islet cell carcinoma (endocrine pancreas), Kaposi sarcoma, Kidney cancer (renal cell cancer), Laryngeal cancer, Leukaemia, acute lymphoblastic (also called acute lymphocytic leukaemia), Leukaemia, acute myeloid (also called acute myelogenous leukemia), Leukaemia, chronic lymphocytic (also called chronic lymphocytic leukemia), Leukaemias, Leukemia, chronic myelogenous (also called chronic myeloid leukemia), Leukemia, hairy cell, Lip and oral cavity cancer, Liposarcoma, Liver cancer (primary), Lung cancer, non-small cell, Lung cancer, small cell, Lymphoma (AIDS-related), Lymphomas, Macroglobulinemia, Waldenström, Male breast cancer, Malignant fibrous histiocytoma of bone/osteosarcoma, medulloblastoma, Melanoma, Merkel cell cancer, Metastatic squamous neck cancer with occult primary, Mouth cancer, Multiple endocrine neoplasia syndrome, childhood, multiple Myeloma (cancer of the bone-marrow), Multiple myeloma/plasma cell neoplasm, Mycosis fungoides, Myelodysplastic syndromes, Myelodysplastic/myeloproliferative diseases, Myelogenous leukemia, chronic, Myxoma, Nasal cavity and paranasal sinus cancer, Nasopharyngeal carcinoma, Neuroblastoma, Non-Hodgkin Lymphomas, Non-small cell lung cancer, Oligodendroglioma, Oral cancer, Oropharyngeal cancer, Osteosarcoma/malignant fibrous histiocytoma of bone, Ovarian cancer, Ovarian epithelial cancer (surface epithelial-stromal tumor), Ovarian germ cell tumor, Ovarian low malignant potential tumor, Pancreatic cancer, Pancreatic cancer, islet cell, Paranasal sinus and nasal cavity cancer, Parathyroid cancer, Penile cancer, Pharyngeal cancer, Pheochromocytoma, Pineal astrocytoma, Pineal germinoma, Pineoblastoma and supratentorial primitive neuroectodermal tumors, Pituitary adenoma, Plasma cell neoplasia/Multiple myeloma, Pleuro- pulmonary blastoma, Primary central nervous system lymphoma, Prostate cancer, Rectal cancer, Renal cell carcinoma (kidney cancer), Renal pelvis and ureter transitional cell cancer, Retinoblastoma, Rhabdomyosarcoma, Salivary gland cancer, Sézary syndrome, Skin cancer (melanoma), Skin cancer (non-melanoma), Skin carcinoma, Merkel cell, Small cell lung cancer, Small intestine cancer, soft tissue Sarcoma, Squamous cell carcinoma, Squamous neck cancer with occult primary, metastatic, Stomach cancer, Supratentorial primitive neuroectodermal tumor, T-Cell lymphoma, cutaneous, Testicular cancer, Throat cancer, Thymoma and thymic carcinoma, Thymoma, Thyroid cancer, Transitional cell cancer of the renal pelvis and ureter, Ureter and renal pelvis, transitional cell cancer, Urethral cancer, Uterine sarcoma, Vaginal cancer, visual pathway and hypothalamic glioma, Visual pathway and hypothalamic glioma, childhood, Vulvar cancer, Waldenström macroglobulinemia, and Wilms tumor (kidney cancer).

The subject may have previously received treatment for a cancer. The subject may have received surgical treatment, radiation treatment, chemotherapy, targeted cancer therapeutics or a cancer immunotherapy. The subject may have been treated with a cancer vaccine. The subject may have been treated with an experimental cancer treatment. The subject may not have received a cancer treatment. The subject may be in remission from cancer. The subject may have previously received a treatment for cancer and not detectably exhibit any symptoms.

In some embodiments, the methods and systems described herein can detect cancer before the cancer may be detectable using conventional methods, e.g., at least 1 year, 6 months, 3 months, or 1 month before the cancer may be detectable by imaging, or at least 1 year, 6 months, 3 months, or 1 month before the cancer may be diagnosed at stage I, stage II, stage III, or stage IV, or at least 1 year, 6 months, 3 months, or 1 month before the cancer may recur.

III. Genetic Analysis

Certain DNA sequencing methods use sequence capture to enrich for sequences of interest. Sequence capture typically involves the use of oligonucleotide probes that hybridize to the sequence of interest. A probe set strategy can involve tiling the probes across a region of interest. Such probes can be, e.g., about 60 to 120 bases long. The set can have a depth of about 2×, 3×, 4×, 5×, 6×, 8×, 9×, 10×, 15×, 20×, 50× or more. The effectiveness of sequence capture depends, in part, on the length of the sequence in the target molecule that is complementary (or nearly complementary) to the sequence of the probe. Enriched nucleic acid molecules can be representative of more than 5,000 bases of the human genome, more than 10,000 bases of the human genome, more than 15,000 bases of the human genome, more than 20,000 bases of the human genome, more than 25,000 bases of the human genome, more than 30,000 bases of the human genome, more than 35,000 bases of the human genome, more than 40,000 bases of the human genome, more than 45,000 bases of the human genome, more than 50,000 bases of the human genome, more than 55,000 bases of the human genome, more than 60,000 bases of the human genome, more than 65,000 bases of the human genome, more than 70,000 bases of the human genome, more than 75,000 bases of the human genome, more than 80,000 bases of the human genome, more than 85,000 bases of the human genome, more than 90,000 bases of the human genome, more than 95,000 bases of the human genome, or more than 100,000 bases of the human genome. Enriched nucleic acid molecules can be representative of no greater than 5,000 bases of the human genome, no greater than 10,000 bases of the human genome, no greater than 15,000 bases of the human genome, no greater than 20,000 bases of the human genome, no greater than 25,000 bases of the human genome, no greater than 30,000 bases of the human genome, no greater than 35,000 bases of the human genome, no greater than 40,000 bases of the human genome, no greater than 45,000 bases of the human genome, no greater than 50,000 bases of the human genome, no greater than 55,000 bases of the human genome, no greater than 60,000 bases of the human genome, no greater than 65,000 bases of the human genome, no greater than 70,000 bases of the human genome, no greater than 75,000 bases of the human genome, no greater than 80,000 bases of the human genome, no greater than 85,000 bases of the human genome, no greater than 90,000 bases of the human genome, no greater than 95,000 bases of the human genome, or no greater than 100,000 bases of the human genome. Enriched nucleic acid molecules can be representative of 5,000-100,000 bases of the human genome, 5,000-50,000 bases of the human genome, 5,000-30,000 bases of the human genome, 10,000-100,000 bases of the human genome, 10,000-50,000 bases of the human genome, or 10,000-30,000 bases of the human genome. Enriched nucleic acid molecules can be representative of various nucleic acid features, including genetic variants such as nucleotide variants (SNVs), copy number variants (CNVs), insertions or deletions (e.g., indels), nucleosome regions associated with cancer, gene fusions, and inversions.

Generally, the methods and systems provided herein are useful for preparation of cell free polynucleotide sequences to a down-stream application sequencing reaction. The sequencing method can be massively parallel sequencing, that is, simultaneously (or in rapid succession) sequencing any of at least 100, 1000, 10,000, 100,000, 1 million, 10 million, 100 million, 1 billion, or 10 billion polynucleotide molecules. Sequencing methods may include, but are not limited to: high-throughput sequencing, pyrosequencing, sequencing-by-synthesis, single-molecule sequencing, nanopore sequencing, semiconductor sequencing, sequencing-by-ligation, sequencing-by-hybridization, RNA-Seq (Illumina), Digital Gene Expression (Helicos), Next generation sequencing, Single Molecule Sequencing by Synthesis (SMSS) (Helicos), massively-parallel sequencing, Clonal Single Molecule Array (Solexa), shotgun sequencing, Maxam-Gilbert or Sanger sequencing, primer walking, sequencing using PacBio, SOLiD, Ion Torrent, or Nanopore platforms and any other sequencing methods known in the art.

Individual polynucleotide fragments in a genomic nucleic acid sample (e.g., genomic DNA sample) can be uniquely identified by tagging with non-unique identifiers, e.g., non-uniquely tagging the individual polynucleotide fragments.

Sequencing Panel

To improve the likelihood of detecting tumor indicating mutations, the region of DNA sequenced may comprise a panel of genes or genomic regions. Selection of a limited region for sequencing (e.g., a limited panel) can reduce the total sequencing needed (e.g., a total amount of nucleotides sequenced. A sequencing panel can target a plurality of different genes or regions to detect a single cancer, a set of cancers, or all cancers.

In some aspects, a panel targets a plurality of different genes or genomic regions is selected such that a determined proportion of subjects having a cancer exhibits a genetic variant or tumor marker in one or more different genes or genomic regions in the panel. The panel may be selected to limit a region for sequencing to a fixed number of base pairs.

The panel may be selected to sequence a desired amount of DNA. The panel may be further selected to achieve a desired sequence read depth. The panel may be selected to achieve a desired sequence read depth or sequence read coverage for an amount of sequenced base pairs. The panel may be selected to achieve a theoretical sensitivity, a theoretical specificity and/or a theoretical accuracy for detecting one or more genetic variants in a sample.

Probes for detecting the panel of regions can include those for detecting hotspots regions as well as nucleosome-aware probes (e.g., KRAS codons 12 and 13) and may be designed to optimize capture based on analysis of cfDNA coverage and fragment size variation impacted by nucleosome binding patterns and GC sequence composition. Regions used herein can also include non-hotspot regions optimized based on nucleosome positions and GC models. The panel can comprise a plurality of subpanels, including subpanels for identifying tissue of origin (e.g., use of published literature to define 50-100 baits representing genes with most diverse transcription profile across tissues (not necessarily promoters)), whole genome scaffold (e.g., for identifying ultraconservative genomic content and tiling sparsely across chromosomes with handful of probes for copy number base lining purposes), transcription start site (TSS)/CpG islands (e.g., for capturing differential methylated regions (e.g., Differentially Methylated Regions (DMRs)) in for example in promoters of tumor suppressor genes (e.g., SEPT9/VIM in colorectal cancer)). In some embodiments, markers for a tissue of origin are tissue-specific epigenetic markers.

The one or more regions in the panel can comprise one or more loci from one or a plurality of genes. The plurality of genes may be selected for sequencing and tumor marker detection. Genes included in the region to be sequenced may be selected from genes known to be involved in cancer, or from genes not involved in cancer. For example the plurality of genes in the panel may be oncogenes, tumor suppressors, growth factors, DNA repair genes, signaling genes, transcription factors, receptors or metabolic genes. Examples of genes that may be in the panel include, but are not limited to: APC, AR, ARID1A, BRAF, BRCA1, BRCA2, CCND1, CCND2, CCNE1, CDK4, CDK6, CDKN2A, CDKN2B, EGFR, ERBB2, FGFR1, FGFR2, HRAS, KIT, KRAS, MET, MYC, NF1, NRAS, PDGFRA, PIK3CA, PTEN, RAF1, TP53, AKT1, ALK, ARAF, ATM, CDH1, CTNNB1, ESR1, EZH2, FBXW7, FGFR3, GATA3, GNA11, GNAQ, GNAS, HNF1A, IDH1, IDH2, JAK2, JAK3, MAP2K1, MAP2K2, MLH1, MPL, NFE2L2, NOTCH1, NPM1, NTRK1, PTPN11, RET, RHEB, RHOA, RIT1, ROS1, SMAD4, SMO, SRC, STK11, TERT, VHL.

In some cases, the one or more regions in the panel can comprise one or more loci from one or a plurality of genes, including one or more of AKT1, ALK, APC, ATM, BRAF, CTNNB1, EGFR, ERBB2, ESR1, FGFR2, GATA3, GNAS, IDHL IDH2, KIT, KRAS, MET, NRAS, PDGFRA, PIK3CA, PTEN, RB1, SMAD4, STK11, and TP53.

In some cases, the one or more regions in a panel for colorectal cancer can comprise one or more loci from one or a plurality of genes, including one of, two of, three of, four of, or five of TP53, APC, BRAF, KRAS, and NRAS. In some cases, the one or more regions in a panel for ovarian cancer can comprise one or more loci from one or a plurality of genes, including TP53. In some cases, the one or more regions in a panel for pancreatic cancer can comprise one or more loci from one or a plurality of genes, including one or both of TP53 and KRAS. In some cases, the one or more regions in a panel for lung adenocarcinoma can comprise one or more loci from one or a plurality of genes, including one of, two of, three of, four of, five of, six of, seven of, or eight of TP53, BRAF, KRAS, EGFR, ERBB2, MET, STK11, and ALK. In some cases, the one or more regions in a panel for lung squamous cell carcinoma can comprise one or more loci from one or a plurality of genes, including one of, two of, three of, four of, or five of TP53, BRAF, KRAS, MET, and ALK. In some cases, the one or more regions in a panel for breast cancer can comprise one or more loci from one or a plurality of genes, including one of, two of, three of, or four of TP53, GATA3, PIK3CA, and ESR1. In some cases, one or more regions in a panel can comprise one or more loci from a combination of any of the above genes, for example, to detect a combination of cancer types. In some cases, one or more regions in a panel can comprise one or more loci from each of the preceding genes, for example, in a pan-cancer panel.

In some cases, the one or more regions in a panel for lung cancer can comprise one or more loci from a plurality of genes, including one of, two of, three of, four of, five of, six of, seven of, eight of, nine of, 10 of, 11 of, 12 of, 13 of, 14 of, 15 of, 16 of, 17 of, 18 of, 19 of, or 20 of EGFR, KRAS, TP53, CDKN2A, STK11, BRAF, PIK3CA, RB1, ERBB2, PTEN, NFE2L2, MET, CTNNB1, NRAS, MUC16, NF1, BAI3, SMARCA4, ATM, NTRK3, and ERBB4. Such a panel also may include, or have substituted for any or all of the above, any or all of an EGFR Exon 19 deletion, EGFR L858R, EGFR C797S, EGFR T790M, EGFR S645C, ARAF S214C and S214F, ERBB2 S418T, MET exon 14 skipping, SNVs and indels. Many of these genes may be clinically actionable, such that an observed anomaly in MAF (e.g., significantly higher or lower than in normal control subjects) may be indicative of a clinical state relevant to lung cancer, such as diagnosis, prognosis, risk stratification, treatment selection, tumor resistance to treatment, tumor burden, etc. Such a lung cancer targeted panel may comprise a relatively small number of these lung cancer associated genes.

In some cases, the one or more regions in a panel for breast cancer can comprise one or more loci from a plurality of genes, including any one of, or any combination of, ACVRL1, AFF2, AGMO, AGTR2, AHNAK, AHNAK2, AKAP9, AKT1, AKT2, ALK, APC, ARID1A, ARID1B, ARID2, ARID5B, ASXL1, ASXL2, ATR, BAP1, BCAS3, BIRC6, BRAF, BRCA1, BRCA2, BRIP1, CACNA2D3, CASP8, CBFB, CCND3, CDH1, CDKN1B, CDKN2A, CHD1, CHEK2, CLK3, CLRN2, COL12A1, COL22A1, COL6A3, CTCF, CTNNA1, CTNNA3, DCAF4L2, DNAH11, DNAH2, DNAH5, DTWD2, EGFR, EP300, ERBB2, ERBB3, ERBB4, FAM20C, FANCA, FANCD2, FBXW7, FLT3, FOXO1, FOXO3, FOXP1, FRMD3, GATA3, GH1, GLDC, GPR124, GPR32, GPS2, HDAC9, HERC2, HIST1H2BC, HRAS, JAK1, KDM3A, KDM6A, KLRG1, KMT2C, KRAS, L1CAM, LAMA2, LAMB3, LARGE, LDLRAP1, LIFR, LIPI, MAGEA8, MAP2K4, MAP3K1, MAP3K10, MAP3K13, MBL2, MEN1, LL2, MLLT4, MTAP, MUC16, MYH9, MYO1A, MYO3A, NCOA3, NCOR1, NCOR2, NDFIP1, NEK1, NF1, NF2, NOTCH1, NPNT, NR2F1, NR3C1, NRAS, NRG3, NT5E, OR6A2, PALLD, PBRM1, PDE4DIP, PIK3CA, PIK3R1, PPP2CB, PPP2R2A, PRKACG, PRKCE, PRKCQ, PRKCZ, PRKG1, PRPS2, PRR16, PTEN, PTPN22, PTPRD, PTPRM, RASGEF1B, RB1, ROS1, RPGR, RUNX1, RYR2, SBNO1, SETD1A, SETD2, SETDB1, SF3B1, SGCD, SHANK2, SIAH1, SIK1, SIK2, SMAD2, SMAD4, SMARCB1, SMARCC1, SMARCC2, SMARCD1, SPACA1, STAB2, STK11, STMN2, SYNE1, TAF1, TAF4B, TBL1XR1, TBX3, TG, THADA, THSD7A, TP53, TTYH1, UBR5, USH2A, USP28, USP9X, UTRN, and ZFP36L1. Many of these genes may be clinically actionable, such that an observed anomaly in MAF (e.g., significantly higher or lower than in normal control subjects) may be indicative of a clinical state relevant to breast cancer, such as diagnosis, prognosis, risk stratification, treatment selection, tumor resistance to treatment, tumor burden, etc. Such a breast cancer targeted panel may comprise a relatively small number of these breast cancer associated genes.

In some cases, the one or more regions in a panel for colorectal cancer can comprise one or more loci from a plurality of genes, including one of, two of, three of, four of, five of, or six of TP53, BRAF, KRAS, APC, TGFBR, and PIK3CA. Many of these genes may be clinically actionable, such that an observed anomaly in MAF (e.g., significantly higher or lower than in normal control subjects) may be indicative of a clinical state relevant to colorectal cancer, such as diagnosis, prognosis, risk stratification, treatment selection, tumor resistance to treatment, tumor burden, etc. Such a colorectal cancer targeted panel may comprise a relatively small number of these colorectal cancer associated genes.

In some embodiments, the one or more regions in the panel comprise one or more loci from one or a plurality of genes for detecting residual cancer after surgery. This detection can be earlier than is possible for existing methods of cancer detection. In some embodiments, the one or more regions in the panel comprise one or more loci from one or a plurality of genes for detecting cancer in a high-risk patient population. For example, smokers have much higher rates of lung cancer than the general population. Moreover, smokers can develop other lung conditions that make cancer detection more difficult, such as the development of irregular nodules in the lungs. In some embodiments, the methods described herein detect cancer in high risk patients earlier than is possible for existing methods of cancer detection.

A region may be selected for inclusion in a sequencing panel based on a number of subjects with a cancer that have a tumor marker in that gene or region. A region may be selected for inclusion in a sequencing panel based on prevalence of subjects with a cancer and a tumor marker present in that gene. Presence of a tumor marker in a region may be indicative of a subject having cancer.

In some instances, the panel may be selected using information from one or more databases. The information regarding a cancer may be derived from cancer tumor biopsies or cfDNA assays. A database may comprise information describing a population of sequenced tumor samples. A database may comprise information about mRNA expression in tumor samples. A databased may comprise information about regulatory elements in tumor samples. The information relating to the sequenced tumor samples may include the frequency various genetic variants and describe the genes or regions in which the genetic variants occur. The genetic variants may be tumor markers. A non-limiting example of such a database is COSMIC. COSMIC is a catalogue of somatic mutations found in various cancers. For a particular cancer, COSMIC ranks genes based on frequency of mutation. A gene may be selected for inclusion in a panel by having a high frequency of mutation within a given gene. For instance, COSMIC indicates that 33% of a population of sequenced breast cancer samples have a mutation in TP53 and 22% of a population of sampled breast cancers have a mutation in KRAS. Other ranked genes, including APC, have mutations found only in about 4% of a population of sequenced breast cancer samples. TP53 and KRAS may be included in a sequencing panel based on having relatively high frequency among sampled breast cancers (compared to APC, for example, which occurs at a frequency of about 4%). COSMIC is provided as a non-limiting example, however, any database or set of information may be used that associates a cancer with tumor marker located in a gene or genetic region. In another example, as provided by COSMIC, of 1156 biliary tract cancer samples, 380 samples (33%) carried mutations in TP53. Several other genes, such as APC, have mutations in 4-8% of all samples. Thus, TP53 may be selected for inclusion in the panel based on a relatively high frequency in a population of biliary tract cancer samples.

A gene or region may be selected for a panel where the frequency of a tumor marker is significantly greater in sampled tumor tissue or circulating tumor DNA than found in a given background population. A combination of regions may be selected for inclusion of a panel such that at least a majority of subjects having a cancer will have a tumor marker present in at least one of the regions or genes in the panel. The combination of regions may be selected based on data indicating that, for a particular cancer or set of cancers, a majority of subjects have one or more tumor markers in one or more of the selected regions. For example, to detect cancer 1, a panel comprising regions A, B, C, and/or D may be selected based on data indicating that 90% of subjects with cancer 1 have a tumor marker in regions A, B, C, and/or D of the panel. Alternately, tumor markers may be shown to occur independently in two or more regions in subjects having a cancer such that, combined, a tumor marker in the two or more regions is present in a majority of a population of subjects having a cancer. For example, to detect cancer 2, a panel comprising regions X, Y, and Z may be selected based on data indicating that 90% of subjects have a tumor marker in one or more regions, and in 30% of such subjects a tumor marker is detected only in region X, while tumor markers are detected only in regions Y and/or Z for the remainder of the subjects for whom a tumor marker was detected. Tumor markers present in one or more regions previously shown to be associated with one or more cancers may be indicative of or predictive of a subject having cancer if a tumor marker is detected in one or more of those regions 50% or more of the time. Computational approaches such as models employing conditional probabilities of detecting cancer given a known cancer frequency for a set of tumor markers within one or more regions may be used to predict which regions, alone or in combination, may be predictive of cancer. Other approaches for panel selection involve the use of databases describing information from studies employing comprehensive genomic profiling of tumors with large panels and/or whole genome sequencing (WGS, RNA-seq, Chip-seq, bisulfate sequencing, ATAC-seq, and others). Information gleaned from literature may also describe pathways commonly affected and mutated in certain cancers. Panel selection may be further informed by the use of ontologies describing genetic information.

Genes included in the panel for sequencing can include the fully transcribed region, the promoter region, enhancer regions, regulatory elements, and/or downstream sequence. To further increase the likelihood of detecting tumor indicating mutations only exons may be included in the panel. The panel can comprise all exons of a selected gene, or only one or more of the exons of a selected gene. The panel may comprise of exons from each of a plurality of different genes. The panel may comprise at least one exon from each of the plurality of different genes.

In some aspects, a panel of exons from each of a plurality of different genes is selected such that a determined proportion of subjects having a cancer exhibit a genetic variant in at least one exon in the panel of exons.

At least one full exon from each different gene in a panel of genes may be sequenced. The sequenced panel may comprise exons from a plurality of genes. The panel may comprise exons from 2 to 100 different genes, from 2 to 70 genes, from 2 to 50 genes, from 2 to 30 genes, from 2 to 15 genes, or from 2 to 10 genes.

A selected panel may comprise a varying number of exons. The panel may comprise from 2 to 3000 exons. The panel may comprise from 2 to 1000 exons. The panel may comprise from 2 to 500 exons. The panel may comprise from 2 to 100 exons. The panel may comprise from 2 to 50 exons. The panel may comprise no more than 300 exons. The panel may comprise no more than 200 exons. The panel may comprise no more than 100 exons. The panel may comprise no more than 50 exons. The panel may comprise no more than 40 exons. The panel may comprise no more than 30 exons. The panel may comprise no more than 25 exons. The panel may comprise no more than 20 exons. The panel may comprise no more than 15 exons. The panel may comprise no more than 10 exons. The panel may comprise no more than 9 exons. The panel may comprise no more than 8 exons. The panel may comprise no more than 7 exons.

The panel may comprise one or more exons from a plurality of different genes. The panel may comprise one or more exons from each of a proportion of the plurality of different genes. The panel may comprise at least two exons from each of at least 25%, 50%, 75% or 90% of the different genes. The panel may comprise at least three exons from each of at least 25%, 50%, 75% or 90% of the different genes. The panel may comprise at least four exons from each of at least 25%, 50%, 75% or 90% of the different genes.

The sizes of the sequencing panel may vary. A sequencing panel may be made larger or smaller (in terms of nucleotide size) depending on several factors including, for example, the total amount of nucleotides sequenced or a number of unique molecules sequenced for a particular region in the panel. The sequencing panel can be sized 5 kb to 50 kb. The sequencing panel can be 10 kb to 30 kb in size. The sequencing panel can be 12 kb to 20 kb in size. The sequencing panel can be 12 kb to 60 kb in size. The sequencing panel can be at least 10 kb, 12 kb, 15 kb, 20 kb, 25 kb, 30 kb, 35 kb, 40 kb, 45 kb, 50 kb, 60 kb, 70 kb, 80 kb, 90 kb, 100 kb, 110 kb, 120 kb, 130 kb, 140 kb, or 150 kb in size. The sequencing panel may be less than 100 kb, 90 kb, 80 kb, 70 kb, 60 kb, or 50 kb in size.

The panel selected for sequencing can comprise at least 1, 5, 10, 15, 20, 25, 30, 40, 50, 60, 80, or 100 regions. In some cases, the regions in the panel are selected that the size of the regions are relatively small. In some cases, the regions in the panel have a size of about 10 kb or less, about 8 kb or less, about 6 kb or less, about 5 kb or less, about 4 kb or less, about 3 kb or less, about 2.5 kb or less, about 2 kb or less, about 1.5 kb or less, or about 1 kb or less or less. In some cases, the regions in the panel have a size from about 0.5 kb to about 10 kb, from about 0.5 kb to about 6 kb, from about 1 kb to about 11 kb, from about 1 kb to about 15 kb, from about 1 kb to about 20 kb, from about 0.1 kb to about 10 kb, or from about 0.2 kb to about 1 kb. For example, the regions in the panel can have a size from about 0.1 kb to about 5 kb.

The panel selected herein can allow for deep sequencing that is sufficient to detect low-frequency genetic variants (e.g., in cell-free nucleic acid molecules obtained from a sample). An amount of genetic variants in a sample may be referred to in terms of the minor allele frequency for a given genetic variant. The minor allele frequency may refer to the frequency at which minor alleles (e.g., not the most common allele) occurs in a given population of nucleic acids, such as a sample. Genetic variants at a low minor allele frequency may have a relatively low frequency of presence in a sample. In some cases, the panel allows for detection of genetic variants at a minor allele frequency of at least 0.0001%, 0.001%, 0.005%, 0.01%, 0.05%, 0.1%, or 0.5%. The panel can allow for detection of genetic variants at a minor allele frequency of 0.001% or greater. The panel can allow for detection of genetic variants at a minor allele frequency of 0.01% or greater. The panel can allow for detection of genetic variant present in a sample at a frequency of as low as 0.0001%, 0.001%, 0.005%, 0.01%, 0.025%, 0.05%, 0.075%, 0.1%, 0.25%, 0.5%, 0.75%, or 1.0%. The panel can allow for detection of tumor markers present in a sample at a frequency of at least 0.0001%, 0.001%, 0.005%, 0.01%, 0.025%, 0.05%, 0.075%, 0.1%, 0.25%, 0.5%, 0.75%, or 1.0%. The panel can allow for detection of tumor markers at a frequency in a sample as low as 1.0%. The panel can allow for detection of tumor markers at a frequency in a sample as low as 0.75%. The panel can allow for detection of tumor markers at a frequency in a sample as low as 0.5%. The panel can allow for detection of tumor markers at a frequency in a sample as low as 0.25%. The panel can allow for detection of tumor markers at a frequency in a sample as low as 0.1%. The panel can allow for detection of tumor markers at a frequency in a sample as low as 0.075%. The panel can allow for detection of tumor markers at a frequency in a sample as low as 0.05%. The panel can allow for detection of tumor markers at a frequency in a sample as low as 0.025%. The panel can allow for detection of tumor markers at a frequency in a sample as low as 0.01%. The panel can allow for detection of tumor markers at a frequency in a sample as low as 0.005%. The panel can allow for detection of tumor markers at a frequency in a sample as low as 0.001%. The panel can allow for detection of tumor markers at a frequency in a sample as low as 0.0001%. The panel can allow for detection of tumor markers in sequenced cfDNA at a frequency in a sample as low as 1.0% to 0.0001%. The panel can allow for detection of tumor markers in sequenced cfDNA at a frequency in a sample as low as 0.01% to 0.0001%.

A genetic variant can be exhibited in a percentage of a population of subjects who have a disease (e.g., cancer). In some cases, at least 1%, 2%, 3%, 5%, 10%, 20%, 30%, 40%, 50%, 60%, 70%, 80%, 90%, 95%, or 99% of a population having the cancer exhibit one or more genetic variants in at least one of the regions in the panel. For example, at least 80% of a population having the cancer may exhibit one or more genetic variants in at least one of the regions in the panel.

The panel can comprise one or more regions from each of one or more genes. In some cases, the panel can comprise one or more regions from each of at least 1, 2, 3, 4, 5, 6, 7, 8, 9, 10, 15, 20, 25, 30, 40, 50, or 80 genes. In some cases, the panel can comprise one or more regions from each of at most 1, 2, 3, 4, 5, 6, 7, 8, 9, 10, 15, 20, 25, 30, 40, 50, or 80 genes. In some cases, the panel can comprise one or more regions from each of from about 1 to about 80, from 1 to about 50, from about 3 to about 40, from 5 to about 30, from 10 to about 20 different genes.

The regions in the panel can be selected so that one or more epigenetically modified regions are detected. The one or more epigenetically modified regions can be acetylated, methylated, ubiquitylated, phosphorylated, sumoylated, ribosylated, and/or citrullinated. For example, the regions in the panel can be selected so that one or more methylated regions are detected.

The regions in the panel can be selected so that they comprise sequences differentially transcribed across one or more tissues. In some cases, the regions can comprise sequences transcribed in certain tissues at a higher level compared to other tissues. For example, the regions can comprise sequences transcribed in certain tissues but not in other tissues.

The regions in the panel can comprise coding and/or non-coding sequences. For example, the regions in the panel can comprise one or more sequences in exons, introns, promoters, 3' untranslated regions, 5' untranslated regions, regulatory elements, transcription start sites, and/or splice sites. In some cases, the regions in the panel can comprise other non-coding sequences, including pseudogenes, repeat sequences, transposons, viral elements, and telomeres. In some cases, the regions in the panel can comprise sequences in non-coding RNA, e.g., ribosomal RNA, transfer RNA, Piwi-interacting RNA, and microRNA.

The regions in the panel can be selected to detect (diagnose) a cancer with a desired level of sensitivity (e.g., through the detection of one or more genetic variants). For example, the regions in the panel can be selected to detect the cancer (e.g., through the detection of one or more genetic variants) with a sensitivity of at least 50%, 55%, 60%, 65%, 70%, 75%, 80%, 85%, 90%, 95%, 96%, 97%, 98%, 99%, 99.5%, or 99.9%. The regions in the panel can be selected to detect the cancer with a sensitivity of 100%.

The regions in the panel can be selected to detect (diagnose) a cancer with a desired level of specificity (e.g., through the detection of one or more genetic variants). For example, the regions in the panel can be selected to detect cancer (e.g., through the detection of one or more genetic variants) with a specificity of at least 50%, 55%, 60%, 65%, 70%, 75%, 80%, 85%, 90%, 95%, 96%, 97%, 98%, 99%, 99.5%, or 99.9%. The regions in the panel can be selected to detect the one or more genetic variant with a specificity of 100%.

The regions in the panel can be selected to detect (diagnose) a cancer with a desired positive predictive value. Positive predictive value can be increased by increasing sensitivity (e.g., chance of an actual positive being detected) and/or specificity (e.g., chance of not mistaking an actual negative for a positive). As a non-limiting example, regions in the panel can be selected to detect the one or more genetic variant with a positive predictive value of at least 50%, 55%, 60%, 65%, 70%, 75%, 80%, 85%, 90%, 95%, 96%, 97%, 98%, 99%, 99.5%, or 99.9%. The regions in the panel can be selected to detect the one or more genetic variant with a positive predictive value of 100%.

The regions in the panel can be selected to detect (diagnose) a cancer with a desired accuracy. As used herein, the term "accuracy" may refer to the ability of a test to discriminate between a disease condition (e.g., cancer) and health. Accuracy may be can be quantified using measures such as sensitivity and specificity, predictive values, likelihood ratios, the area under the ROC curve, Youden's index and/or diagnostic odds ratio.

Accuracy may presented as a percentage, which refers to a ratio between the number of tests giving a correct result and the total number of tests performed. The regions in the panel can be selected to detect cancer with an accuracy of at least 50%, 55%, 60%, 65%, 70%, 75%, 80%, 85%, 90%, 95%, 96%, 97%, 98%, 99%, 99.5%, or 99.9%. The regions in the panel can be selected to detect cancer with an accuracy of 100%.

A panel may be selected such that when one or more regions or genes in the panel are removed, specificity is appreciably decreased. Removal of one region from the panel may result in a decrease in specificity of at least 5%, 10%, 15%, 20%, 25%, 30%, 35%, 40%, 45%, 50%, or more.

A panel may be selected such that the addition of one or more regions or genes to the panel does not appreciably increase the specificity of the panel, e.g., does not increase the specificity by more than 1%, 2%, 5%, 10%, 15%, or 20%.

A panel may be of a size such that when one or more regions or genes in the panel are removed, this appreciably decreases sensitivity, e.g., sensitivity is decreased by at least 5%, 10%, 15%, 20%, 25%, 30%, 35%, 40%, 45%, 50%, or more.

A panel may be selected such that the addition of one or more regions or genes to the panel does not appreciably increase the sensitivity of the panel, e.g., does not increase the sensitivity by more than 1%, 2%, 5%, 10%, 15%, or 20%.

A panel may be of a size such that when one or more regions or genes in the panel are removed, accuracy is appreciably decreased, e.g., accuracy is decreased by at least 5%, 10%, 15%, 20%, 25%, 30%, 35%, 40%, 45%, 50%, or more.

A panel may be selected such that the addition of one or more regions or genes to the panel does not appreciably increase the accuracy of the panel, e.g., does not increase the accuracy by more than 1%, 2%, 5%, 10%, 15%, or 20%.

A panel may be of a size such that when one or more regions or genes the panel are removed, positive predictive value is appreciably decreased, e.g., positive predictive value is decreased by at least 5%, 10%, 15%, 20%, 25%, 30%, 35%, 40%, 45%, 50%, or more.

A panel may be selected such that the addition of one or more regions or genes to the panel does not appreciably increase the positive predictive value of the panel, e.g., does not increase the positive predictive value by more than 1%, 2%, 5%, 10%, 15%, or 20%

A panel may be selected to be highly sensitive and detect low frequency genetic variants. For instance, a panel may be selected such that a genetic variant or tumor marker present in a sample at a frequency as low as 0.01%, 0.05%, or 0.001% may be detected at a sensitivity of at least 50%, 55%, 60%, 65%, 70%, 75%, 80%, 85%, 90%, 95%, 96%, 97%, 98%, 99%, 99.5%, or 99.9%. Regions in a panel may be selected to detect a tumor marker present at a frequency of 1% or less in a sample with a sensitivity of 70% or greater. A panel may be selected to detect a tumor marker at a frequency in a sample as low as 0.1% with a sensitivity of at least 50%, 55%, 60%, 65%, 70%, 75%, 80%, 85%, 90%, 95%, 96%, 97%, 98%, 99%, 99.5%, or 99.9%. A panel may be selected to detect a tumor marker at a frequency in a sample as low as 0.01% with a sensitivity of at least 50%, 55%, 60%, 65%, 70%, 75%, 80%, 85%, 90%, 95%, 96%, 97%, 98%, 99%, 99.5%, or 99.9%. A panel may be selected to detect a tumor marker at a frequency in a sample as low as 0.001% with a sensitivity of at least 50%, 55%, 60%, 65%, 70%, 75%, 80%, 85%, 90%, 95%, 96%, 97%, 98%, 99%, 99.5%, or 99.9%.

A panel may be selected to be highly specific and detect low frequency genetic variants. For instance, a panel may be selected such that a genetic variant or tumor marker present in a sample at a frequency as low as 0.01%, 0.05%, or 0.001% may be detected at a specificity of at least 50%, 55%, 60%, 65%, 70%, 75%, 80%, 85%, 90%, 95%, 96%, 97%, 98%, 99%, 99.5%, or 99.9%. Regions in a panel may be selected to detect a tumor marker present at a frequency of 1% or less in a sample with a specificity of 70% or greater. A panel may be selected to detect a tumor marker at a frequency in a sample as low as 0.1% with a specificity of at least 70%, 75%, 80%, 85%, 90%, 95%, 96%, 97%, 98%, 99%, 99.5%, or 99.9%. A panel may be selected to detect a tumor marker at a frequency in a sample as low as 0.01% with a specificity of at least 70%, 75%, 80%, 85%, 90%, 95%, 96%, 97%, 98%, 99%, 99.5%, or 99.9%. A panel may be selected to detect a tumor marker at a frequency in a sample as low as 0.001% with a specificity of at least 70%, 75%, 80%, 85%, 90%, 95%, 96%, 97%, 98%, 99%, 99.5%, or 99.9%.

A panel may be selected to be highly accurate and detect low frequency genetic variants. A panel may be selected such that a genetic variant or tumor marker present in a sample at a frequency as low as 0.01%, 0.05%, or 0.001% may be detected at an accuracy of at least 70%, 75%, 80%, 85%, 90%, 95%, 96%, 97%, 98%, 99%, 99.5%, or 99.9%. Regions in a panel may be selected to detect a tumor marker present at a frequency of 1% or less in a sample with an accuracy of 70% or greater. A panel may be selected to detect a tumor marker at a frequency in a sample as low as 0.1% with an accuracy of at least 70%, 75%, 80%, 85%, 90%, 95%, 96%, 97%, 98%, 99%, 99.5%, or 99.9%. A panel may be selected to detect a tumor marker at a frequency in a sample as low as 0.01% with an accuracy of at least 70%, 75%, 80%, 85%, 90%, 95%, 96%, 97%, 98%, 99%, 99.5%, or 99.9%. A panel may be selected to detect a tumor marker at a frequency in a sample as low as 0.001% with an accuracy of at least 70%, 75%, 80%, 85%, 90%, 95%, 96%, 97%, 98%, 99%, 99.5%, or 99.9%.

A panel may be selected to be highly predictive and detect low frequency genetic variants. A panel may be selected such that a genetic variant or tumor marker present in a sample at a frequency as low as 0.01%, 0.05%, or 0.001% may have a positive predictive value of at least 70%, 75%, 80%, 85%, 90%, 95%, 96%, 97%, 98%, 99%, 99.5%, or 99.9%.

The concentration of probes or baits used in the panel may be increased (2 to 6 ng/µL) to capture more nucleic acid molecule within a sample. The concentration of probes or baits used in the panel may be at least 2 ng/µL, 3 ng/µL, 4 ng/µL, 5 ng/µL, 6 ng/µL, or greater. The concentration of probes may be about 2 ng/µL to about 3 ng/µL, about 2 ng/µL to about 4 ng/µL, about 2 ng/µL to about 5 ng/µL, about 2 ng/µL to about 6 ng/µL. The concentration of probes or baits used in the panel may be 2 ng/µL or more to 6 ng/µL or less. In some instances this may allow for more molecules within a biological to be analyzed thereby enabling lower frequency alleles to be detected.

Sequencing Depth

DNA enriched from a sample of cfDNA molecules may be sequenced at a variety of read depths to detect low frequency genetic variants in a sample. For a given position, read depth may refer to a number of all reads from all molecules from a sample that map to a position, including original molecules and molecules generated by amplifying original molecules. Thus, for example, a read depth of 50,000 reads can refer to the number of reads from 5,000 molecules, with 10 reads per molecule. Original molecules mapping to a position may be unique and non-redundant (e.g., non-amplified, sample cfDNA).

To assess read depth of sample molecules at a given position, sample molecules may be tracked. Molecular tracking techniques may comprise various techniques for labeling DNA molecules, such as barcode tagging, to uniquely identify DNA molecules in a sample. For example, one or more unique barcode sequences may be attached to one or more ends of a sample cfDNA molecule. In determining read depth at a given position, the number of distinct barcode tagged cfDNA molecules which map to that position can be indicative of the read depth for that position. In another example, both ends of sample cfDNA molecules may be tagged with one of eight barcode sequences. The read depth at a given position may be determined by quantifying the number of original cfDNA molecules at a given position, for instance, by collapsing reads that are redundant from amplification and identifying unique molecules based on the barcode tags and endogenous sequence information.

The DNA may be sequenced to a read depth of at least 3,000 reads per base, at least 4,000 reads per base, at least 5,000 reads per base, at least 6,000 reads per base, at least 7,000 reads per base, at least 8,000 reads per base, at least 9,000 reads per base, at least 10,000 reads per base, at least 15,000 reads per base, at least 20,000 reads per base, at least 25,000 reads per base, at least 30,000 reads per base, at least 40,000 reads per base, at least 50,000 reads per base, at least 60,000 reads per base, at least 70,000 reads per base, at least 80,000 reads per base, at least 90,000 reads per base, at least 100,000 reads per base, at least 110,000 reads per base, at least 120,000 reads per base, at least 130,000 reads per base, at least 140,000 reads per base, at least 150,000 reads per base, at least 160,000 reads per base, at least 170,000 reads per base, at least 180,000 reads per base, at least 190,000 reads per base, at least 200,000 reads per base, at least 250,000 reads per base, at least 500,000 reads per base, at least 1,000,000 reads per base, or at least 2,000,000 reads per base. The DNA may be sequenced to a read depth of about 3,000 reads per base, about 4,000 reads per base, about 5,000 reads per base, about 6,000 reads per base, about 7,000 reads per base, about 8,000 reads per base, about 9,000 reads per base, about 10,000 reads per base, about 15,000 reads per base, about 20,000 reads per base, about 25,000 reads per base, about 30,000 reads per base, about 40,000 reads per base, about 50,000 reads per base, about 60,000 reads per base, about 70,000 reads per base, about 80,000 reads per base, about 90,000 reads per base, about 100,000 reads per base, about 110,000 reads per base, about 120,000 reads per base, about 130,000 reads per base, about 140,000 reads per base, about 150,000 reads per base, about 160,000 reads per base, about 170,000 reads per base, about 180,000 reads per base, about 190,000 reads per base, about 200,000 reads per base, about 250,000 reads per base, about 500,000 reads per base, about 1,000,000 reads per base, or about 2,000,000 reads per base. The DNA can be sequenced to a read depth from about 10,000 to about 30,000 reads per base, 10,000 to about 50,000 reads per base, 10,000 to about 5,000,000 reads per base, 50,000 to about 3,000,000 reads per base, 100,000 to about 2,000,000 reads per base, or about 500,000 to about 1,000,000 reads per base. In some embodiments, DNA can be sequenced to any of the above read depths on a panel size selected from: less than 70,000 bases, less than 65,000 bases, less than 60,000 bases, less than 55,000 bases, less than 50,000 bases, less than 45,000 bases, less than 40,000 bases, less than 35,000 bases, less than 30,000 bases, less than 25,000 bases, less than 20,000 bases, less than 15,000 bases, less than 10,000 bases, less than 5,000 bases, and less than 1,000 bases. For example, the total number of reads for a panel can be as low as 600,000 (3,000 reads per base for 1,000 bases) and as high as $1.4 \times 10^{11}$ (2,000,000 reads per base for 70,000 bases). In some embodiments, DNA can be sequenced to any of the above read depths on a panel size selected from: 5,000 bases to 70,000 bases, 5,000 bases to 60,000 bases, 10,000 bases to 70,000 bases, or 10,000 bases to 70,000 bases.

Read coverage can include reads from one or both strands of a nucleic acid molecule. For example, read coverage may include reads from both strands of at least 5,000, at least 10,000, at least 15,000, at least 20,000, at least 25,000, at least 30,000, at least 35,000, at least 40,000, at least 45,000, or at least 50,000 DNA molecules from the sample mapping to each nucleotide in the of the panel.

A panel may be selected to optimize for a desired read depth given a fixed amount of base reads.

Tagging

In some embodiments of the present disclosure, a nucleic acid library is prepared prior to sequencing. For example, individual polynucleotide fragments in a genomic nucleic acid sample (e.g., genomic DNA sample) can be uniquely identified by tagging with non-unique identifiers, e.g., non-uniquely tagging the individual polynucleotide fragments. In some embodiments, nucleic acid molecules are non-uniquely tagged with respect to one another.

Polynucleotides disclosed herein can be tagged. For example, double-stranded polynucleotides can be tagged with duplex tags, tags that differently label the complementary strands (i.e., the "Watson" and "Crick" strands) of a double-stranded molecule. In some cases the duplex tags are polynucleotides having complementary and non-complementary portions.

Tags can be any types of molecules attached to a polynucleotide, including, but not limited to, nucleic acids, chemical compounds, florescent probes, or radioactive probes. Tags can also be oligonucleotides (e.g., DNA or RNA). Tags can comprise known sequences, unknown sequences, or both. A tag can comprise random sequences, pre-determined sequences, or both. A tag can be double-stranded or single-stranded. A double-stranded tag can be a duplex tag. A double-stranded tag can comprise two complementary strands. Alternatively, a double-stranded tag can comprise a hybridized portion and a non-hybridized portion. The double-stranded tag can be Y-shaped, e.g., the hybridized portion is at one end of the tag and the non-hybridized portion is at the opposite end of the tag. One such example is the "Y adapters" used in Illumina sequencing. Other examples include hairpin shaped adapters or bubble shaped adapters. Bubble shaped adapters have non-complementary sequences flanked on both sides by complementary sequences. In some embodiments, a Y-shaped adaptor comprises a barcode 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 nucleotides in length. In some combinations. This can be combined with blunt end repair and ligation.

The number of different tags may be greater than an estimated or predetermined number of molecules in the sample. For example, for unique tagging, at least two times as many different tags may be used as the estimated or predetermined number of molecules in the sample.

The number of different identifying tags used to tag molecules in a collection can range, for example, between any of 2, 3, 4, 5, 6, 7, 8, 9, 10, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49 at the low end of the range, and any of 50, 100, 500, 1000, 5000 and 10,000 at the high end of the range. The number of identifying tags used to tag molecules in a collection can be at least 2, 3, 4, 5, 6, 7, 8, 9, 10, 15, 20, 25, 30, 35, 40, 45, 50, 55, 60 or more. So, for example, a collection of from 100 billion to 1 trillion molecules can be tagged with from 4 to 100 different identifying tags. A collection of from 100 billion to 1 trillion molecules may be tagged with from 8 to 10,000 different identifying tags. A collection of from 100 billion to 1 trillion molecules may be tagged with from 16 to 10,000 different identifying tags. A collection of from 100 billion to 1 trillion molecules may be tagged with from 16 to 5,000 different identifying tags. A collection of from 100 billion to 1 trillion molecules may be tagged with from 16 to 1,000 different identifying tags.

A collection of molecules can be considered to be "non-uniquely tagged" if there are more molecules in the collection than tags. A collection of molecules can be considered to be non-uniquely tagged if each of at least 1%, at least 5%, at least 10%, at least 15%, at least 20%, at least 25%, at least 30%, at least 35%, at least 40%, at least 45%, or at least or about 50% of the molecules in the collection bears an identifying tag that is shared by at least one other molecule in the collection ("non-unique tag" or "non-unique identifier"). An identifier can comprise a single barcode or two barcodes. A population of nucleic acid molecules can be non-uniquely tagged by tagging the nucleic acid molecules with fewer tags than the total number of nucleic acid molecules in the population. For a non-uniquely tagged population, no more than 1%, 5%, 10%, 15%, 20%, 25%, 30%, 35%, 40%, 45%, or 50% of the molecules may be uniquely tagged. In some embodiments, nucleic acid molecules are identified by a combination of non-unique tags and the start and stop positions or sequences from sequence reads. In some embodiments, the number of nucleic acid molecules being sequenced is less than or equal to the number of combinations of identifiers and start and stop positions or sequences.

In some instances, the tags herein comprise molecular barcodes. Such molecular barcodes can be used to differentiate polynucleotides in a sample. Molecular barcodes can be different from one another. For example, molecular barcodes can have a difference between them that can be characterized by a predetermined edit distance or a Hamming distance. In some instances, the molecular barcodes herein have a minimum edit distance of 1, 2, 3, 4, 5, 6, 7, 8, 9, or 10. To further improve efficiency of conversion (e.g., tagging) of untagged molecular to tagged molecules, one utilizes short tags. For example, a library adapter tag can be up to 65, 60, 55, 50, 45, 40, or 35 nucleotide bases in length. A collection of such short library barcodes can include a number of different molecular barcodes, e.g., at least 2, 4, 6, 8, 10, 12, 14, 16, 18 or 20 different barcodes with a minimum edit distance of 1, 2, 3 or more.

Thus, a collection of molecules can include one or more tags. In some instances, some molecules in a collection can include an identifying tag ("identifier") such as a molecular barcode that is not shared by any other molecule in the collection. For example, in some instances of a collection of molecules, 100% or at least 50%, 60%, 70%, 80%, 90%, 95%, 97%, 98%, or 99% of the molecules in the collection can include an identifier or molecular barcode that is not shared by any other molecule in the collection. As used herein, a collection of molecules is considered to be "uniquely tagged" if each of at least 95% of the molecules in the collection bears an identifier that is not shared by any other molecule in the collection ("unique tag" or "unique identifier"). In some embodiments, nucleic acid molecules are uniquely tagged with respect to one another. A collection of molecules is considered to be "non-uniquely tagged" if each of at least 1%, 5%, 10%, 15%, 20%, 25%, 30%, 35%, 40%, 45%, or 50% of the molecules in the collection bears an identifying tag or molecular barcode that is shared by at least one other molecule in the collection ("non-unique tag" or "non-unique identifier"). In some embodiments, nucleic acid molecules are non-uniquely tagged with respect to one another. Accordingly, in a non-uniquely tagged population no more than 1% of the molecules are uniquely tagged. For example, in a non-uniquely tagged population, no more than 1%, 5%, 10%, 15%, 20%, 25%, 30%, 35%, 40%, 45%, or 50% of the molecules can be uniquely tagged.

A number of different tags can be used based on the estimated number of molecules in a sample. In some tagging methods, the number of different tags can be at least the same as the estimated number of molecules in the sample. In other tagging methods, the number of different tags can be at least two, three, four, five, six, seven, eight, nine, ten, one hundred or one thousand times as many as the estimated number of molecules in the sample. In unique tagging, at least two times (or more) as many different tags can be used as the estimated number of molecules in the sample.

The polynucleotides fragments (prior to tagging) can comprise sequences of any length. For example, polynucleotide fragments (prior to tagging) can comprise at least 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 400, 500, 600, 700, 800, 900, 1000, 1100, 1200, 1300, 1400, 1500, 1600, 1700, 1800, 1900, 2000 or more nucleotides in length. The polynucleotide fragment can be about the average length of cell-free DNA. For example, the polynucleotide fragments can comprise about 160 bases in length. The polynucleotide fragment can also be fragmented from a larger fragment into smaller fragments about 160 bases in length.

Improvements in sequencing can be achieved as long as at least some of the duplicate or cognate polynucleotides bear unique identifiers with respect to each other, that is, bear different tags. However, in certain embodiments, the number of tags used is selected so that there is at least a 95% chance that all duplicate molecules starting at any one position bear unique identifiers. For example, in a sample comprising about 10,000 haploid human genome equivalents of fragmented genomic DNA, e.g., cfDNA, z is expected to be between 2 and 8. Such a population can be tagged with between about 10 and 100 different identifiers, for example, about 2 identifiers, about 4 identifiers, about 9 identifiers, about 16 identifiers, about 25 identifiers, about 36 different identifiers, about 49 different identifiers, about 64 different identifiers, about 81 different identifiers, or about 100 different identifiers.

Nucleic acid barcodes having identifiable sequences, including molecular barcodes, can be used for tagging. For example, a plurality of DNA barcodes can comprise various numbers of sequences of nucleotides. A plurality of DNA barcodes having 2, 3, 4, 5, 6, 7, 8, 9, 10, 11, 12, 13, 14, 15, 16, 17, 18, 19, 20, 21, 22, 23, 24, 25, 26, 27, 28, 29, 30 or more identifiable sequences of nucleotides can be used. When attached to only one end of a polynucleotide, the plurality of DNA barcodes can produce 2, 3, 4, 5, 6, 7, 8, 9, 10, 11, 12, 13, 14, 15, 16, 17, 18, 19, 20, 21, 22, 23, 24, 25, 26, 27, 28, 29, 30 or more different identifiers. Alternatively, when attached to both ends of a polynucleotide, the plurality DNA barcodes can produce 4, 9, 16, 25, 36, 49, 64, 81, 100, 121, 144, 169, 196, 225, 256, 289, 324, 361, 400 or more different identifiers (which is the 2 of when the DNA barcode is attached to only 1 end of a polynucleotide). In one example, a plurality of DNA barcodes having 6, 7, 8, 9 or 10 identifiable sequences of nucleotides can be used. When attached to both ends of a polynucleotide, they produce 36, 49, 64, 81 or 100 possible different identifiers, respectively. In a particular example, the plurality of DNA barcodes can comprise 8 identifiable sequences of nucleotides. When attached to only one end of a polynucleotide, the plurality of DNA barcodes can produce 8 different identifiers. Alternatively, when attached to both ends of a polynucleotide, the plurality of DNA barcodes can produce 64 different identifiers. Samples tagged in such a way can be those with a range of about 10 ng to any of about 200 ng, about 1 µg, about 10 µg of fragmented polynucleotides, e.g., genomic DNA, e.g., cfDNA.

A polynucleotide can be uniquely identified in various ways. A polynucleotide can be uniquely identified by a unique barcode. For example, any two polynucleotides in a sample are attached two different barcodes. A barcode may be a DNA barcode or an RNA barcode. For example, a barcode may be a DNA barcode.

Alternatively, a polynucleotide can be uniquely identified by the combination of a barcode and one or more endogenous sequences of the polynucleotide. The barcode may be a non-unique tag or a unique tag. In some cases, the barcode is a non-unique tag. For example, any two polynucleotides in a sample can be attached to barcodes comprising the same barcode, but the two polynucleotides can still be identified by different endogenous sequences. The two polynucleotides may be identified by information in the different endogenous sequences. Such information includes the sequence of the endogenous sequences or a portion thereof, the length of the endogenous sequences, the location of the endogenous sequences, one or more epigenetic modification of the endogenous sequences, or any other feature of the endogenous sequences. In some embodiments, polynucleotides can be identified by an identifier (comprising one barcode or comprising two barcodes) in combination with start and stop sequences from the sequence read.

A combination of non-unique tags and endogenous sequence information may be used to unambiguously detect nucleic acid molecules. For instance, non-uniquely tagged nucleic acid molecules from a sample ("parent polynucleotides") may be amplified to generate progeny polynucleotides. The parent and progeny polynucleotides may then be sequenced to produce sequence reads. To reduce error, sequence reads may be collapsed to generate a set of consensus sequences. To generate consensus sequences, sequence reads may be collapsed based on sequence information in the non-unique tag and endogenous sequence information, including sequence information at a beginning region of a sequence read, sequence information at an end region of a sequence read, and a length of a sequence read. In some embodiments, a consensus sequence is generated by circular sequencing, in which the same nucleic acid strand is sequenced multiple times in a rolling circle to obtain the consensus sequence. A consensus sequence can be determined on a molecule-by-molecule basis (wherein a consensus sequence is determined over a stretch of bases) or a base-by-base basis (wherein a consensus nucleotide is determined for a base at a given position). In some embodiments, a probabilistic model is constructed to model amplification and sequencing error profiles and used to estimate probabilities of true nucleotide in each position of the molecule. In some embodiments, the probabilistic model parameter estimates are updated based on the error profiles observed in the individual sample or batch of samples being process together or a reference set of samples. In some embodiments, a consensus sequence is determined using barcodes that tag individual cfNA (e.g., cfDNA) molecules from a subject. In some embodiments, frequency of a nucleotide in a sample is determined by comparing it to frequency in a cohort of healthy individuals, a cohort of cancer patients, or germline DNA from the subject. In some embodiments, a cohort of cancer patients comprises a plurality of cancer patients with cancer that is early stage or late stage. In some embodiments, the cancer is metastatic or not metastatic. Types of cancer that an individual in a cohort of cancer patients may have been diagnosed with include, but are not limited to: carcinomas, sarcomas, lymphomas, leukemia's, germ cell tumors and blastomas. Types of cancer that a subject may have been diagnosed with include, but are not limited to: Acute lymphoblastic leukemia (ALL), Acute myeloid leukemia, Adrenocortical carcinoma, adult acute Myeloid leukemia, adult carcinoma of unknown primary site, adult malignant Mesothelioma, AIDS-related cancers, AIDS-related lymphoma, Anal cancer, Appendix cancer, Astrocytoma, childhood cerebellar or cerebral, Basal-cell carcinoma, Bile duct cancer, Bladder cancer, Bone tumor, osteosarcoma/malignant fibrous histiocytoma, Brain cancer, Brainstem glioma, Breast cancer, Bronchial adenomas/carcinoids, Burkitt Lymphoma, Carcinoid tumor, Carcinoma of unknown primary, Central nervous system lymphoma, cerebellar astrocytoma, cerebral astrocytoma/malignant glioma, Cervical cancer, childhood acute Myeloid leukemia, childhood cancer of unknown primary site, Childhood cancers, childhood cerebral astrocytoma, childhood Mesothelioma, Chondrosarcoma, Chronic lymphocytic leukemia, Chronic myelogenous leukemia, Chronic myeloproliferative disorders, Colon cancer, Cutaneous T-cell lymphoma, Desmoplastic small round cell tumor, Endometrial cancer, endometrial Uterine cancer, Ependymoma, Epitheliod Hemangioendothelioma (EHE), Esophageal cancer, Ewing family of tumors Sarcoma, Ewing's sarcoma in the Ewing family of tumors, Extracranial germ cell tumor, Extragonadal germ cell tumor, Extrahepatic bile duct cancer, Eye cancer, intraocular melanoma, Gallbladder cancer, Gastric (stomach) cancer, Gastric carcinoid, Gastrointestinal carcinoid tumor, Gastrointestinal stromal tumor (GIST), Gestational trophoblastic tumor, Glioma of the brain stem, Glioma, Hairy cell leukemia, Head and neck cancer, Heart cancer, Hepatocellular (liver) cancer, Hodgkin lymphoma, Hypopharyngeal cancer, Hypothalamic and visual pathway glioma, Islet cell carcinoma (endocrine pancreas), Kaposi sarcoma, Kidney cancer (renal cell cancer), Laryngeal cancer, Leukaemia, acute lymphoblastic (also called acute lymphocytic leukaemia), Leukaemia, acute myeloid (also called acute myelogenous leukemia), Leukaemia, chronic lymphocytic (also called chronic lymphocytic leukemia), Leukaemias, Leukemia, chronic myelogenous (also called chronic myeloid leukemia), Leukemia, hairy cell, Lip and oral cavity cancer, Liposarcoma, Liver cancer (primary), Lung cancer, non-small cell, Lung cancer, small cell, Lymphoma (AIDS-related), Lymphomas, Macroglobulinemia, Waldenström, Male breast cancer, Malignant fibrous histiocytoma of bone/osteosarcoma, medulloblastoma, Melanoma, Merkel cell cancer, Metastatic squamous neck cancer with occult primary, Mouth cancer, Multiple endocrine neoplasia syndrome, childhood, multiple Myeloma (cancer of the bone-marrow), Multiple myeloma/plasma cell neoplasm, Mycosis fungoides, Myelodysplastic syndromes, Myelodysplastic/myeloproliferative diseases, Myelogenous leukemia, chronic, Myxoma, Nasal cavity and paranasal sinus cancer, Nasopharyngeal carcinoma, Neuroblastoma, Non-Hodgkin Lymphomas, Non-small cell lung cancer, Oligodendroglioma, Oral cancer, Oropharyngeal cancer, Osteosarcoma/malignant fibrous histiocytoma of bone, Ovarian cancer, Ovarian epithelial cancer (surface epithelial-stromal tumor), Ovarian germ cell tumor, Ovarian low malignant potential tumor, Pancreatic cancer, Pancreatic cancer, islet cell, Paranasal sinus and nasal cavity cancer, Parathyroid cancer, Penile cancer, Pharyngeal cancer, Pheochromocytoma, Pineal astrocytoma, Pineal germinoma, Pineoblastoma and supratentorial primitive neuroectodermal tumors, Pituitary adenoma, Plasma cell neoplasia/Multiple myeloma, Pleuropulmonary blastoma, Primary central nervous system lymphoma, Prostate cancer, Rectal cancer, Renal cell carcinoma (kidney cancer), Renal pelvis and ureter transitional cell cancer, Retinoblastoma, Rhabdomyosarcoma, Salivary gland cancer, Sézary syndrome, Skin cancer (melanoma), Skin cancer (non-melanoma), Skin carcinoma, Merkel cell, Small cell lung cancer, Small intestine cancer, soft tissue Sarcoma, Squamous cell carcinoma, Squamous neck cancer with occult primary, metastatic, Stomach cancer, Supratentorial primitive neuroectodermal tumor, T-Cell lymphoma, cutaneous, Testicular cancer, Throat cancer, Thymoma and thymic carcinoma, Thymoma, Thyroid cancer, Transitional cell cancer of the renal pelvis and ureter, Ureter and renal pelvis, transitional cell cancer, Urethral cancer, Uterine sarcoma, Vaginal cancer, visual pathway and hypothalamic glioma, Visual pathway and hypothalamic glioma, childhood, Vulvar cancer, Waldenström macroglobulinemia, and Wilms tumor (kidney cancer).

The endogenous sequence can be on an end of a polynucleotide. For example, the endogenous sequence can be adjacent (e.g., base in between) to the attached barcode. In some instances the endogenous sequence can be at least 2, 4, 6, 8, 10, 20, 30, 40, 50, 60, 70, 80, 90, or 100 bases in length. The endogenous sequence can be a terminal sequence of the fragment/polynucleotides to be analyzed. The endogenous sequence may be the length of the sequence. For example, a plurality of barcodes comprising 8 different barcodes can be attached to both ends of each polynucleotide in a sample. Each polynucleotide in the sample can be identified by the combination of the barcodes and about 10 base pair endogenous sequence on an end of the polynucleotide. Without being bound by theory, the endogenous sequence of a polynucleotide can also be the entire polynucleotide sequence.

Also disclosed herein are compositions of tagged polynucleotides. The tagged polynucleotide can be single-stranded. Alternatively, the tagged polynucleotide can be double-stranded (e.g., duplex-tagged polynucleotides). Accordingly, this disclosure also provides compositions of duplex-tagged polynucleotides. The polynucleotides can comprise any types of nucleic acids (DNA and/or RNA). The polynucleotides comprise any types of DNA disclosed herein. For example, the polynucleotides can comprise DNA, e.g., fragmented DNA or cfDNA. A set of polynucleotides in the composition that map to a mappable base position in a genome can be non-uniquely tagged, that is, the number of different identifiers can be at least 2 and fewer than the number of polynucleotides that map to the mappable base position. The number of different identifiers can also be at least 3, 4, 5, 6, 7, 8, 9, 10, 11, 12, 13, 14, 15, 16, 17, 18, 19, 20, 21, 22, 23, 24, 25 and fewer than the number of polynucleotides that map to the mappable base position.

In some instances, as a composition goes from about 1 ng to about 10 µg or higher, a larger set of different molecular barcodes can be used. For example, between 5 and 100 different library adaptors can be used to tag polynucleotides in a cfDNA sample.

The molecular barcodes can be assigned to any types of polynucleotides disclosed in this disclosure. For example, the molecular barcodes can be assigned to cell-free polynucleotides (e.g., cfDNA). Often, an identifier disclosed herein can be a barcode oligonucleotide that is used to tag the polynucleotide. The barcode identifier may be a nucleic acid oligonucleotide (e.g., a DNA oligonucleotide). The barcode identifier can be single-stranded. Alternatively, the barcode identifier can be double-stranded. The barcode identifier can be attached to polynucleotides using any method disclosed herein. For example, the barcode identifier can be attached to the polynucleotide by ligation using an enzyme. The barcode identifier can also be incorporated into the polynucleotide through PCR. In other cases, the reaction may comprise addition of a metal isotope, either directly to the analyte or by a probe labeled with the isotope. Generally, assignment of unique or non-unique identifiers or molecular barcodes in reactions of this disclosure may follow methods and systems described by, for example, U.S. patent applications 2001/0053519, 2003/0152490, 2011/0160078 and U.S. Pat. No. 6,582,908, each of which is entirely incorporated herein by reference.

Identifiers or molecular barcodes used herein may be completely endogenous whereby circular ligation of individual fragments may be performed followed by random shearing or targeted amplification. In this case, the combination of a new start and stop point of the molecule and the original intramolecular ligation point can form a specific identifier.

Identifiers or molecular barcodes used herein can comprise any types of oligonucleotides. In some cases, identifiers may be predetermined, random, or semi-random sequence oligonucleotides. Identifiers can be barcodes. For example, a plurality of barcodes may be used such that barcodes are not necessarily unique to one another in the plurality. Alternatively, a plurality of barcodes may be used such that each barcode is unique to any other barcode in the plurality. The barcodes can comprise specific sequences (e.g., predetermined sequences) that can be individually tracked. Further, barcodes may be attached (e.g., by ligation) to individual molecules such that the combination of the barcode and the sequence it may be ligated to creates a specific sequence that may be individually tracked. As described herein, detection of barcodes in combination with sequence data of beginning (start) and/or end (stop) portions of sequence reads can allow assignment of a unique identity to a particular molecule. The length or number of base pairs of an individual sequence read may also be used to assign a unique identity to such a molecule. As described herein, fragments from a single strand of nucleic acid having been assigned a unique identity, may thereby permit subsequent identification of fragments from the parent strand. In this way the polynucleotides in the sample can be uniquely or substantially uniquely tagged. A duplex tag can include a degenerate or semi-degenerate nucleotide sequence, e.g., a random degenerate sequence. The nucleotide sequence can comprise any number of nucleotides. For example, the nucleotide sequence can comprise 1 (if using a non-natural nucleotide), 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more nucleotides. In a particular example, the sequence can comprise 7 nucleotides. In another example, the sequence can comprise 8 nucleotides. The sequence can also comprise 9 nucleotides. The sequence can comprise 10 nucleotides.

A barcode can comprise contiguous or non-contiguous sequences. A barcode that comprises at least 1, 2, 3, 4, 5 or more nucleotides is a contiguous sequence or non-contiguous sequence. if the 4 nucleotides are uninterrupted by any other nucleotide. For example, if a barcode comprises the sequence TTGC, a barcode is contiguous if the barcode is TTGC. On the other hand, a barcode is non-contiguous if the barcode is TTXGC, where X is a nucleic acid base.

An identifier or molecular barcode can have an n-mer sequence which may be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more nucleotides in length. A tag herein can comprise any range of nucleotides in length. For example, the sequence can be between 2 to 100, 10 to 90, 20 to 80, 30 to 70, 40 to 60, or about 50 nucleotides in length. A population of barcodes can comprise barcodes of the same length or of different lengths.

The tag can comprise a double-stranded fixed reference sequence downstream of the identifier or molecular barcode. Alternatively, the tag can comprise a double-stranded fixed reference sequence upstream or downstream of the identifier or molecular barcode. Each strand of a double-stranded fixed reference sequence can be, for example, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 nucleotides in length.

Tagging disclosed herein can be performed using any method. A polynucleotide can be tagged with an adaptor by hybridization. For example, the adaptor can have a nucleotide sequence that is complementary to at least a portion of a sequence of the polynucleotide. As an alternative, a polynucleotide can be tagged with an adaptor by ligation.

The barcodes or tags can be attached using a variety of techniques. Attachment can be performed by methods including, for example, ligation (blunt-end or sticky-end) or annealing-optimized molecular-inversion probes. For example, tagging can comprise using one or more enzymes. The enzyme can be a ligase. The ligase can be a DNA ligase. For example, the DNA ligase can be a T4 DNA ligase, *E. coli* DNA ligase, and/or mammalian ligase. The mammalian ligase can be DNA ligase I, DNA ligase III, or DNA ligase IV. The ligase can also be a thermostable ligase. Tags can be ligated to a blunt-end of a polynucleotide (blunt-end ligation). Alternatively, tags can be ligated to a sticky end of a polynucleotide (sticky-end ligation). Efficiency of ligation can be increased by optimizing various conditions. Efficiency of ligation can be increased by optimizing the reaction time of ligation. For example, the reaction time of ligation can be less than 1, 2, 3, 4, 5, 6, 7, 8, 9, 10, 11, 12, 13, 14, 15, 16, 17, 18, 19, or 20 hours. In a particular example, reaction time of ligation is less than 20 hours. Efficiency of ligation can be increased by optimizing the ligase concentration in the reaction. For example, the ligase concentration can be at least 10, 50, 100, 150, 200, 250, 300, 400, 500, or 600 units/microliter. Efficiency can also be optimized by adding or varying the concentration of an enzyme suitable for ligation, enzyme cofactors or other additives, and/or optimizing a temperature of a solution having the enzyme. Efficiency can also be optimized by varying the addition order of various components of the reaction. The end of tag sequence can comprise dinucleotide to increase ligation efficiency. When the tag comprises a non-complementary portion (e.g., Y-shaped adaptor), the sequence on the complementary portion of the tag adaptor can comprise one or more selected sequences that promote ligation efficiency. Such sequences are located at the terminal end of the tag. Such sequences can comprise 1, 2, 3, 4, 5, or 6 terminal bases. Reaction solution with high viscosity (e.g., a low Reynolds number) can also be used to increase ligation efficiency. For example, solution can have a Reynolds number less than 3000, 2000, 1000, 900, 800, 700, 600, 500, 400, 300, 200, 100, 50, 25, or 10. It is also contemplated that roughly unified distribution of fragments (e.g., tight standard deviation) can be used to increase ligation efficiency. For example, the variation in fragment sizes can vary by less than 20%, 15%, 10%, 5%, or 1%. Tagging can also comprise primer extension, for example, by polymerase chain reaction (PCR). Tagging can also comprise any of ligation-based PCR, multiplex PCR, single strand ligation, or single strand circularization. Efficiency of tagging (e.g., by ligation) can be increased to an efficiency of tagging molecules (conversion efficiency) of at least 20%, at least 30%, at least 40%, at least 50%, at least 60%, at least 70%, at least 80%, at least 90%, at least 95%, or at least 98%.

A ligation reaction may be performed in which parent polynucleotides in a sample are admixed with a reaction mixture comprising y different barcode oligonucleotides, wherein y=a square root of n. The ligation can result in the random attachment of barcode oligonucleotides to parent polynucleotides in the sample. The reaction mixture can then be incubated under ligation conditions sufficient to effect ligation of barcode oligonucleotides to parent polynucleotides of the sample. In some embodiments, random barcodes selected from the y different barcode oligonucleotides are ligated to both ends of parent polynucleotides. Random ligation of the y barcodes to one or both ends of the parent polynucleotides can result in production of $y^2$ unique identifiers. For example, a sample comprising about 10,000 haploid human genome equivalents of cfDNA can be tagged with about 36 unique identifiers. The unique identifiers can comprise six unique DNA barcodes. Ligation of 6 unique barcodes to both ends of a polynucleotide can result in 36 possible unique identifiers produced.

In some embodiments, a sample comprising about 10,000 haploid human genome equivalents of DNA is tagged with a number of unique identifiers produced by ligation of a set of unique barcodes to both ends of parent polynucleotides. For example, 64 unique identifiers can be produced by ligation of 8 unique barcodes to both ends of parent polynucleotides. Likewise, 100 unique identifiers can be produced by ligation of 10 unique barcodes to both ends of parent polynucleotides, 225 unique identifiers can be produced by ligation of 15 unique barcodes to both ends of parent polynucleotides, 400 unique identifiers can be produced by ligation of 20 unique barcodes to both ends of parent polynucleotides, 625 unique identifiers can be produced by ligation of 25 unique barcodes to both ends of parent polynucleotides, 900 unique identifiers can be produced by ligation of 30 unique barcodes to both ends of parent polynucleotides, 1225 unique identifiers can be produced by ligation of 35 unique barcodes to both ends of parent polynucleotides, 1600 unique identifiers can be produced by ligation of 40 unique barcodes to both ends of parent polynucleotides, 2025 unique identifiers can be produced by ligation of 45 unique barcodes to both ends of parent polynucleotides, and 2500 unique identifiers can be produced by ligation of 50 unique barcodes to both ends of parent polynucleotides. The ligation efficiency of the reaction can be over 10%, over 20%, over 30%, over 40%, over 50%, over 60%, over 70%, over 80%, or over 90%. The ligation conditions can comprise use of bi-directional adaptors that can bind either end of the fragment and still be amplifiable. The ligation conditions can comprise sticky-end ligation adapters each having an overhang of at least one nucleotide base. In some instances, the ligation conditions can comprise adapters having different base overhangs to increase ligation efficiency. As a non-limiting example, the ligation conditions may comprise adapters with single-base cytosine (C) overhangs (i.e., C-tailed adaptors), single-base thymine (T) overhangs (T-tailed adaptors), single-base adenine (A) overhangs (A-tailed adaptors), and/or single-base guanine (G) overhangs (G-tailed adaptors). The ligation conditions can comprise blunt end ligation, as opposed to tailing. The ligation conditions can comprise careful titration of an amount of adapter and/or barcode oligonucleotides. The ligation conditions can comprise the use of over 2×, over 5×, over 10×, over 20×, over 40×, over 60×, over 80×, (e.g., ~100×) molar excess of adapterand/or barcode oligonucleotides as compared to an amount of parent polynucleotide fragments in the reaction mixture. The ligation conditions can comprise use of a T4 DNA ligase (e.g., NEBNExt Ultra Ligation Module). In an example, 18 microliters of ligase master mix is used with 90 microliter ligation (18 parts of the 90) and ligation enhancer. Accordingly, tagging parent polynucleotides with n unique identifiers can comprise use of a number y different barcodes, wherein y=a square root of n. Samples tagged in such a way can be those with a range of about 10 ng to any of about 100 ng, about 200 ng, about 300 ng, about 400 ng, about 500 ng, about 1 or about 10 μg of fragmented polynucleotides, e.g., genomic DNA, e.g. cfDNA. The number y of barcodes used to identify parent polynucleotides in a sample can depend on the amount of nucleic acid in the sample.

One method of increasing conversion efficiency involves using a ligase engineered for optimal reactivity on single-stranded DNA, such as a ThermoPhage single-stranded DNA (ssDNA) ligase derivative. Such ligases bypass traditional steps in library preparation of end-repair and A-tailing that can have poor efficiencies and/or accumulated losses due to intermediate cleanup steps, and allows for twice the probability that either the sense or anti-sense starting polynucleotide will be converted into an appropriately tagged polynucleotide. It also converts double-stranded polynucleotides that may possess overhangs that may not be sufficiently blunt-ended by the typical end-repair reaction. Optimal reactions conditions for this ssDNA reaction are: 1× reaction buffer (50 millimolar (mM) MOPS (pH 7.5), 1 mM DTT, 5 mM MgCl2, 10 mM KCl). With 50 mM ATP, 25 mg/ml BSA, 2.5 mM MnCl2, 200 pmol 85 nt ssDNA oligomer and 5 U ssDNA ligase incubated at 65° C. for 1 hour. Subsequent amplification using PCR can further convert the tagged single-stranded library to a double-stranded library and yield an overall conversion efficiency of well above 20%. Other methods of increasing conversion rate, e.g., to above 10%, include, for example, any of the following, alone or in combination: annealing-optimized molecular-inversion probes, blunt-end ligation with a well-controlled polynucleotide size range, selection of a high-efficiency polymerase, sticky-end ligation or an upfront multiplex amplification step with or without the use of fusion primers, optimization of end bases in a target sequence, optimization of reaction conditions (including reaction time), and the introduction of one or more steps to clean up a reaction (e.g., of unwanted nucleic acid fragments) during the ligation, and optimization of temperature of buffer conditions. Sticky end ligation may be performed using multiple-nucleotide overhangs. Sticky end ligation may be performed using single-nucleotide overhangs comprising an A, T, C, or G bases.

The present disclosure also provides compositions of tagged polynucleotides. The polynucleotides can comprise fragmented DNA, e.g. cfDNA. A set of polynucleotides in the composition that map to a mappable base position in a genome can be non-uniquely tagged, that is, the number of different identifiers can be at least at least 2 and fewer than the number of polynucleotides that map to the mappable base position. A composition of between about 10 ng to about 10 μg (e.g., any of about 10 ng-1 μg, about 10 ng-100 ng, about 100 ng-10 μg, about 100 ng-1 μg, about 1 μg-10 μg) can bear between any of 2, 5, 10, 50 or 100 to any of 100, 1000, 10,000 or 100,000 different identifiers. For example, between 5 and 100 different identifiers can be used to tag the polynucleotides in such a composition.

Sequencing

Tagged polynucleotides can be sequenced to generate sequence reads. For example, a tagged duplex polynucleotide can be sequenced. Sequence reads can be generated from only one strand of a tagged duplex polynucleotide. Alternatively, both strands of a tagged duplex polynucleotide can generate sequence reads. The two strands of the tagged duplex polynucleotide can comprise the same tags. Alternatively, the two strands of the tagged duplex polynucleotide can comprise different tags. When the two strands of the tagged duplex polynucleotide are differently tagged, sequence reads generated from one strand (e.g., a Watson strand) can be distinguished from sequence reads generated from the other strands (e.g., a Crick strand). Sequencing can involve generating multiple sequence reads for each molecule. This occurs, for example, as a result the amplification of individual polynucleotide strands during the sequencing process, e.g., by PCR.

Methods disclosed herein can comprise amplifying of polynucleotides. Amplification can be performed before tagging, after tagging, or both. Polynucleotides amplification can result in the incorporation of nucleotides into a nucleic acid molecule or primer thereby forming a new nucleic acid molecule complementary to a template nucleic acid. The newly formed polynucleotide molecule and its template can be used as templates to synthesize additional polynucleotides. The polynucleotides being amplified can be any nucleic acids, for example, deoxyribonucleic acids, including genomic DNAs, cDNAs (complementary DNA), cfDNAs, and circulating tumor DNAs (ctDNAs). The polynucleotides being amplified can also be RNAs. As used herein, one amplification reaction may comprise many rounds of DNA replication. DNA amplification reactions can include, for example, polymerase chain reaction (PCR). One PCR reaction may comprise 2-100 "cycles" of denaturation, annealing, and synthesis of a DNA molecule. For example, 2-7, 5-10, 6-11, 7-12, 8-13, 9-14, 10-15, 11-16, 12-17, 13-18, 14-19, or 15-20 cycles can be performed during the amplification step. The condition of the PCR can be optimized based on the GC content of the sequences, including the primers. Amplification primers can be chosen to select for a target sequence of interest. Primers can be designed to optimize or maximize conversion efficiency. In some embodiments, primers contain a short sequence between the primers so as to pull out a small region of interest. In some embodiments, primers target nucleosomal regions so that the primers hybridize to areas where nucleosomes are present, as opposed to areas between nucleosomes, because internucleosomal areas are more highly cleaved and therefore less likely to be present as targets.

In some embodiments, regions of the genome are targeted that are differentially protected by nucleosomes and other regulatory mechanisms in cancer cells, the tumor microenvironment, or immune system components (granulocytes, tumor infiltrating lymphocytes, etc). In some embodiments, other regions are targeted that are stable and/or not differentially regulated in tumor cells. Within these regions, differences in coverage, cleavage sites, fragment length, sequence content, sequence content at fragment endpoints, or sequence content of the nearby genomic context can be used to infer the presence or absence of a certain classification of cancer cells (e.g., EGFR mutant, KRAS mutant, ERBb2 amplified, or PD-1 expression cancers), or type of cancer (e.g., lung adenocarcinoma, breast, or colorectal cancer). Such targeting can also enhance the sensitivity and/or specificity of the assay by enhancing coverage at certain sites or the probability of capture. These principles apply to methods of targeting including, but not limited to, ligation plus hybrid capture-based enrichment, amplification-based enrichment, rolling circle-based enrichment with sequence/genomic location specific initiation primers, and other methods. The regions that can be targeted with such methods and subsequent analysis include, but are not limited to, intronic regions, exonic regions, promoter regions, TSS regions, distant regulatory elements, enhancer regions, and super-enhancer regions and/or junctions of the preceding. These methods can also be used to infer the tissue of origin of the tumor and/or a measure of tumor burden in combination with other techniques described herein for determining variants (e.g., germline or somatic variants) contained within the sample. For example, germline variants can determine predisposition for certain types of cancer, while somatic variants can correlate to certain types of cancer specifically based on the affected genes, pathways and percentages of the variants. This information can then be used in combination with epigenetic signatures relating to regulatory mechanisms and/or chemical modifications such as, for example, methylation, hydroxymethylation, acetylation, and/or RNA. The nucleic acid library can involve combined analysis of DNA, DNA modifications and RNA to enhance sensitivity and specificity to the detection of cancer, type of cancer, molecular pathways activated in the specific disease, tissue of origin as well as a measure that corresponds to tumor burden. Approaches for analyzing each of the above have been outlined elsewhere and can be combined for analysis of a single or multiple samples from the same patient, whereby the sample can be derived from various bodily specimens.

Nucleic acid amplification techniques can be used with the assays described herein. Some amplification techniques are the PCR methodologies which can include, but are not limited to, solution PCR and in situ PCR. For example, amplification may comprise PCR-based amplification. Alternatively, amplification may comprise non PCR-based amplification. Amplification of the template nucleic acid may comprise use of one or more polymerases. For example, the polymerase may be a DNA polymerase or an RNA polymerase. In some cases, high fidelity amplification is performed such as with the use of high fidelity polymerase (e.g., Phusion RTM High-Fidelity DNA Polymerase) or PCR protocols. In some cases, the polymerase may be a high fidelity polymerase. For example, the polymerase may be KAPA HiFi DNA polymerase. The polymerase may also be Phusion DNA polymerase or an Ultra II polymerase. The polymerase may be used under reaction conditions that reduce or minimize amplification biases, e.g., due to fragment length and/or GC content.

Amplification of a single strand of a polynucleotide by PCR will generate copies both of that strand and its complement. During sequencing, both the strand and its complement will generate sequence reads. However, sequence reads generated from the complement of, for example, the Watson strand, can be identified as such because they bear the complement of the portion of the duplex tag that tagged the original Watson strand. In contrast, a sequence read generated from a Crick strand or its amplification product will bear the portion of the duplex tag that tagged the original Crick strand. In this way, a sequence read generated from an amplified product of a complement of the Watson strand can be distinguished from a complement sequence read generated from an amplification product of the Crick strand of the original molecule.

Amplification, such as PCR amplification, is typically performed in rounds. Exemplary rounds of amplification include 1, 2, 3, 4, 5, 6, 7, 8, 9, 10, 11, 12, 13, 14, 15, 16, 17, 18, 19, 20, 25, 30, or more rounds of amplification. Amplification conditions can be optimized, for example, for buffer conditions and polymerase type and conditions. The amplification also can be modified to reduce bias in the sample processing, for example, by reducing non-specific amplification bias, GC content bias, and size bias.

In some embodiments, sequences can be enriched prior to sequencing. Enrichment can be performed for specific target regions or nonspecifically. In some embodiments, targeted genomic regions of interest may be enriched with capture probes ("baits") selected for one or more bait set panels using a differential tiling and capture scheme. A differential tiling and capture scheme uses bait sets of different relative concentrations to differentially tile (e.g., at different "resolutions") across genomic regions associated with baits, subject to a set of constraints (e.g., sequencer constraints such as sequencing load, utility of each bait, etc.), and capture them at a desired level for downstream sequencing. These targeted genomic regions of interest may include single-nucleotide variants (SNVs) and indels (i.e., insertions or deletions). The targeted genomic regions of interest may comprise backbone genomic regions of interest ("backbone regions") or hot-spot genomic regions of interest ("hot-spot regions" or "hotspot regions" or "hot-spots" or "hotspots"). While "hotpots" can refer to particular loci associated with sequence variants, "backbone" regions can refer to larger genomic regions, each of which can have one or more potential sequence variants. For example, a backbone region can be a region containing one or more cancer-associated mutations, while a hotspot can be a locus with a particular mutation associated with recurring cancer or a locus with a particular recurring mutation associated with cancer. Both backbone and hot-spot genomic regions of interest may comprise tumor-relevant marker genes commonly included in liquid biopsy assays (e.g., BRAF, BRCA 1/2, EGFR, KRAS, PIK3CA, ROS1, TP53, and others), for which one or more variants may be expected to be seen in subjects with cancer. In some embodiments, biotin-labeled beads with probes to one or more regions of interest can be used to capture target sequences, optionally followed by amplification of those regions, to enrich for the regions of interest.

The amount of sequencing data that can be obtained from a sample is finite, and constrained by such factors as the quality of nucleic acid templates, number of target sequences, scarcity of specific sequences, limitations in sequencing techniques, and practical considerations such as time and expense. Thus, a "read budget" is a way to conceptualize the amount of genetic information that can be extracted from a sample. A per-sample read budget can be selected that identifies the total number of base reads to be allocated to a test sample comprising a predetermined amount of DNA in a sequencing experiment. The read budget can be based on total reads produced, e.g., including redundant reads produced through amplification. Alternatively, it can be based on number of unique molecules detected in the sample. In certain embodiments read budget can reflect the amount of double-stranded support for a call at a locus. That is, the percentage of loci for which reads from both strands of a DNA molecule are detected.

Factors of a read budget include read depth and panel length. For example, a read budget of 3,000,000,000 reads can be allocated as 150,000 bases at an average read depth of 20,000 reads/base. Read depth can refer to number of molecules producing a read at a locus. In the present disclosure, the reads at each base can be allocated between bases in the backbone region of the panel, at a first average read depth and bases in the hotspot region of the panel, at a deeper read depth. In some embodiments, a sample is sequenced to a read depth determined by the amount of nucleic acid present in a sample. In some embodiments, a sample is sequenced to a set read depth, such that samples comprising different amounts of nucleic acid are sequenced to the same read depth. For example, a sample comprising 300 ng of nucleic acids can be sequenced to a read depth 1/10 that of a sample comprising 30 ng of nucleic acids. In some embodiments, nucleic acids from two or more different subjects can be added together at a ratio based on the amount of nucleic acids obtained from each of the subjects.

By way of non-limiting example, if a read budget consists of 100,000 read counts for a given sample, those 100,000 read counts will be divided between reads of backbone regions and reads of hotspot regions. Allocating a large number of those reads (e.g., 90,000 reads) to backbone regions will result in a small number of reads (e.g., the remaining 10,000 reads) being allocated to hotspot regions. Conversely, allocating a large number of reads (e.g., 90,000 reads) to hotspot regions will result in a small number of reads (e.g., the remaining 10,000 reads) being allocated to backbone regions. Thus, a skilled worker can allocate a read budget to provide desired levels of sensitivity and specificity. In certain embodiments, the read budget can be between 100,000,000 reads and 100,000,000,000 reads, e.g., between 500,000,000 reads and 50,000,000,000 reads, or between about 1,000,000,000 reads and 5,000,000,000 reads across, for example, 20,000 bases to 100,000 bases.

All polynucleotides (e.g., amplified polynucleotides) can be submitted to a sequencing device for sequencing. Alternatively, a sampling, or subset, of all of the amplified polynucleotides is submitted to a sequencing device for sequencing. With respect to any original double-stranded polynucleotide there can be three results with respect to sequencing. First, sequence reads can be generated from both complementary strands of the original molecule (that is, from both the Watson strand and from the Crick strand). Second, sequence reads can be generated from only one of the two complementary strands (that is, either from the Watson strand or from the Crick strand, but not both). Third, no sequence read may be generated from either of the two complementary strands. Consequently, counting unique sequence reads mapping to a genetic locus will underestimate the number of double-stranded polynucleotides in the original sample mapping to the locus. Described herein are methods of estimating the unseen and uncounted polynucleotides.

The sequencing method can be massively parallel sequencing, that is, simultaneously (or in rapid succession) sequencing any of at least 100, 1000, 10,000, 100,000, 1 million, 10 million, 100 million, or 1 billion polynucleotide molecules.

Sequencing methods may include, but are not limited to: high-throughput sequencing, pyrosequencing, sequencing-by-synthesis, single-molecule sequencing, nanopore sequencing, semiconductor sequencing, sequencing-by-ligation, sequencing-by-hybridization, RNA-Seq (Illumina), Digital Gene Expression (Helicos), Next generation sequencing, Single Molecule Sequencing by Synthesis (SMSS) (Helicos), massively-parallel sequencing, Clonal Single Molecule Array (Solexa), shotgun sequencing, Maxam-Gilbert or Sanger sequencing, primer walking, sequencing using PacBio, SOLiD, Ion Torrent, or Nanopore platforms and any other sequencing methods known in the art.

The method can comprise sequencing at least 1 million, 10 million, 100 million, 500 million, 1 billion, 1.1 billion, 1.2 billion, 1.5 billion, 2 billion, 2.5 billion, 3 billion, 3.5 billion, 4 billion, 4.5 billion, 5 billion, 5.5 billion, 6 billion, 6.5 billion, 7 billion, 8 billion, 9 billion or 10 billion base pairs. In some cases, the methods can comprise sequencing from about 1 billion to about 7 billion, from about 1.1 billion to about 6.8 billion, from about 1.2 billion, to about 6.5 billion, from about 1.1 billion to about 6.4 billion, from about 1.5 billion to about 7 billion, from about 2 billion to about 6 billion, from about 2.5 billion to about 5.5 billion, from about 3 billion to about 5 billion base pairs. For example, the methods can comprise sequencing from about 1.2 billion, to about 6.5 billion base pairs.

Tumor Markers

A tumor marker is a genetic variant associated with one or more cancers. Tumor markers may be determined using any of several resources or methods. A tumor marker may have been previously discovered or may be discovered de novo using experimental or epidemiological techniques. Detection of a tumor marker may be indicative of cancer when the tumor marker is highly correlated a cancer. Detection of a tumor marker may be indicative of cancer when a tumor marker in a region or gene occur with a frequency that is greater than a frequency for a given background population or dataset.

Publicly available resources such as scientific literature and databases may describe in detail genetic variants found to be associated with cancer. Scientific literature may describe experiments or genome-wide association studies (GWAS) associating one or more genetic variants with cancer. Databases may aggregate information gleaned from sources such as scientific literature to provide a more comprehensive resource for determining one or more tumor markers. Non-limiting examples of databases include FANTOM, GTex, GEO, Body Atlas, INSiGHT, OMIM (Online Mendelian Inheritance in Man, omim.org), cBioPortal (cbioportal.org), CIViC (Clinical Interpretations of Variants in Cancer, civic.genome.wustl.edu), DOCM (Database of Curated Mutations, docm.genome.wustl.edu), and ICGC Data Portal (dcc.icgc.org). In a further example, the COSMIC (Catalogue of Somatic Mutations in Cancer) database allows for searching of tumor markers by cancer, gene, or mutation type. Tumor markers may also be determined de novo by conducting experiments such as case control or association (e.g, genome-wide association studies) studies.

One or more tumor markers may be detected in the sequencing panel. A tumor marker may be one or more genetic variants associated with cancer. Tumor markers can be selected from single nucleotide variants (SNVs), copy number variants (CNVs), insertions or deletions (e.g., indels), gene fusions and inversions. Tumor markers may affect the level of a protein. Tumor markers may be in a promoter or enhancer, and may alter the transcription of a gene. The tumor markers may affect the transcription and/or translation efficacy of a gene. The tumor markers may affect the stability of a transcribed mRNA. The tumor marker may result in a change to the amino acid sequence of a translated protein. The tumor marker may affect splicing, may change the amino acid coded by a particular codon, may result in a frameshift, or may result in a premature stop codon. The tumor marker may result in a conservative substitution of an amino acid. One or more tumor markers may result in a conservative substitution of an amino acid. One or more tumor markers may result in a nonconservative substitution of an amino acid.

One or more of the tumor markers may be a driver mutation. A driver mutation is a mutation that gives a selective advantage to a tumor cell in its microenvironment, through either increasing its survival or reproduction. None of the tumor markers may be a driver mutation. One or more of the tumor markers may be a passenger mutation. A passenger mutation is a mutation that has no effect on the fitness of a tumor cell but may be associated with a clonal expansion because it occurs in the same genome with a driver mutation.

The frequency of a tumor marker may be as low as 0.001%. The frequency of a tumor marker may be as low as 0.005%. The frequency of a tumor marker may be as low as 0.01%. The frequency of a tumor marker may be as low as 0.02%. The frequency of a tumor marker may be as low as 0.03%. The frequency of a tumor marker may be as low as 0.05%. The frequency of a tumor marker may be as low as 0.1%. The frequency of a tumor marker may be as low as 1%.

No single tumor marker may be present in more than 50%, of subjects having the cancer. No single tumor marker may be present in more than 40%, of subjects having the cancer. No single tumor marker may be present in more than 30%, of subjects having the cancer. No single tumor marker may be present in more than 20%, of subjects having the cancer. No single tumor marker may be present in more than 10%, of subjects having the cancer. No single tumor marker may be present in more than 5%, of subjects having the cancer. A single tumor marker may be present in 0.001% to 50% of subjects having cancer. A single tumor marker may be present in 0.01% to 50% of subjects having cancer. A single tumor marker may be present in 0.01% to 30% of subjects having cancer. A single tumor marker may be present in 0.01% to 20% of subjects having cancer. A single tumor marker may be present in 0.01% to 10% of subjects having cancer. A single tumor marker may be present in 0.1% to 10% of subjects having cancer. A single tumor marker may be present in 0.1% to 5% of subjects having cancer.

Detection of a tumor marker may indicate the presence of one or more cancers. Detection may indicate presence of a cancer selected from the group comprising ovarian cancer, pancreatic cancer, breast cancer, colorectal cancer, non-small cell lung carcinoma (e.g., squamous cell carcinoma, or adenocarcinoma) or any other cancer. Detection may indicate the presence of any cancer selected from the group comprising ovarian cancer, pancreatic cancer, breast cancer, colorectal cancer, non-small cell lung carcinoma (squamous cell or adenocarcinoma) or any other cancer. Detection may indicate the presence of any of a plurality of cancers selected from the group comprising ovarian cancer, pancreatic cancer, breast cancer, colorectal cancer and non-small cell lung carcinoma (squamous cell or adenocarcinoma), or any other cancer. Detection may indicate presence of one or more of any of the cancers mentioned in this application.

One or more cancers may exhibit a tumor marker in at least one exon in the panel. One or more cancers selected from the group comprising ovarian cancer, pancreatic cancer, breast cancer, colorectal cancer, non-small cell lung carcinoma (squamous cell or adenocarcinoma), or any other cancer, each exhibit a tumor marker in at least one exon in the panel. Each of at least 3 of the cancers may exhibit a tumor marker in at least one exon in the panel. Each of at least 4 of the cancers may exhibit a tumor marker in at least one exon in the panel. Each of at least 5 of the cancers may exhibit a tumor marker in at least one exon in the panel. Each of at least 8 of the cancers may exhibit a tumor marker in at least one exon in the panel. Each of at least 10 of the cancers may exhibit a tumor marker in at least one exon in the panel. All of the cancers may exhibit a tumor marker in at least one exon in the panel.

If a subject has a cancer, the subject may exhibit a tumor marker in at least one exon or gene in the panel. At least 85% of subjects having a cancer may exhibit a tumor marker in at least one exon or gene in the panel. At least 90%, of subjects having a cancer may exhibit a tumor marker in at least one exon or gene in the panel. At least 92% of subjects having a cancer may exhibit a tumor marker in at least one exon or gene in the panel. At least 95% of subjects having a cancer may exhibit a tumor marker in at least one exon or gene in the panel. At least 96% of subjects having a cancer may exhibit a tumor marker in at least one exon or gene in the panel. At least 97% of subjects having a cancer may exhibit a tumor marker in at least one exon or gene in the panel. At least 98% of subjects having a cancer may exhibit a tumor marker in at least one exon or gene in the panel. At least 99% of subjects having a cancer may exhibit a tumor marker in at least one exon or gene in the panel. At least 99.5% of subjects having a cancer may exhibit a tumor marker in at least one exon or gene in the panel.

If a subject has a cancer, the subject may exhibit a tumor marker in at least one region in the panel. At least 85% of subjects having a cancer may exhibit a tumor marker in at least one region in the panel. At least 90%, of subjects having a cancer may exhibit a tumor marker in at least one region in the panel. At least 92% of subjects having a cancer may exhibit a tumor marker in at least one region in the panel. At least 95% of subjects having a cancer may exhibit a tumor marker in at least one region in the panel. At least 96% of subjects having a cancer may exhibit a tumor marker in at least one region in the panel. At least 97% of subjects having a cancer may exhibit a tumor marker in at least one region in the panel. At least 98% of subjects having a cancer may exhibit a tumor marker in at least one region in the panel. At least 99% of subjects having a cancer may exhibit a tumor marker in at least one region in the panel. At least 99.5% of subjects having a cancer may exhibit a tumor marker in at least one region in the panel.

Detection may be performed with a high sensitivity and/or a high specificity. Sensitivity can refer to a measure of the proportion of positives that are correctly identified as such. In some cases, sensitivity refers to the percentage of all existing tumor markers that are detected. In some cases, sensitivity refers to the percentage of sick people who are correctly identified as having certain disease. Specificity can refer to a measure of the proportion of negatives that are correctly identified as such. In some cases, specificity refers to the proportion of unaltered bases which are correctly identified. In some cases, specificity refers to the percentage of healthy people who are correctly identified as not having certain disease. The non-unique tagging method described previously significantly increases specificity of detection by reducing noise generated by amplification and sequencing errors, which reduces frequency of false positives. Detection may be performed with a sensitivity of at least 95%, 97%, 98%, 99%, 99.5%, or 99.9% and/or a specificity of at least 80%, 90%, 95%, 97%, 98% or 99%. Detection may be performed with a sensitivity of at least 90%, 95%, 97%, 98%, 99%, 99.5%, 99.6%, 99.98%, 99.9% or 99.95%. Detection may be performed with a specificity of at least 90%, 95%, 97%, 98%, 99%, 99.5%, 99.6%, 99.98%, 99.9% or 99.95%. Detection may be performed with a specificity of at least 70% and a sensitivity of at least 70%, a specificity of at least 75% and a sensitivity of at least 75%, a specificity of at least 80% and a sensitivity of at least 80%, a specificity of at least 85% and a sensitivity of at least 85%, a specificity of at least 90% and a sensitivity of at least 90%, a specificity of at least 95% and a sensitivity of at least 95%, a specificity of at least 96% and a sensitivity of at least 96%, a specificity of at least 97% and a sensitivity of at least 97%, a specificity of at least 98% and a sensitivity of at least 98%, a specificity of at least 99% and a sensitivity of at least 99%, or a specificity of 100% a sensitivity of 100%. In some cases, the methods can detect a tumor marker at a sensitivity of sensitivity of about 80% or greater. In some cases, the methods can detect a tumor marker at a sensitivity of sensitivity of about 95% or greater. In some cases, the methods can detect a tumor marker at a sensitivity of sensitivity of about 80% or greater, and a sensitivity of sensitivity of about 95% or greater.

Detection may be highly accurate. Accuracy may apply to the identification of tumor markers in cell free DNA, and/or to the diagnosis of cancer. Statistical tools, such as co-variate analysis described above, may be used to increase and/or measure accuracy. The methods can detect a tumor marker at an accuracy of at least 80%, 90%, 95%, 97%, 98% or 99%, 99.5%, 99.6%, 99.98%, 99.9%, or 99.95%. In some cases, the methods can detect a tumor marker at an accuracy of at least 95% or greater.

Detection Limit/Noise Range

Noise can be introduced through errors in copying and/or reading a polynucleotide. For example, in a sequencing process, a single polynucleotide can first be subject to amplification. Amplification can introduce errors, so that a subset of the amplified polynucleotides may contain, at a particular locus, a base that is not the same as the original base at that locus. Furthermore, in the reading process a base at any particular locus may be read incorrectly. As a consequence, the collection of sequence reads can include a certain percentage of base calls at a locus that are not the same as the original base. In typical sequencing technologies this error rate can be in the single digits, e.g., 2%-3%. In some instances, the error rate can be up to about 10%, up to about 9%, up to about 8%, up to about 7%, up to about 6%, up to about 5%, up to about 4%, up to about 3%, up to about 2%, or up to about 1%. When a collection of molecules that are all presumed to have the same sequence are sequenced, this noise may be sufficiently small that one can identify the original base with high reliability.

However, if a collection of parent polynucleotides includes a subset of polynucleotides that vary at a particular locus, noise can be a significant problem. This can be the case, for example, when cell-free DNA includes not only germline DNA, but DNA from another source, such as fetal DNA or DNA from a cancer cell. In this case, if the frequency of molecules with sequence variants may be in the same range as the frequency of errors introduced by the sequencing process, then true sequence variants may not be distinguishable from noise. This may interfere, for example, with detecting sequence variants in a sample. For example, sequences can have a per-base error rate of 0.5-1%. Amplification bias and sequencing errors introduce noise into the final sequencing product. This noise can diminish sensitivity of detection. As a non-limiting example, sequence variants whose frequency is less than the sequencing error rate can be mistaken for noise.

A noise range or detection limit refers to instances where the frequency of molecules with sequence variants is in the same range as the frequency of errors introduced by the sequencing process. A "detection limit" may also refer to instances where too few variant-carrying molecules are sequenced for the variant to be detected. The frequency of molecules with sequence variants may be in the same range as the frequency of errors as a result of a small amount of nucleic acid molecules. As a non-limiting example, a sampled amount of nucleic acids, e.g. 100 ng, may contain a relatively small number of cell-free nucleic acid molecules, e.g. circulating tumor DNA molecules, such that the frequency of a sequence variant may be low, even though the variant may be present in a majority of circulating tumor DNA molecules. Alternately, the sequence variant may be rare or occur in only a very small amount of the sampled nucleic acids such that a detected variant is indistinguishable from noise and/or sequencing error. As a non-limiting example, at a particular locus, a tumor marker may only be detected in 0.1% to 5% of all reads at that locus.

Distortion can be manifested in the sequencing process as a difference in signal strength, e.g., total number of sequence reads, produced by molecules in a parent population at the same frequency. Distortion can be introduced, for example, through amplification bias, GC bias, or sequencing bias. This may interfere with detecting copy number variation in a sample. GC bias results in the uneven representation of areas rich or poor in GC content in the sequence reading. Also, by providing reads of sequences in greater or less amounts than their actual number in a population, amplification bias can distort measurements of copy number variation.

One way to reduce noise and/or distortion from a single individual molecule or from an ensemble of molecules is to group sequence reads into families derived from original individual molecules to reduce noise and/or distortion from a single individual molecule or from an ensemble of molecules. Efficient conversion of individual polynucleotides in a sample of initial genetic material into sequence-ready tagged parent polynucleotides may increase the probability that individual polynucleotides in a sample of initial genetic material will be represented in a sequence-ready sample. This can produce sequence information about more polynucleotides in the initial sample. Additionally, high yield generation of consensus sequences for tagged parent polynucleotides by high-rate sampling of progeny polynucleotides amplified from the tagged parent polynucleotides, and collapsing of generated sequence reads into consensus sequences representing sequences of parent tagged polynucleotides can reduce noise introduced by amplification bias and/or sequencing errors, and can increase sensitivity of detection. Collapsing sequence reads into a consensus sequence is one way to reduce noise in the received message from one molecule. Using probabilistic functions that convert received frequencies into likelihood or posterior estimates of each of the possible true nucleotides using defined estimates of amplification and sequencing error profiles is another way to reduce noise and/or distortion. With respect to an ensemble of molecules, grouping reads into families and determining a quantitative measure of the families reduces distortion, for example, in the quantity of molecules at each of a plurality of different loci. Again, collapsing sequence reads of different families into consensus sequences eliminate errors introduced by amplification and/or sequencing error. Furthermore, determining frequencies of base calls based on probabilities derived from family information also reduces noise in the received message from an ensemble of molecules. Frequency reporting or tumor marker calls also can be made using a plurality of reference sequences and coverage observations, from which a frequency for observing a tumor marker at a position will be determined. Reference sequences can comprise sequences or marker profiles from healthy individuals or from individuals having a disease or condition, such as cancer. A frequency from "known" reference samples can be used to set a threshold frequency for making a marker detection call. For example, a frequency of 0.1% for a nucleotide having an "A" at a certain position can be used as a threshold for determining whether or not to call a base at that position "A" in a test subject. For example, at least 20, at least 50, at least 100, at least 500, at least 1,000, at least 2,000, at least 3,000, at least 4,000, at least 5,000, at least 6,000, at least 7,000, at least 8,000, at least 9,000, at least 10,000, at least 11,000, at least 12,000, at least 13,000, at least 14,000, at least 15,000, at least 16,000, at least 17,000, at least 18,000, at least 19,000, at least 20,000, at least 30,000, at least 40,000, at least 50,000, at least 60,000, at least 70,000, at least 80,000, at least 90,000, or at least 100,000 reference sequences can be used.

Noise and/or distortion may be further reduced by identifying contaminating molecules from other processed samples by comparing molecule tagging and location information to a collection of observed molecules within the sample being processed or across batches of samples. Noise and/or distortion may be further reduced by comparing genetic variations in a sequence read with genetic variations other sequence reads. A genetic variation observed in one sequence read and again in other sequence reads increases the probability that a detected variant is in fact a tumor marker and not merely a sequencing error or noise. As a non-limiting example, if a genetic variation is observed in a first sequence read and also observed in a second sequence read, a Bayesian inference may be made regarding whether the variation is in fact a genetic variation and not a sequencing error.

Repeated detection of a variant may increase the probability, likelihood, and/or confidence that a variant is accurately detected. A variant can be repeatedly detected by comparing two or more sets of genetic data or genetic variations. The two or more sets of genetic variations can be detected in both samples at multiple time points and different samples at the same time point (for example a re-analyzed blood sample). In detecting a variant in the noise range or below the noise threshold, the re-sampling or repeated detection of a low frequency variant makes it more likely that the variant is in fact a variant and not a sequencing error. Re-sampling can be from the same sample, such as a sample that is re-analyzed or re-run, or from samples at different time points.

Co-variate detection may increase the probability, likelihood, and/or confidence that a variant is accurately detected. For co-variate tumor markers, the presence of one tumor marker is associated with the presence of one or more other tumor markers. Based on the detection of a co-variate genetic variation, it may be possible to infer the presence of an associated co-variate genetic variation, even where the associated genetic variation is present below a detection limit. Alternately, based on the detection of a co-variate genetic variation, the diagnostic confidence indication for the associated genetic variation may be increased. Further, in some instances where a co-variate variant is detected, a detection threshold for a co-variate variant detected below a detection limit may be decreased. Non-limiting examples of co-variate variations or genes include: driver mutations and resistance mutations, driver mutations and passenger mutations. As specific example of co-variants or genes is EGFR L858R activating mutation and EGFR T790M resistance mutation, found in lung cancers. Numerous other co-variate variants and genes are associated with various resistance mutations and will be recognized by one having skill in the art.

In one implementation, using measurements from a plurality of samples collected substantially at once or over a plurality of time points, the diagnostic confidence indication for each variant can be adjusted to indicate a confidence of predicting the observation of the copy number variation (CNV) or mutation or tumor marker. The confidence can be increased by using measurements at a plurality of time points to determine whether cancer is advancing, in remission or stabilized. The diagnostic confidence indication can be assigned by any of a number of statistical methods and can be based, at least in part, on the frequency at which the measurements are observed over a period of time. For example, a statistical correlation of current and prior results can be done. Alternatively, for each diagnosis, a hidden Markov model can be built, such that a maximum likelihood or maximum a posteriori decision can be made based on the frequency of occurrence of a particular test event from a plurality of measurements or a time points. As part of this model, the probability of error and resultant diagnostic confidence indication for a particular decision can be output as well. In this manner, the measurements of a parameter, whether or not they are in the noise range, may be provided with a confidence interval. Tested over time, one can increase the predictive confidence of whether a cancer is advancing, stabilized or in remission by comparing confidence intervals over time. Two sampling time points can be separated by at least about 1 microsecond, 1 millisecond, 1 second, 10 seconds, 30 seconds, 1 minute, 10 minutes, 30 minutes, 1 hour, 12 hours, 1 day, 1 week, 2 weeks, 3 weeks, one month, or one year. Two time points can be separated by about a month to about a year, about a year to about 5 years, or no more than about three months, two months, one month, three weeks, two weeks, one week, one day, or twelve hours. In some embodiments, two time points can be separated by a therapeutic event such as the administration of a treatment or the performance of a surgical procedure. When the two time points are separated by the therapeutic event, CNV or mutations detected can be compared before and after the event.

After sequencing data of cell free polynucleotide sequences is collected, one or more bioinformatics processes may be applied to the sequence data to detect genetic features or variations such as cfDNA characteristics at regulatory elements, nucleosomal spacing/nucleosome binding patterns, chemical modifications of nucleic acids, copy number variation, and mutations or changes in epigenetic markers, including but not limited to methylation profiles, and genetic variants such as SNVs, CNVs, indels, and/or fusions. In some cases, in which copy number variation analysis is desired, sequence data may be: 1) aligned with a reference genome and mapped to individual molecules; 2) filtered; 4) partitioned into windows or bins of a sequence; 5) coverage reads and molecules counted for each window; 6) coverage molecules can then be normalized using a statistical modeling algorithm; and 7) an output file can be generated reflecting discrete copy number states at various positions in the genome. In some cases, the number of coverage reads/molecules or normalized coverage reads aligning to a particular locus of the reference genome is counted. In other cases, in which mutation analysis is desired, sequence data may be 1) aligned with a reference genome and mapped to individual molecules; 2) filtered; 4) frequency of variant bases calculated based on coverage reads for that specific base; 5) variant base frequency normalized using a stochastic, statistical or probabilistic modeling algorithm; and 6) an output file can be generated reflecting mutation states at various positions in the genome. In some cases, identifiers (such as those including barcodes) can be used to group sequence reads during mutation analysis. In some cases, sequence reads are grouped into families, e.g., by using identifiers or a combination of identifiers and start/stop positions or sequences. In some cases, a base call can be made by comparing nucleotides in one or more families to a reference sequence and determining the frequency of a particular base 1) within each family, and 2) between the families and the reference sequences. A nucleotide base call can be made based on criteria such as the percentage of families having a base at a position. In some cases, a base call is reported if its frequency is greater than a noise threshold as determined by frequency in a plurality of reference sequences (e.g., sequences from healthy individuals). Temporal information from the current and prior analysis of the patient or subject is used to enhance the analysis and determination. In some embodiments, sequence information from the patient or subject is compared to sequence information obtained from a cohort of healthy individuals, a cohort of cancer patients, or germline DNA from the patient or subject. Germline DNA can be obtained, without limitation, from bodily fluid, whole blood, platelets, serum, plasma, stool, red blood cells, white blood cells or leukocytes, endothelial cells, tissue biopsies, synovial fluid, lymphatic fluid, ascites fluid, interstitial or extracellular fluid, the fluid in spaces between cells, including gingival crevicular fluid, bone marrow, cerebrospinal fluid, saliva, mucous, sputum, semen, sweat, urine, or any other bodily fluids. A cohort of cancer patients can have the same type of cancer as the patient or subject, the same stage of cancer as the patient or subject, both, or neither. In some embodiments, a cohort of cancer patients, a cohort of healthy individuals, or germline DNA from the subject is used to provide a baseline frequency of a base at a position, and the baseline frequency is used in making a base call in the subject. Without limitation, a frequency for a base at a position in a cohort of healthy individuals, or germline DNA from the subject can be compared to the frequency of a base detected among sequence reads from the subject.

In some embodiments, the methods and systems of the present disclosure can be used to detect a minor allele frequency (MAF) of 0.025% or lower, 0.05% or lower, 0.075% or lower, or 0.1% or lower. Copy number variation can be measured as a ratio of (1) unique molecule counts (UMCs) for a gene in a test sample to (2) UMCs for that gene in a reference sample (e.g., control sample). In some embodiments, the methods and systems of the present disclosure can be used to detect a copy number variation that is a copy number amplification (CNA). In some embodiments, the methods and systems of the present disclosure can be used to detect a CNA of at least 1.5, 2, 3, 4, 5, 6, 7, 8, 9, 10, 11, 12, 13, 14, 15, 16, 17, 18, 19, 20, 25, 30, 35, 40, 45, 50, 55, 60, or more. In some embodiments, the methods and systems of the present disclosure can be used to detect a copy number variation that is a copy number loss (CNL). In some embodiments, the methods and systems of the present disclosure can be used to detect a CNL of less than 0.9, 0.8, 0.7, 0.6, 0.5, 0.4, 0.3, 0.2, 0.1, or 0.05.

A variety of different reactions and/operations may occur within the systems and methods disclosed herein, including but not limited to: nucleic acid sequencing, nucleic acid quantification, sequencing optimization, detecting gene expression, quantifying gene expression, genomic profiling, cancer profiling, or analysis of expressed markers. Moreover, the systems and methods have numerous medical applications. For example, it may be used for the identification, detection, diagnosis, treatment, monitoring, staging of, or risk prediction of various genetic and non-genetic diseases and disorders including cancer. It may be used to assess subject response to different treatments of the genetic and non-genetic diseases, or provide information regarding disease progression and prognosis.

Computer Control Systems

The present disclosure provides computer control systems that are programmed to implement methods of the disclosure. FIG. 1 shows a computer system 901 that is programmed or otherwise configured to analyze sequencing data, detect tumor markers and determine cancer status. The computer system 901 can regulate various aspects of sequence analysis of the present disclosure, such as, for example, matching data against known sequences and variants. The computer system 901 can be an electronic device of a user or a computer system that is remotely located with respect to the electronic device. The electronic device can be a mobile electronic device.

The computer system 901 includes a central processing unit (CPU, also "processor" and "computer processor" herein) 905, which can be a single core or multi core processor, or a plurality of processors for parallel processing. The computer system 901 also includes memory or memory location 910 (e.g., random-access memory, read-only memory, flash memory), electronic storage unit 915 (e.g., hard disk), communication interface 920 (e.g., network adapter) for communicating with one or more other systems, and peripheral devices 925, such as cache, other memory, data storage and/or electronic display adapters. The memory 910, storage unit 915, interface 920 and peripheral devices 925 are in communication with the CPU 905 through a communication bus (solid lines), such as a motherboard. The storage unit 915 can be a data storage unit (or data repository) for storing data. The computer system 901 can be operatively coupled to a computer network ("network") 930 with the aid of the communication interface 920. The network 930 can be the Internet, an internet and/or extranet, or an intranet and/or extranet that is in communication with the Internet. The network 930 in some cases is a telecommunication and/or data network. The network 930 can include one or more computer servers, which can enable distributed computing, such as cloud computing. The network 930, in some cases with the aid of the computer system 901, can implement a peer-to-peer network, which may enable devices coupled to the computer system 901 to behave as a client or a server.

The CPU 905 can execute a sequence of machine-readable instructions, which can be embodied in a program or software. The instructions may be stored in a memory location, such as the memory 910. The instructions can be directed to the CPU 905, which can subsequently program or otherwise configure. The CPU 905 to implement methods of the present disclosure. Examples of operations performed by the CPU 905 can include fetch, decode, execute, and writeback.

The CPU 905 can be part of a circuit, such as an integrated circuit. One or more other components of the system 901 can be included in the circuit. In some cases, the circuit is an application specific integrated circuit (ASIC).

The storage unit 915 can store files, such as drivers, libraries and saved programs. The storage unit 915 can store user data, e.g., user preferences and user programs. The computer system 901 in some cases can include one or more additional data storage units that are external to the computer system 901, such as located on a remote server that is in communication with the computer system 901 through an intranet or the Internet.

The computer system 901 can communicate with one or more remote computer systems through the network 930. For instance, the computer system 901 can communicate with a remote computer system of a user (e.g., a physician). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 901 via the network 930.

Methods as described herein can be implemented by way of machine (e.g., computer processor) executable code stored on an electronic storage location of the computer system 901, such as, for example, on the memory 910 or electronic storage unit 915. The machine executable or machine readable code can be provided in the form of software. During use, the code can be executed by the processor 905. In some cases, the code can be retrieved from the storage unit 915 and stored on the memory 910 for ready access by the processor 905. In some situations, the electronic storage unit 915 can be precluded, and machine-executable instructions are stored on memory 910.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 901, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semi-conductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 901 can include or be in communication with an electronic display 935 that comprises a user interface (UI) 940 for providing, for example, information about cancer diagnosis. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 905. The algorithm can, for example, determine whether a cancer is present and/or progressing.

EXAMPLES

Example 1

Next Generation Sequencing Assay for Detection of ctDNA in Early Stage Cancer Patients A 12 kb gene panel was applied to a clinical study involving 20 early stage (II/III) and 1 stage IV CRC patients with both pre- and intra-op/follow-up blood draws at two sites, University of California, San Francisco (UCSF) and Samsung Medical Center (SMC). A subset (12 patients) also had tumor samples collected at the time of the surgery. FIG. 1 depicts an example of the study design.

Figure 2:
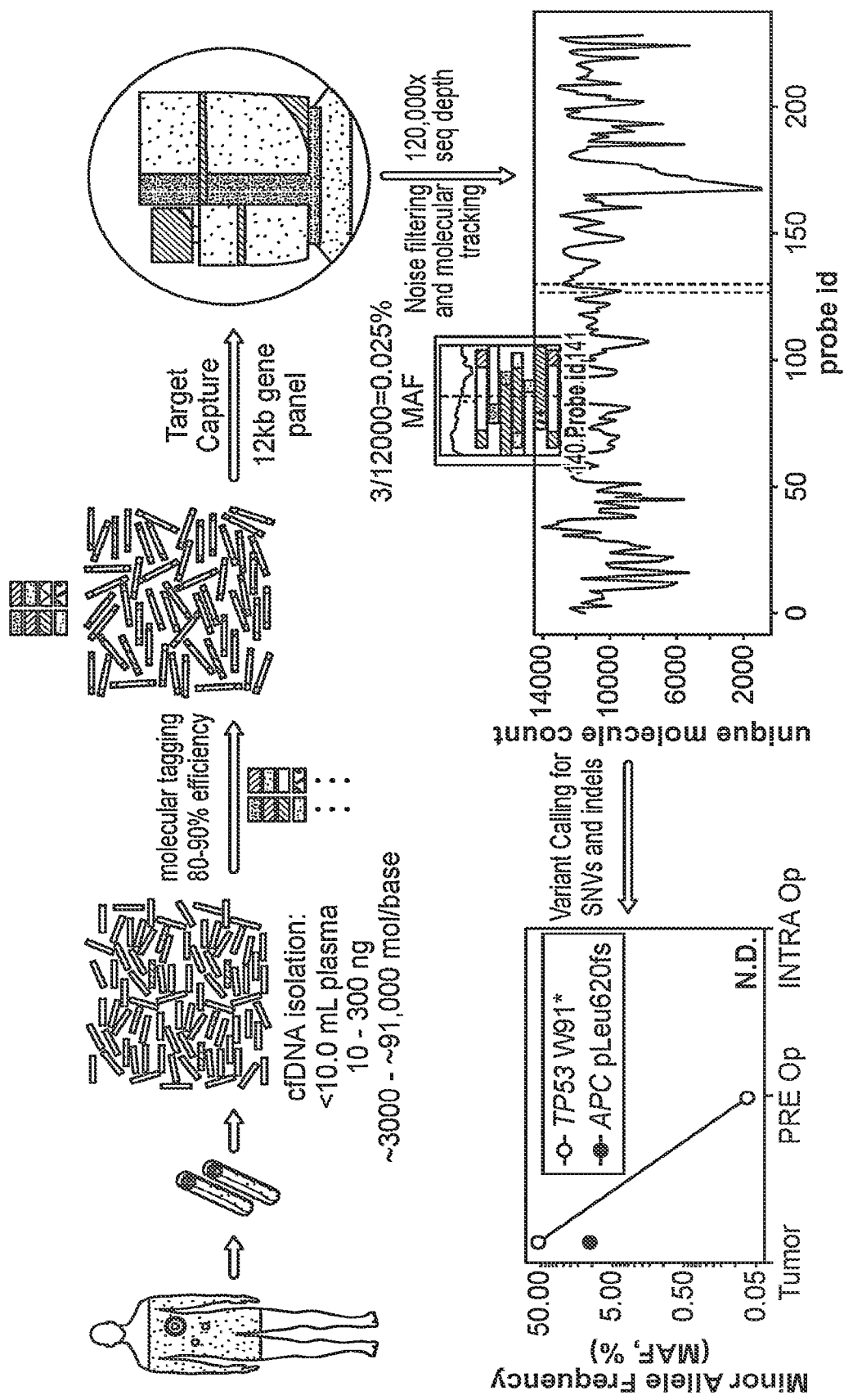
FIG. 2 depicts an example of the methods described herein.
Figure 3:
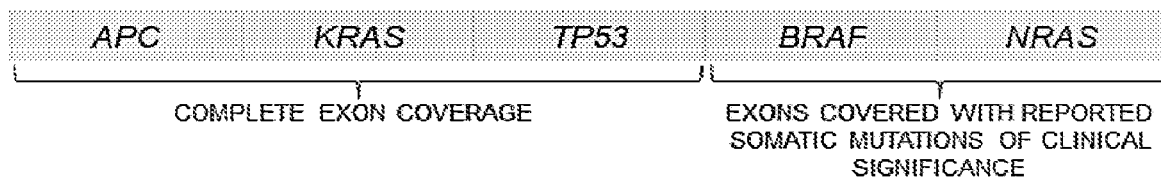
FIG. 3 depicts a 5-gene panel that reports single nucleotide variants (SNVs) and insertions/deletions (indels) in 5 genes.
Figure 4:
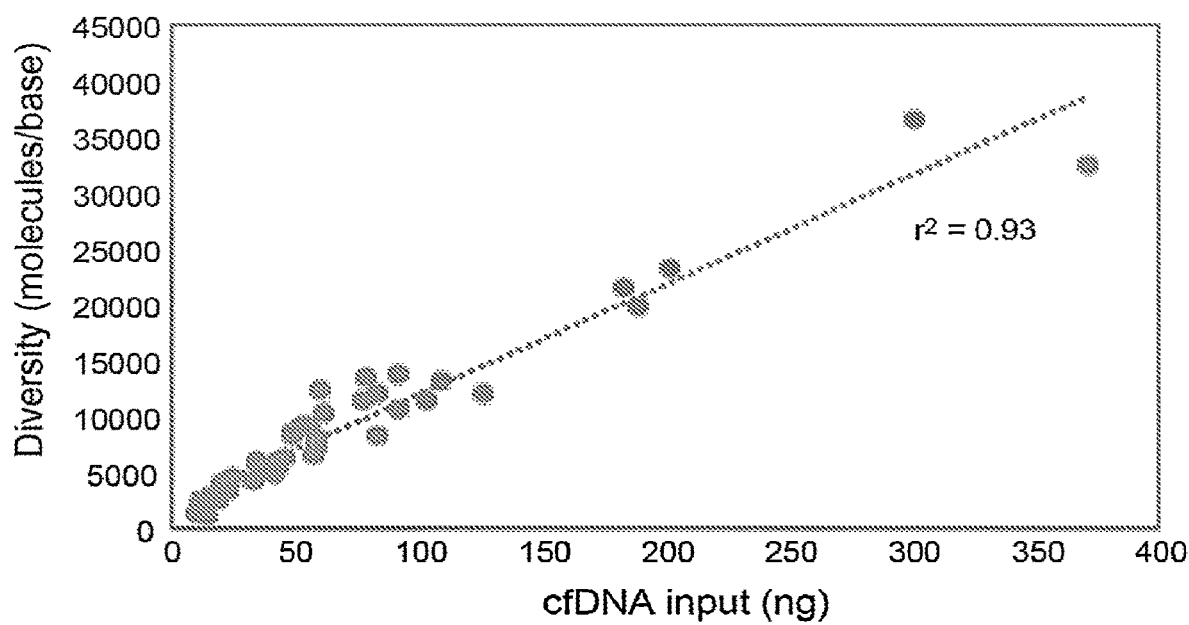
FIG. 4 depicts diversity across cell-free DNA (cfDNA) input for plasma samples. Molecular conversions did not reach saturation over the range of cfDNA input amounts.
Figure 9A:
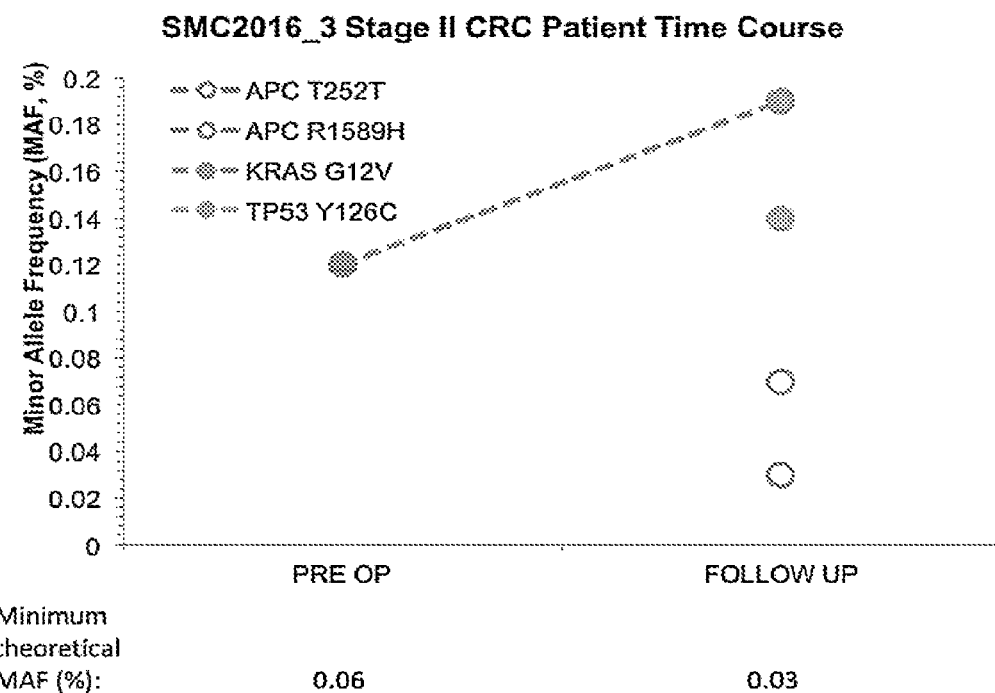
FIGS. 9A, 9B, 9C, and 9D depict time courses for four colorectal cancer (CRC) patients. All reported SNVs and insertions/deletions are included. N.D. indicates samples where nothing was detected. Filled points indicate calls that are concordant with NGS results from surgically resected tumor, while unfilled points indicate discordant calls.
Figure 9B:
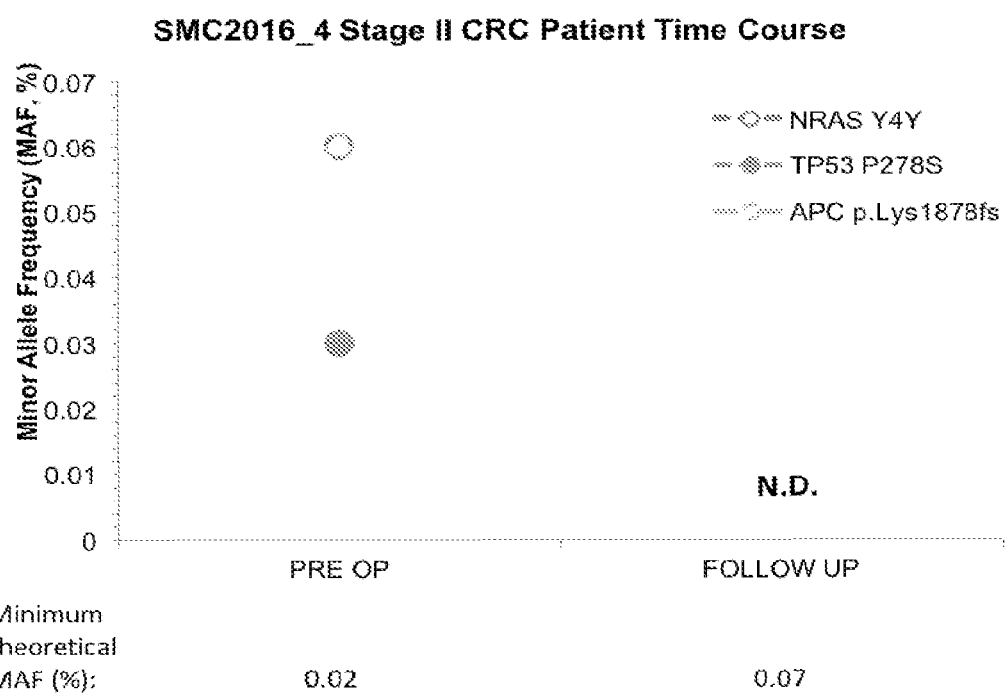
Figure 9C:
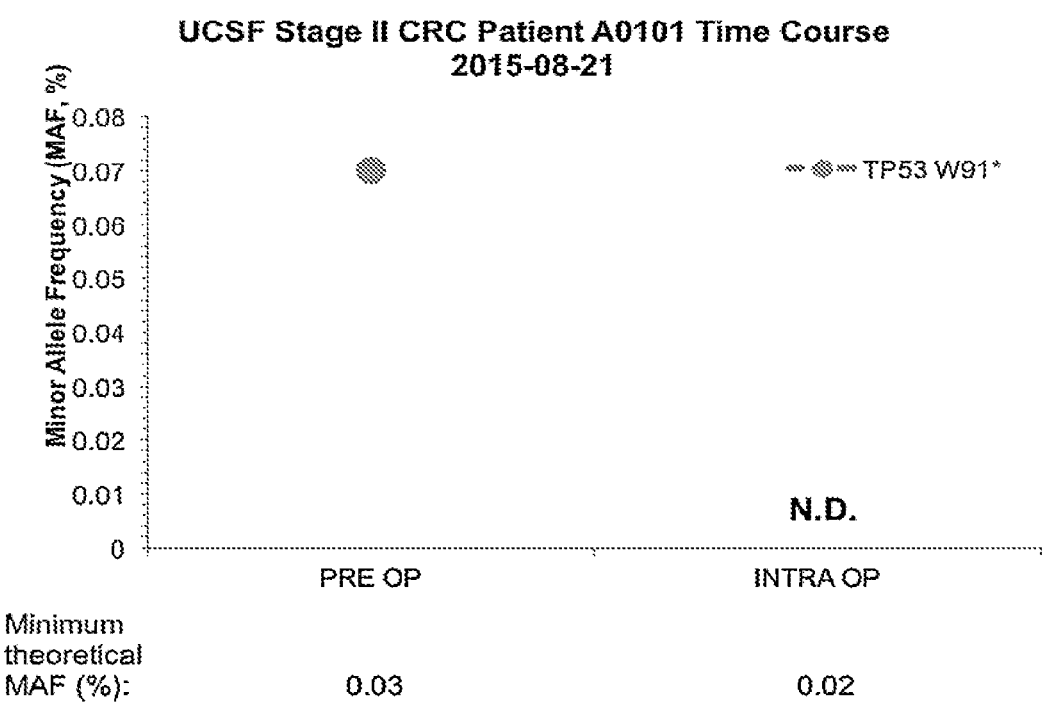
Figure 9D:
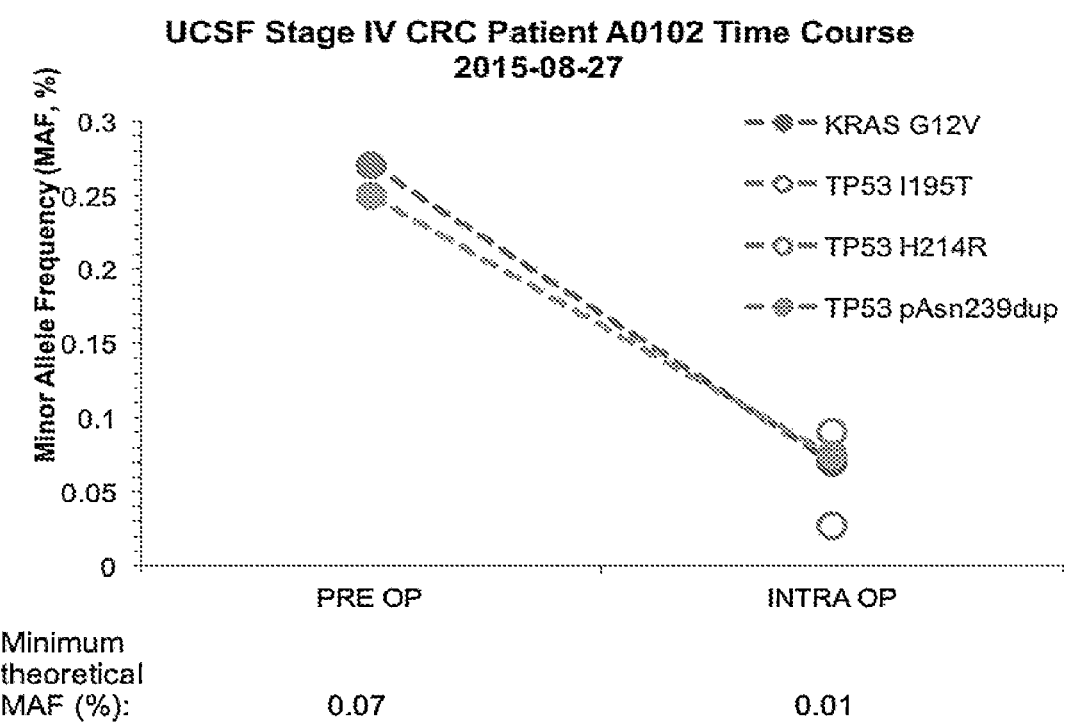
Figure 10:
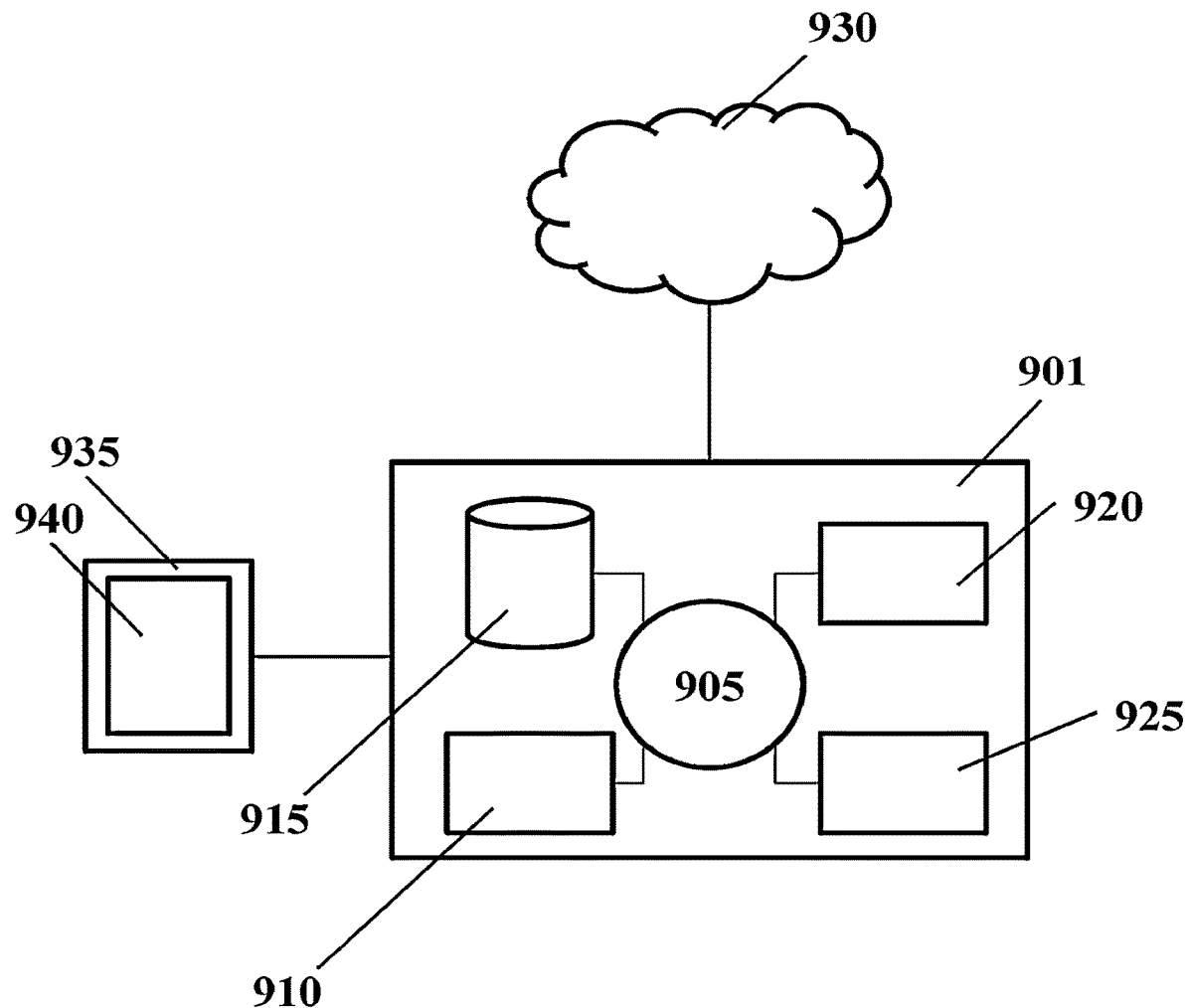
FIG. 10 shows a computer control system that is programmed or otherwise configured to implement methods provided herein.

FIG. 2 depicts the experimental procedure. Cell-free tumor DNA, (ctDNA) was isolated from plasma. Plasma samples were less than 10 mL and yielded 10-300 ng of cfDNA, corresponding to ~3000-~91000 mol/base. A total of 24 "non-unique" DNA tags were ligated to the cfDNA fragments. DNA fragments corresponding to a 12 kb gene panel were captured using biotinylated 120-mer RNA nucleotides and sequenced at 120,000× depth. Noise filtering and molecular tracking were applied and variants were called for SNVs and indels. FIG. 3 shows the composition of the 12 kb gene panel.

Overall, driver mutations were detected in 75% of the pre-op plasma of patients with matched tumor (9/12). FIGS. 5A and 5B show all patients with detected SNVs with a minor allele frequency (MAF) >0.02%. The detection rate of ctDNA in pre-op blood draws was 86% (18/21). In the intra-op/follow-up blood draws, ctDNA was detectable in 48% of cases. In the samples with no tissues as a reference, mutations detected pre-op were also observed in follow up blood draws for 25% of patients (2/8). The estimated average minor allele frequency (MAF) is 0.50% (±0.79%) in pre-op, 0.17% (±0.18%) in intra-op/follow-up, and 34% (±17%) in tumor samples. When tumor tissue was available and used as a reference, the clinical sensitivity, specificity, and accuracy in pre-op blood samples were 57%, 99.997%, and 99.99%, respectively. SNVs with MAF as low as 0.03% were confirmed in tissue data. The clinical specificity of variants detected in intra-op/follow-up blood samples using pre-op samples as the reference is 99.996%. Specificity across a screen of 26 healthy individuals is 99.9987%.

Detection rates were calculated using surgically resected tumor or pre-operation blood samples, in cases were tumor tissue was not available, as a reference, see FIG. 6. A driver mutation also found in tumor was detected pre-op in 9 of the 12 patients with matched tumor, and in 6 of 9 stage II patients. A driver mutation was detected intra-op in 3 of the 6 patients with an intra-op blood draw and 1 of the 3 stage II patients with an intra-op blood draw. A driver mutation was detected in 2 of the 6 patients where follow-up blood draws were taken (all stage II). In follow up blood draws, 31% of stage II patients had an initial driver mutation detected, indicating incomplete resection of the tumor.

FIG. 7 shows concordance analysis for SNV results for pre-op blood draws using tumor NGS on surgically resected tumor as reference. For overall, all reported SNVs from 12 samples are considered, while for stage II only, all reported SNVs for 9 samples are considered.

FIG. 8 shows key sample preparation values. The yields from extracting post-op/follow-up plasma are 2.4× pre-op yields despite comparable plasma volumes. UCSF post-op blood draws were taken immediately following surgery, while SMC follow-up blood draws were taken 7 days after surgery. A0097 and A0105 have two post/follow-up values because a 3-month and 24-day follow-up, respectively, were taken for these patients.

Example 2

Figure 11:
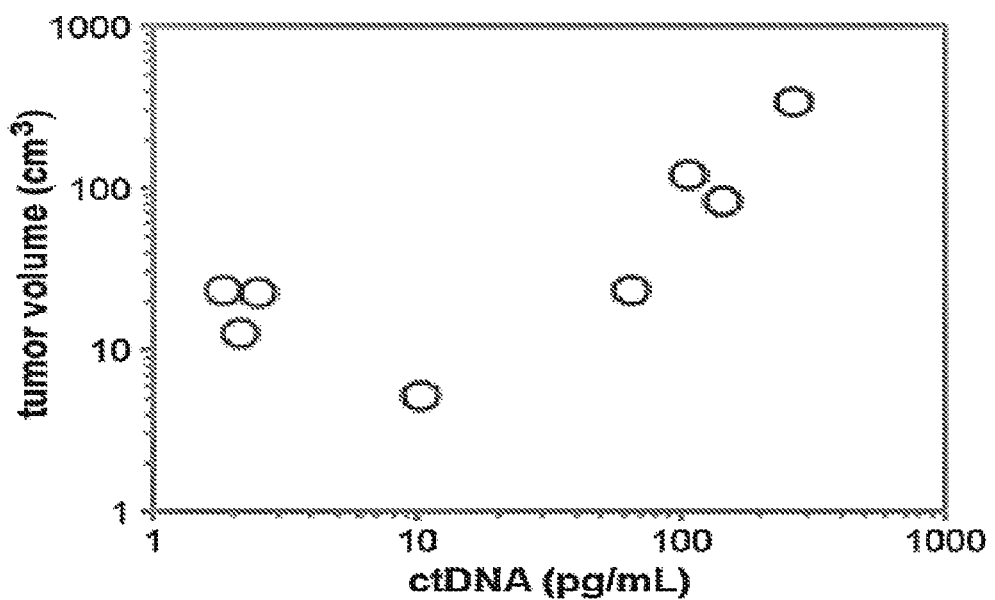
FIG. 11 shows exemplary data demonstrating the correlation of ctDNA concentrations and tumor volumes.

Early, Molecular Detection of Cancer Utilizing Circulating Cell-Free DNA Assay with Ultra-High Accuracy and Sensitivity This example demonstrates a study with Colorectal Cancer (CRC) patients and the subsequent assay improvements driven by the results. In this example, earlier stage cancers, with which less tumor DNA was shed into the circulation (FIG. 11), and was detected by the analysis of cell-free circulating tumor DNA (ctDNA) with next-generation sequencing (NGS).

Methods

As a first iteration of this process, a 25 kb capture panel was developed based on the landscape of genomic alterations in ctDNA of over 10,000 advanced cancer patients (GH database). The panel content was selected to achieve high clinical sensitivities for colorectal (96%), ovarian (95%), lung (87-93%), and pancreatic (88%).

Figure 12:
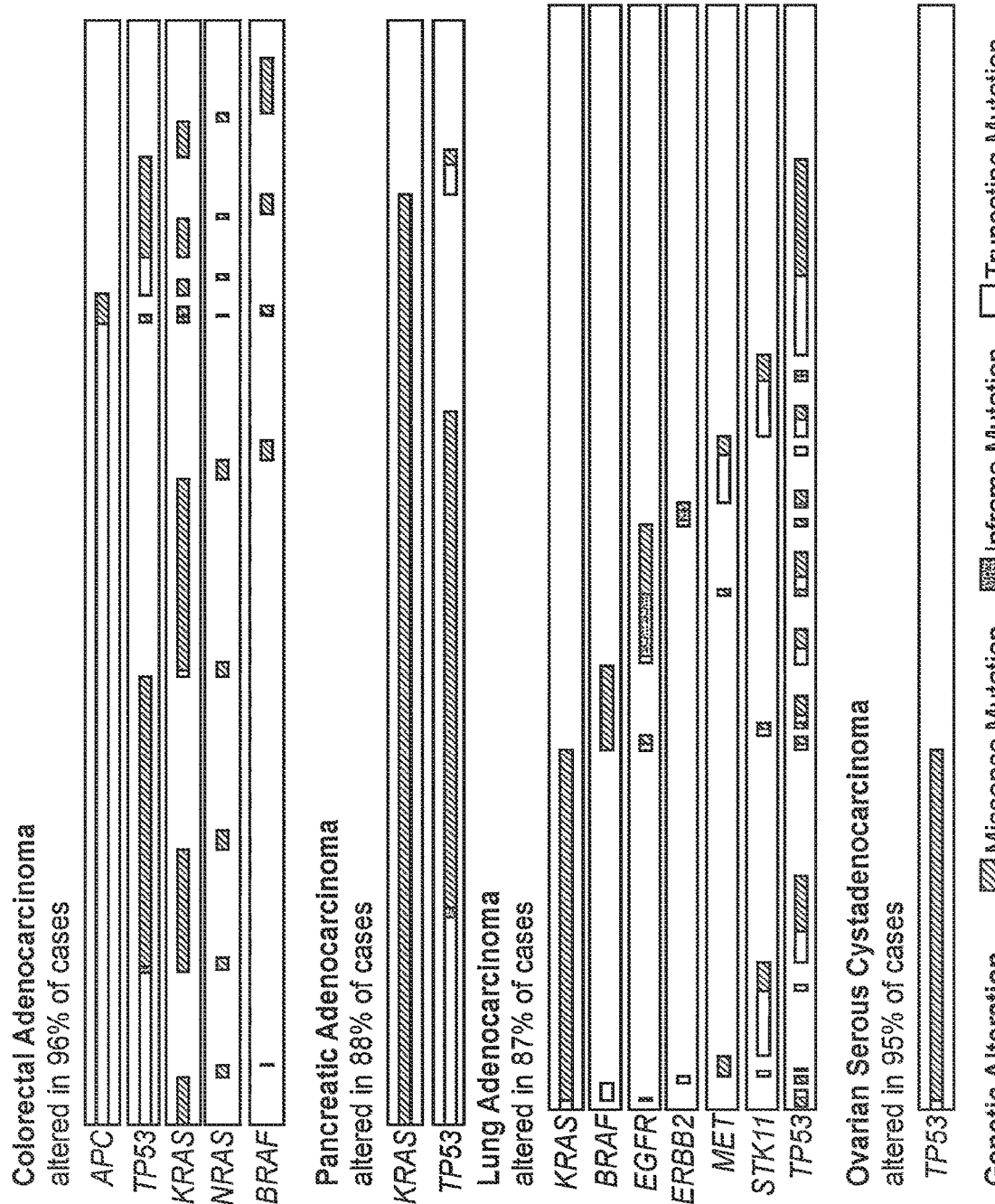
FIG. 12 shows exemplary oncoprints of four major cancer types: colorectal adenocarcinoma, pancreatic adenocarcinoma, lung adenocarcinoma, and ovarian serous cystadenocarcinoma corresponding to a subset of genes on the 25-gene panel in Example 2.

Panel: The 25-gene panel reported SNVs in 25 genes, indels in 7 genes, and fusions in 1 gene. FIG. 12 shows oncoprints of four major cancer types: colorectal adenocarcinoma, pancreatic adenocarcinoma, lung adenocarcinoma, and ovarian serous cystadenocarcinoma corresponding to a subset of genes on the 25-gene panel.

Figure 13:
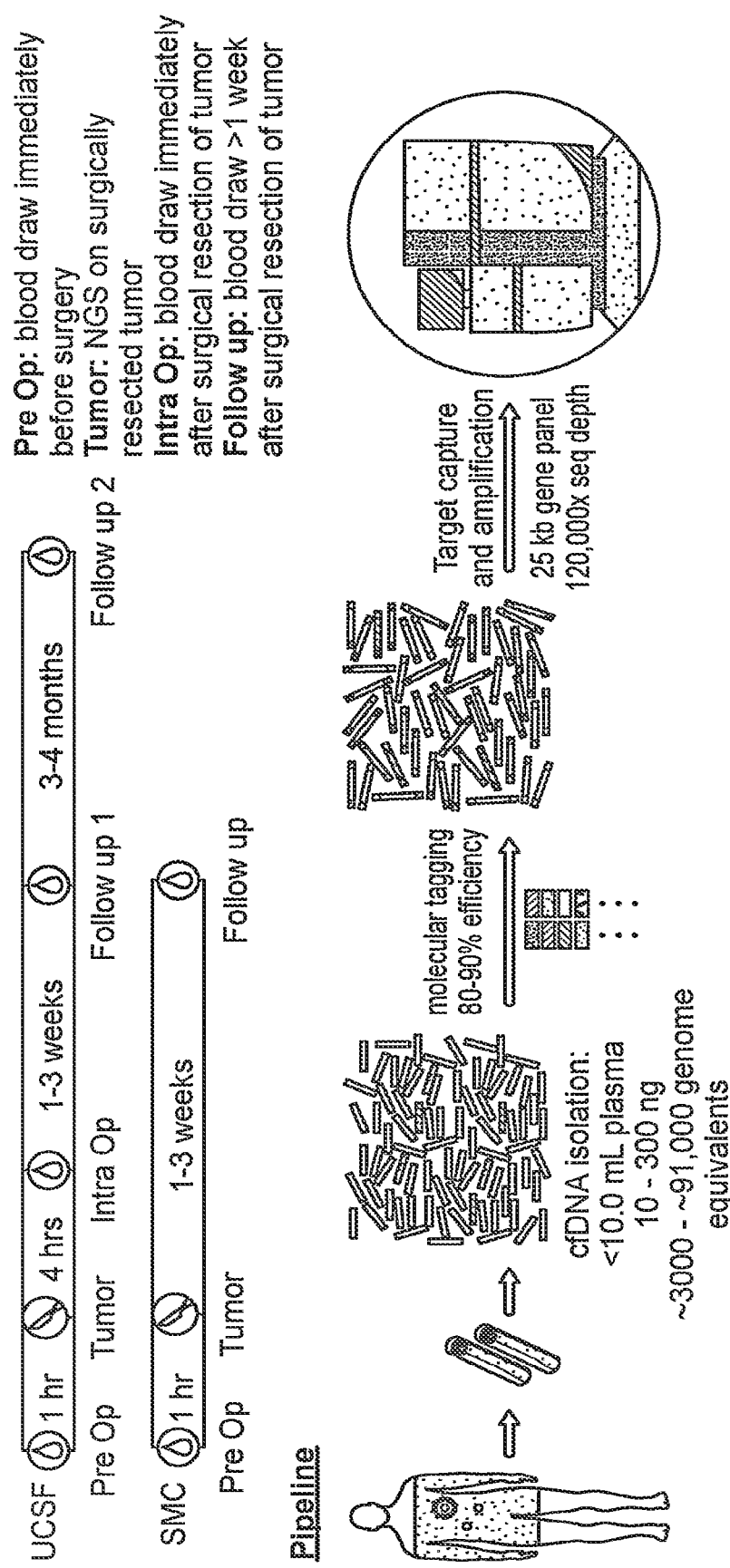
FIG. 13 depicts an example of the study design described in Example 2. Pre Op: blood draw immediately before surgery; Tumor: NGS on surgically resected tumor; Intra Op: blood draw immediately after surgical resection of tumor; Follow up: blood draw >1 week after surgical resection of tumor.

Feasibility Study Design: This panel was applied to a study cohort of 21 CRC patients with both pre- and intra-op/follow-up blood draws at two sites, UCSF and SMC. A subset (12 patients) also had tumor specimens collected at the time of the surgery provided for sequencing. A pipeline of the study design is described in FIG. 13.

Results

Figure 14A:
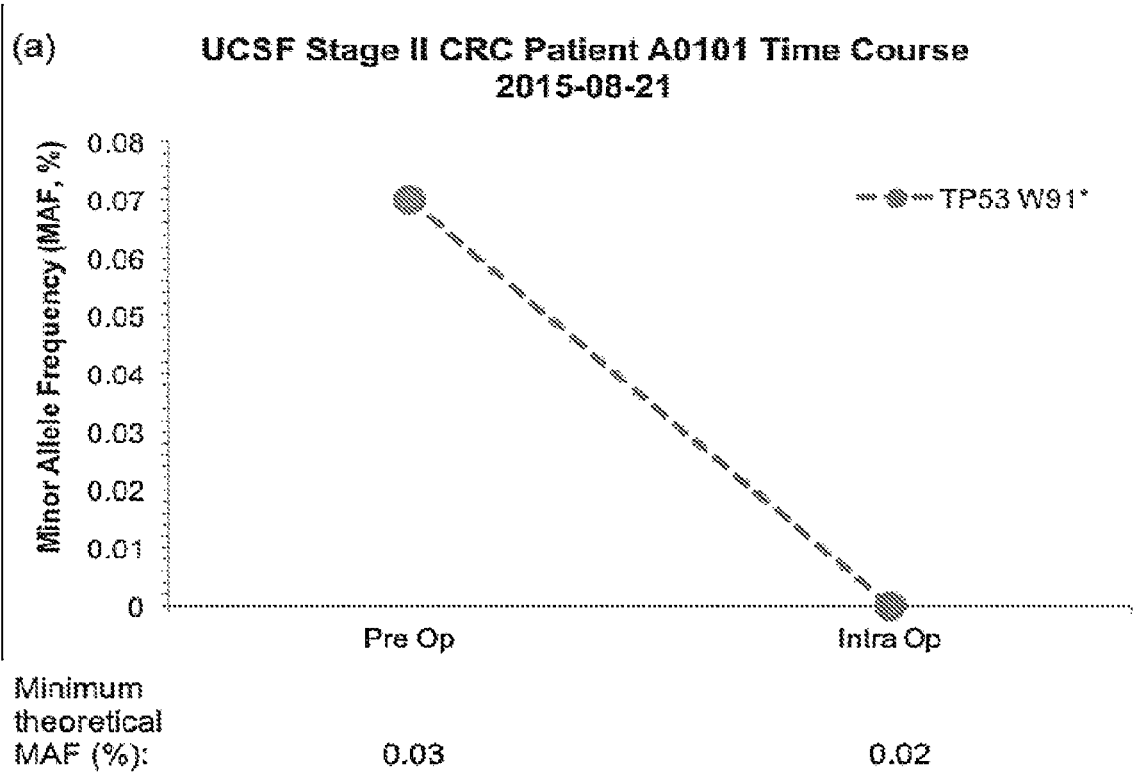
FIGS. 14A, 14B, 14C and 14D show a time courses for four patients. All reported tumor-positive SNVs and insertions/deletions were included.
Figure 14B:
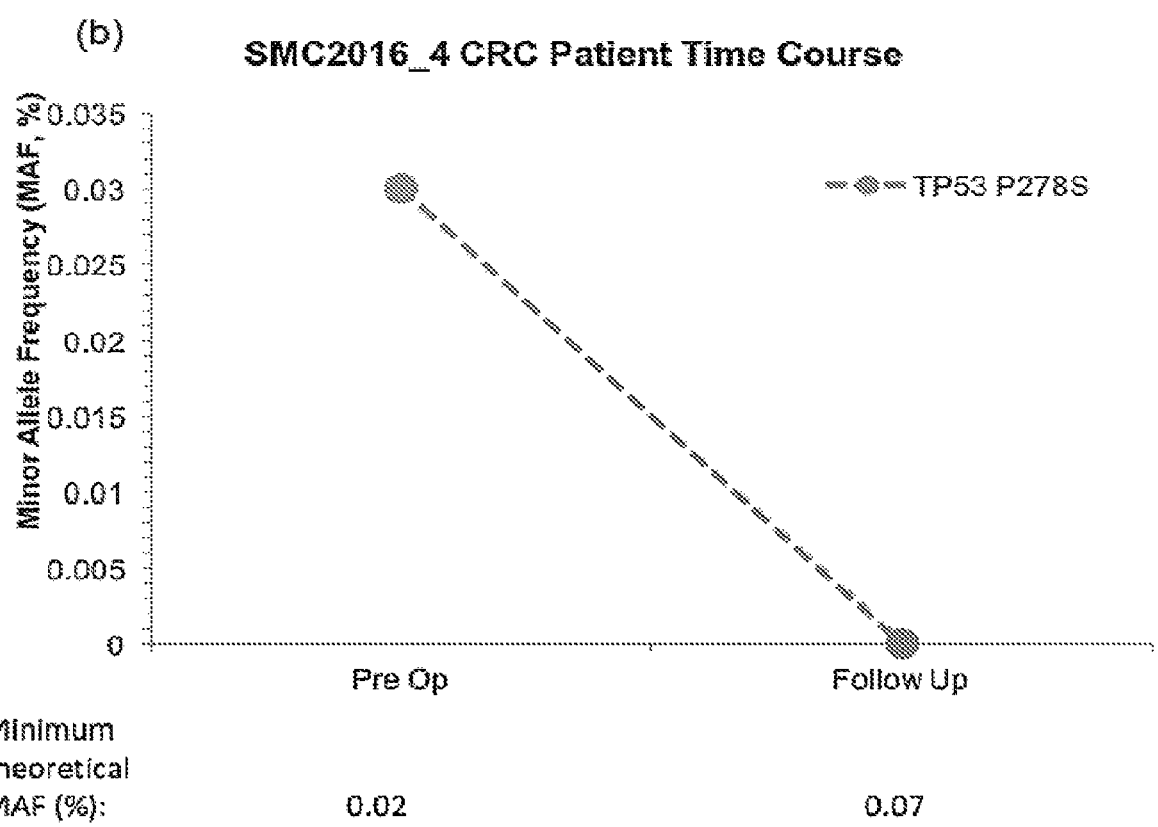
Figure 14C:
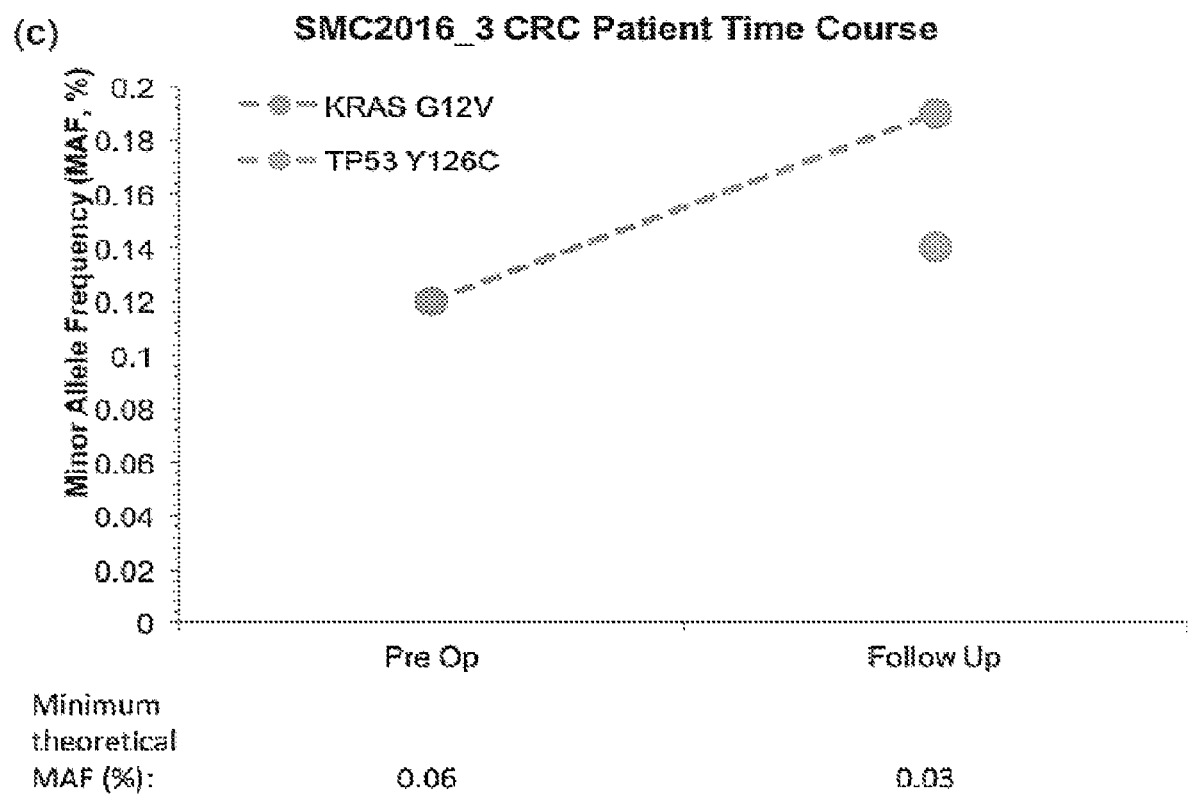
Figure 14D:
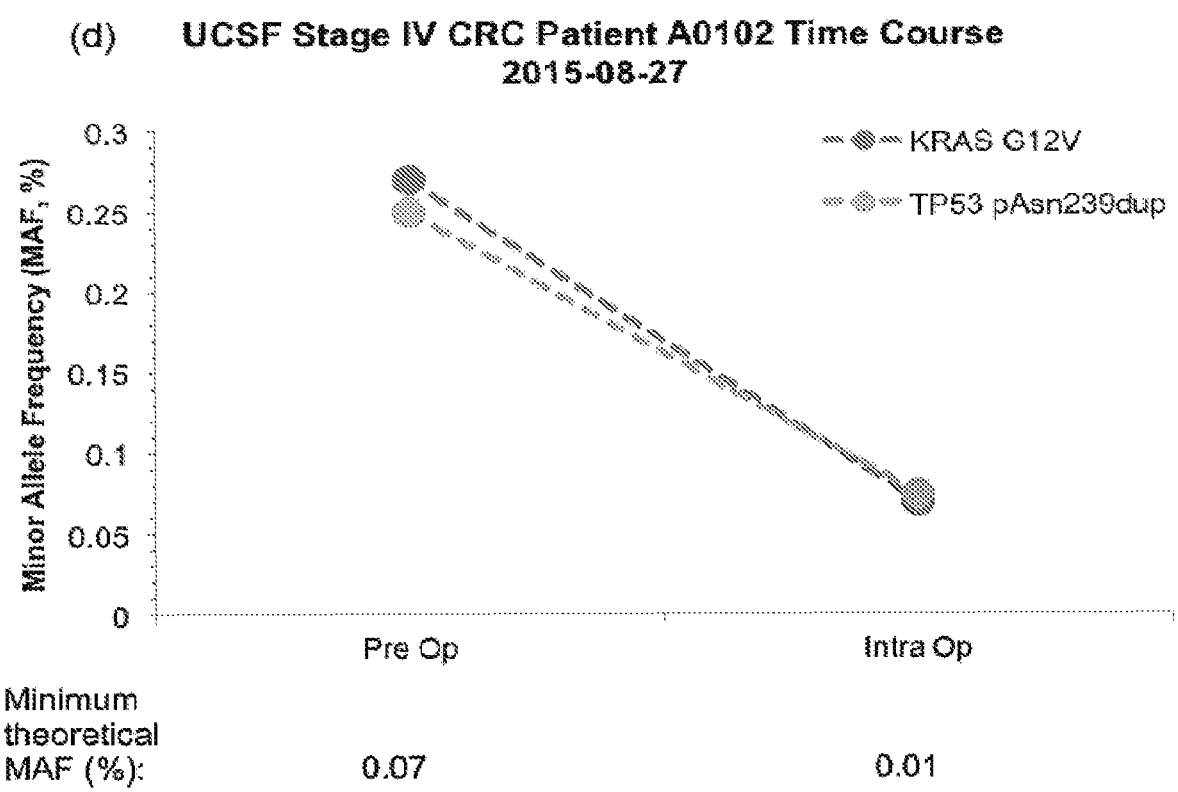

Overall, mutations were detected in 86% (19/21) of all pre-op samples and 75% (9/12) of those with matched tumor. Index mutations, defined as mutations that are detected in either two or more blood draws or in tumor and a single blood draw, persisted in 29% of patients post-surgery, indicating molecular residual disease. SNVs with mutant allele fraction (MAF) as low as 0.03% cell-free DNA (cfDNA) were confirmed in tissue data. The estimated average mutant allele frequency (MAF) was 0.48% (±0.76%) in pre-op, and 0.16% (±0.17%) in intra-op/follow-up. When tumor tissue was available and used as a reference, the clinical sensitivity in pre-op blood samples was 57%, and the positive predictive value was 75%, perhaps reflecting tissue-based false negatives. Specificity across a screen of 26 healthy individuals was 99.9987%. Cohort expansion to 50 patients and follow-up for clinical recurrence in both cohorts was ongoing, as was expansion to additional cancer types. FIGS. 14A, 14B, 14C and 14D show a time courses for four patients. All reported tumor-positive SNVs and insertions/deletions were included. FIGS. 14A and 14B demonstrate that surgery successfully removed key mutations. FIGS. 14C and 14D show evidence of molecular residual disease.

Tables 1 and 2 show the reported mutations. Table 1 shows reported SNVs and indels for tumor-positive mutations. SNVs and indels with MAF >0.02% were reported. Dash indicates that the mutation was not detected. Parentheses indicate a mutation that our pipeline detected but did not have sufficient support to call. Table 2 shows reported SNVs and indels for samples without matched tumor. SNVs and indels with MAF >0.02% were reported. Dash indicates that the mutation was not detected.

TABLE 1

| Patient | Clinical Stage | Pathological Stage | Gene | Mutation | MAF (%) Pre op | MAF (%) Intra op/ Follow up |
|---|---|---|---|---|---|---|
| SMC2016_1 | II | — | KRAS | G13D | — | 0.06 |
|  |  |  | APC | p.Leu1489fs | — | — |
|  |  |  | TP53 | p.Pro47fs | — | — |
| SMC2016_2 | II | — | KRAS | G12V | — | — |
|  |  |  | TP53 | C141Y | — | — |
| SMC2016_3 | II | — | KRAS | G12V | 0.12 | 0.19 |
|  |  |  | TP53 | Y126C | — | 0.14 |
| SMC2016_4 | II | — | TP53 | P278S | 0.03 | — |
|  |  |  | APC | p.Arg216fs | — | — |
| SMC2016_5 | II | — | APC | R1386* | — | — |
|  |  |  | TP53 | P152L | — | — |
| SMC2016_6 | II | — | TP53 | L252P | 0.04 | — |
|  |  |  | APC | K523* | — | — |
|  |  |  | KRAS | G12D | — | — |
| A0097 | II | III | APC | Q1378 | 2.86 | 0.17 |
|  |  |  | TP53 | R213* | 3.47 | 0.20 |
| A0098 | II | III | APC | R283* | 0.2 | (0.03) |
|  |  |  | APC | F1396F | 0.3 | — |
|  |  |  | KRAS | G12V | 0.5 | — |
|  |  |  | APC | p.Gln1406fs | 0.2 | — |
|  |  |  | TP53 | p.Asn239fs | — | — |
| A0101 | II | II | TP53 | W91* | 0.07 | — |
|  |  |  | APC | p.Leu620fs | — | — |
| A0102 | IV | IV | KRAS | G12V | 0.27 | 0.07 |
|  |  |  | TP53 | p.Asn239dup | 0.25 | 0.09 |
| A0105 | II | II | TP53 | R273C | 0.14 | (0.01) |
|  |  |  | KRAS | G12D | — | — |
| A0106 | II | II | TP53 | H214R | 0.28 | 0.04 |
|  |  |  | APC | S1356* | 0.29 | — |
|  |  |  | KRAS | G12V | — | — |

TABLE 2

| Patient | Clinical Stage | Pathological Stage | Gene | Mutation | MAF (%) Pre op | MAF (%) Intra op/ Follow up |
|---|---|---|---|---|---|---|
| A111 | II | — | TP53 | R158H | 0.38 | 0.40 |
|  |  |  | NRAS | E76K | — | 0.03 |
| 1 SMC | II | — | APC | E1306* | 0.4 | — |
|  |  |  | TP53 | G245S | 0.5 | — |
|  |  |  | KRAS | D173D | 2.1 | — |
| 2 SMC | II | — | TP53 | R273H | 0.07 | — |
| 3 SMC | II | — | TP53 | G245D | 0.4 | 0.3 |
|  |  |  | TP53 | C242Y | 0.6 | 0.8 |
|  |  |  | KRAS | G12D | 0.2 | — |
| 4 SMC | II | — | APC | E1397* | 0.2 | — |
|  |  |  | APC | R213* | 0.3 | — |
|  |  |  | TP53 | H179R | 1.1 | — |
| 5 SMC | II | — | APC | p.Lys1616_Leu1617delinsAsn | — | 0.11 |
| 6 SMC | II | — | TP53 | R282Q | 0.49 | — |
|  |  |  | TP53 | T125M | 0.34 | — |
| 7 SMC | II | — | APC | S2586D | 0.17 | 0.15 |
|  |  |  | APC | p.Arg1048fs | 0.08 | 0.07 |
| 8 SMC | II | — | KRAS | G12D | 0.25 | — |

Table 3 shows the assay metrics and performance values. The yields from extracting intra-op/follow-up plasma were 2.4× pre-op yields despite comparable plasma volumes. UCSF intra-op blood draws were taken immediately following surgery, while SMC follow-up blood draws were taken 7 days after surgery.

TABLE 3

| Total Plasma (mL) | | cfDNA Yield (ng/mL) | | Library Input (ng) | |
|---|---|---|---|---|---|
| Pre | Intra op/ Follow up | Pre op | Intra op/ Follow up | Pre op | Intra op/ Follow up |
| 4.9 | 4.4 | 10 | 24 | 40 | 100 |

Table 4 shows the detection rate by patients. A mutation was detected pre-op in 9 of 12 patients with matched tumor. A mutation was detected intra-op in 4 of the 7 patients with an intra-op blood draw. A mutation was detected at follow-up in 4/14 patients where follow-up blood draws were taken. If mutations with any evidence were included, the percentage of patients with a mutation detected intra-op is 86% overall.

TABLE 4

| | % of patients with mutation detected |
|---|---|
| pre op | 75% |
| intra op | 57% |
| follow up | 29% |

Figure 16A:
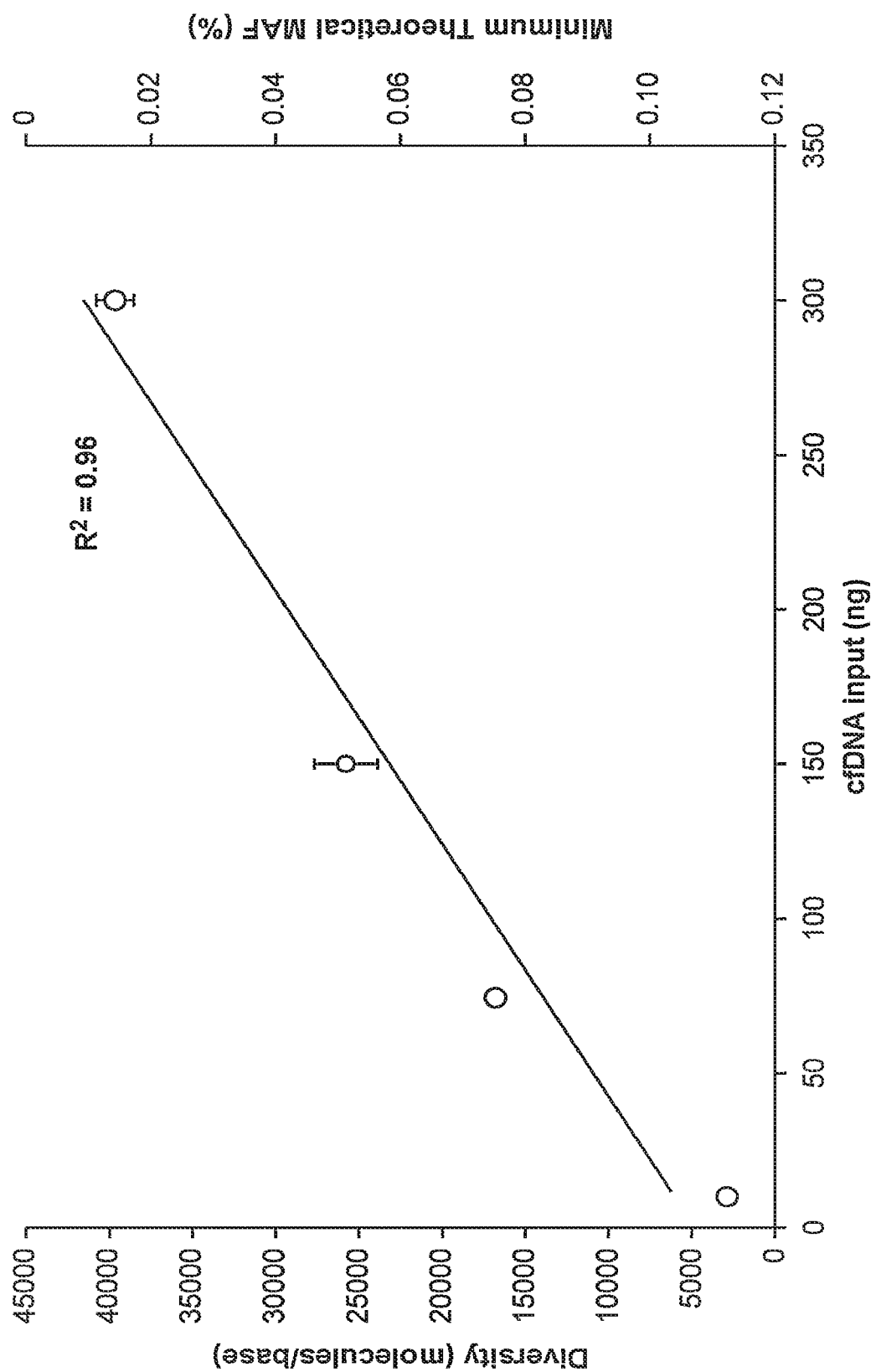
FIGS. 16A and 16B show improved diversity and gene coverage for greater sensitivity.
Figure 16B:
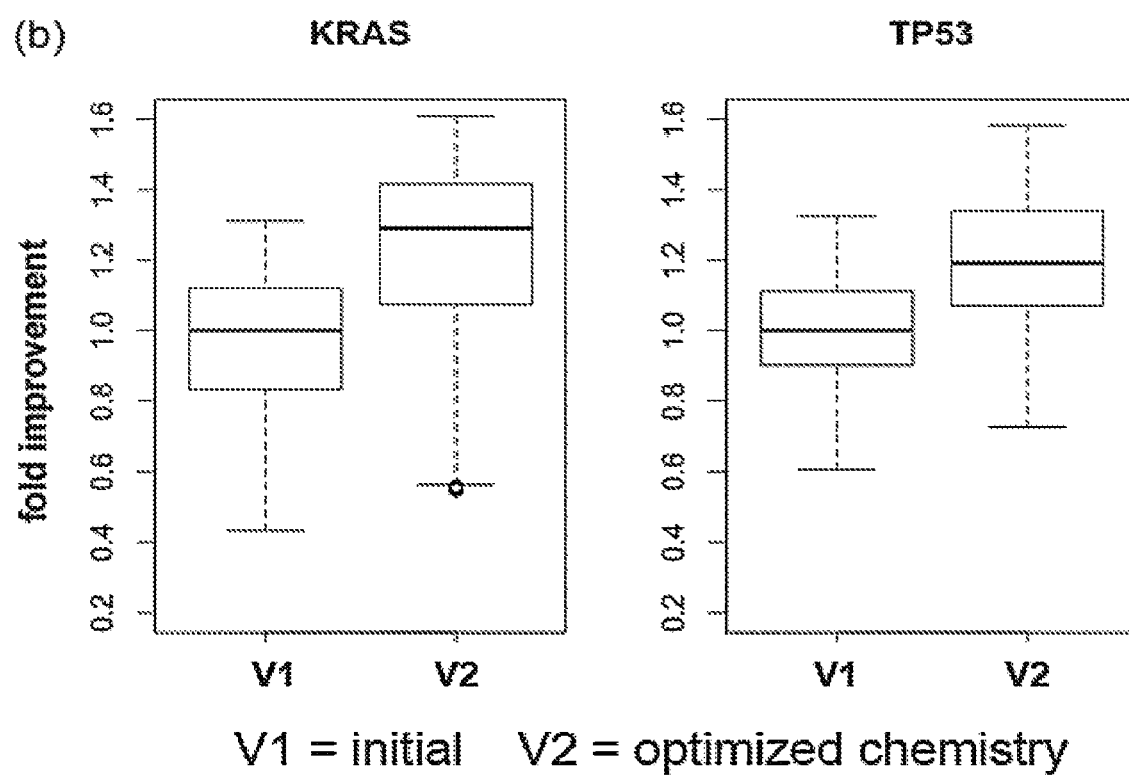

Assay improvements for increased sensitivity: The CRC-specific panel was expanded into a new panel designed to achieve high clinical sensitivity for colorectal, ovarian, lung, and pancreatic cancers. Sites where mutations were prevalent in the GH database were also included. This 25-gene panel reported SNVs in 25 genes, indels in 7 genes, and fusions in 1 gene. FIG. 15 shows genes selected for detection of major cancer types with >90% theoretical sensitivity. Bolded genes indicate genes with complete exon coverage. FIGS. 16A and 16B show improved diversity and gene coverage to achieve greater sensitivity. FIG. 16A shows diversity across cfDNA input for analytical samples. Molecular conversions did not reach saturation over our range of cfDNA input. Higher diversity allows for detection at lower MAFs. FIG. 16B shows two key genes with significant coverage improvements with assay optimization.
Conclusion A non-invasive multigene cfDNA NGS assay was developed in this example for the early detection of ctDNA. In this example, the early-stage assay detected ctDNA alterations present in the post-surgical tumor specimen in 75% of patients' pre-op samples and at mutant allele fractions an order of magnitude lower than the current clinical assay. Evidence of molecular residual disease was found in 29% of patients regardless of stage and follow-up to correlated MRD with clinical outcomes.

Example 3

Detection of Lung Cancer in High Risk Smokers with Irregular Nodules using a Circulating Cell-Free DNA Assay with Ultra-High Accuracy and Specificity In about 40 percent of cases, non-small cell lung cancer (NSCLC) may be diagnosed in stage 4, at which point a diagnosed patient may have less than a year of expected survival time. Liquid biopsies can aid in earlier detection of lung cancer among a cohort of patients (e.g., smokers) at high risk for lung cancer (e.g., higher than average risk compared to the general population) with irregular nodules. Since roughly half of smokers over the age of 50 may be expected to present with one or more lung nodules on a CT chest scan, a highly sensitive and specific non-invasive test (e.g., a circulating cfDNA assay) may be needed to perform differential diagnosis of lung cancer. With earlier stage cancers, less tumor DNA is shed into circulation, thus requiring very high sensitivity. The specificity of the circulating cfDNA assay on a subject may requirement enhancement because subjects in a high risk smoker cohort may be expected to exhibit a high prevalence of genomic alterations not necessarily associated with cancer. Thus, a diagnosis of lung cancer by liquid biopsy may be enhanced by incorporation of additional clinical information (e.g., age, smoking history, and radiological data) of the subject. In addition, specificity can be further enhanced by performing validation testing on a lung nodule after it is removed. A clinical decision to remove such a lung nodule may be performed based in part on the results of the circulating cfDNA assay.

A 7.5 kb ctDNA capture panel is developed based on the landscape of genomic alterations in ctDNA of 10,000 advanced lung cancer patients with high theoretical clinical sensitivity for lung cancer (87-93%). The panel is used in a cfDNA assay to achieve a PPV of 95% at 0.025%-0.05% MAF and a PPV of 99% above 0.05% MAF. The panel is applied to a clinical study of 100 high-risk subjects with significant history of smoking having irregular nodules of indeterminate status (e.g., no definitive clinical diagnosis of a benign or malignant tumor in the lung). The detection rate of ctDNA in blood draws from the subjects is 40% (40/100). Based on the identification of ctDNA, the 40 positively identified subjects are further subjected to surgical removal and sequencing analysis of their lung nodules. Sequencing analysis of the lung nodules confirms a diagnosis of lung cancer in 90% (36/40) of the subjects with a positive ctDNA test. The remaining 60 subjects who did not exhibit detectable ctDNA are subjected to repeated cfDNA testing every month, and subjects who subsequently receive a positive identification of ctDNA have a likely diagnosis of lung cancer, which can be confirmed by surgical removal and sequencing analysis of lung nodules. If the cohort of 100 high-risk subjects with significant history of smoking having irregular nodules of indeterminate status did not receive a ctDNA assay, the subjects may receive painful biopsies and/or follow-up radiological scans on 6 to 12 month intervals to observe any clinical changes (e.g., nodule growth) to obtain more definitive diagnoses of lung cancer.

In conclusion, a clinically useful assay is developed for the detection of ctDNA in a cohort of high-risk subjects with irregular lung nodules. This allows for a non-invasive route for high sensitivity and specificity diagnosis of lung cancer compared to traditional clinical methodologies.

1. Example 4

Assaying ctDNA Utilizing a High-Sensitivity Panel Detects a High-Level MET Amplification in Lung Cancer and Guides Therapy Selection A 70-year-old former light smoker (15 packs/year) with pulmonary fibrosis and moderate pulmonary hypertension was diagnosed with a 30 mm right middle lobe stage IIIA lung adenocarcinoma and treated with definitive chemoradiotherapy. After five months, mediastinal, liver, and multiple bone metastases were diagnosed. After two months of treatment with a targeted therapeutic regimen (afatinib) for a rare EGFR mutation (1744F), a significant progression occurred. The patient was not a candidate for chemotherapy and there was no tissue available for molecular testing.

Circulating tumor DNA (CtDNA) testing was performed with a 70-gene ctDNA NGS panel (see Table 5) that includes all NCCN-recommended somatic genomic variants for solid tumors and completely sequences the critical exons in 70 genes to identify all four major types of genomic alterations: single nucleotide variants (SNVs), selected indels and fusions, and copy number amplifications (CNA) in 16 genes with high sensitivity (85% in stage III/IV solid tumors) and ultra-high specificity (>99.9999%). CNA for MET and other genes have been validated against cell lines with known amplifications and are reported as 1+, 2+ or 3+ with the latter representing the absolute copy number of the gene in blood at the 90th percentile and higher.

TABLE 5

| POINT MUTATIONS - Complete* or Critical Exon Coverage in 70 Genes | | | | | | | | | | |
|---|---|---|---|---|---|---|---|---|---|---|
| AKT1 | ALK | APC | AR | ARAF | ARID1A | ATM | BRAF | BRCA1 | BRCA2 | |
| CCDN1 | CCND2 | CCNE1 | CDH1 | CDK4 | CDK6 | CDKN2A | CDKN2B | CTNNB1 | EGFR | |
| ERBB2 | ESR1 | EZH2 | FBXW7 | FGFR1 | FGFR2 | FGFR3 | GATA3 | GNA11 | GNAQ | |
| GNAS | HNF1A | HRAS | IDH1 | IDH2 | JAK2 | JAK3 | KIT | KRAS | MAP2K1 | |
| MAP2K2 | MET | MLH1 | MPL | MYC | NF1 | NFE2L2 | NOTCH1 | NPM1 | NRAS | |
| NTRK1 | PDGFRA | PIK3CA | PTEN | PTPN11 | RAF1 | RB1 | RET | RHEB | RHOA | |
| RIT1 | ROS1 | SMAD4 | SMO | SRC | STK11 | TERT | TP63 | TSC1 | VHL | |
| AMPLIFICATIONS | | | | | | | | | | |
| AR | BRAF | CCNE1 | CDK4 | CDK6 | EGFR | ERBB2 | FGFR1 | | | |
| FGFR2 | KIT | KRAS | MET | MYC | PDGFRA | PIK3CA | RAF1 | | | |
| FUSIONS | | | | | | | | | | |
| ALK | FGFR2 | FGFR3 | RET | ROS1 | NTRK1 | | | | | |
| INDELS | | | | | | | | | | |
| EGFR exons 19/20 | ERBB2 exons 19/20 | MET exon 14 skipping | | | | | | | | |

Figure 17A:
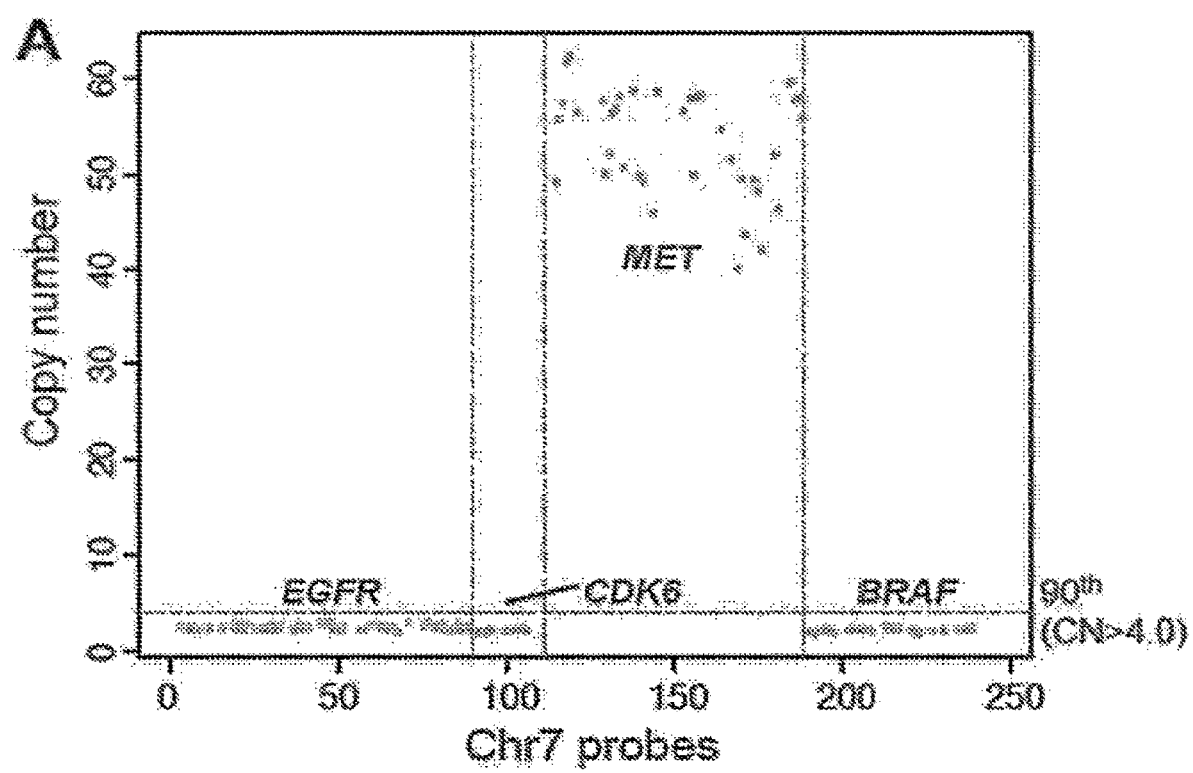
FIG. 17A depicts copy number of various genes in a patient with non-small cell lung cancer (NSCLC) after treatment with anti-EGFR therapy.
Figure 17B:
FIG. 17B depicts computed tomography/positron emission tomography (CT/PET) scans before and after treatment with crizotinib.

CtDNA NGS testing identified a high-level MET amplification (copy number of 53.6 in circulation) (FIG. 17A). The test was repeated on a second tube of blood submitted at the same time point, with the second test showing a similar MET gene copy number (60.0). Crizotinib was prescribed to target the MET amplification. After treatment of the patient was started, comprising administering the anti-MET therapy to the subject to treat the NSCLC, immediate clinical improvement and a significant imaging response on CT/PET scans were observed (FIG. 17B). Three months after start of treatment, the patient was fully active, able to carry on all predisease performance without restriction (ECOG Performance Status=0) and was symptom-free. Similar ctDNA testing on other NSCLC patients may yield an identification of a CNA of the MET gene in the ctDNA of at least about 20, at least about 30, at least about 40, or at least about 50. The CNA may be identified with a sensitivity of at least 80%. The CNA may be identified with a specificity of at least 99.9%, at least 99.99%, at least 99.999%, or at least 99.9999%.

Figure 18:
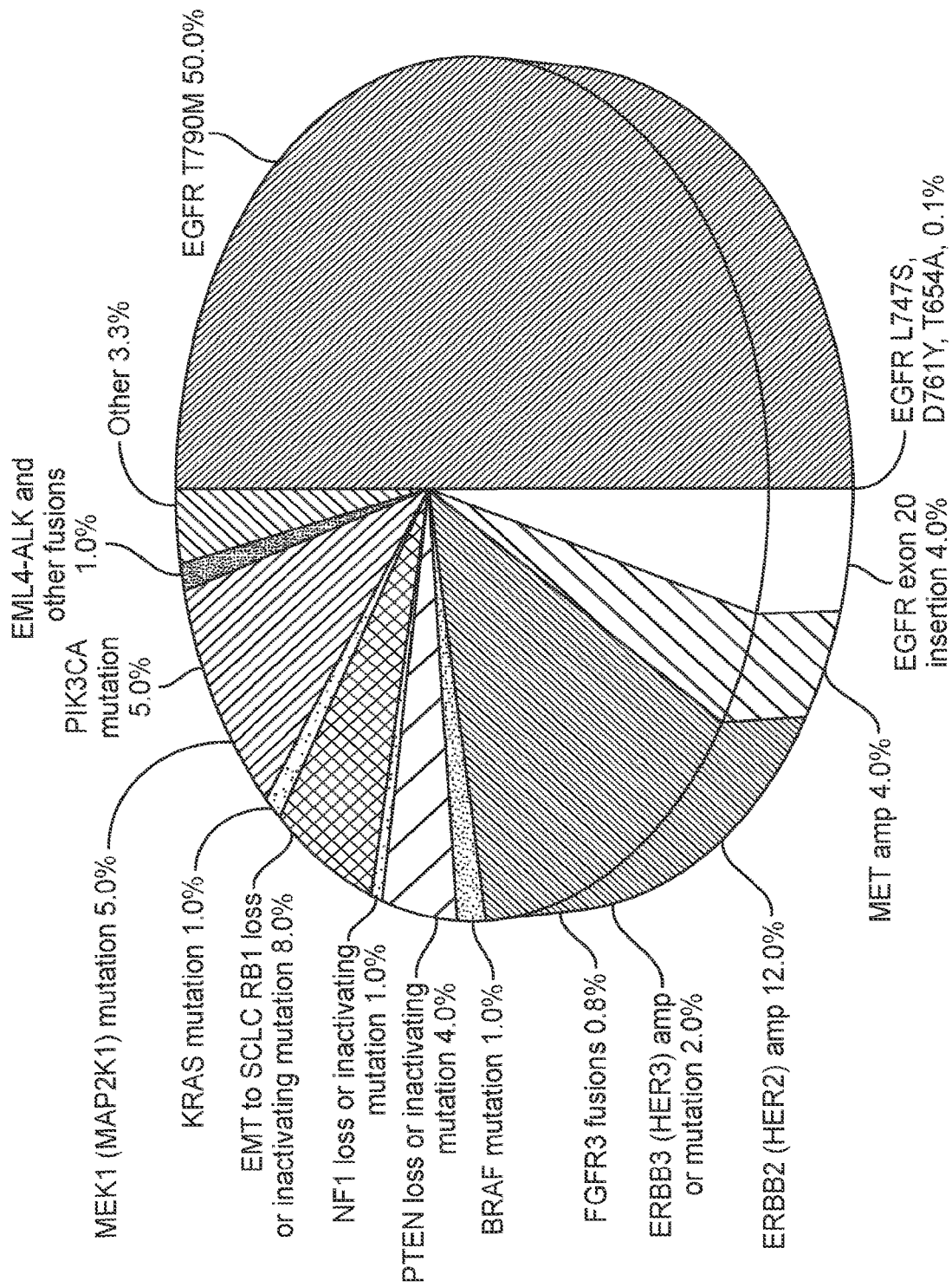
FIG. 18 depicts a frequency distribution of secondary resistance mechanisms to anti-EGFR therapy.

Analysis of ctDNA in this metastatic NSCLC cancer patient identified MET gene amplification and the patient had a dramatic response to crizotinib. Liquid biopsy methods such as ddPCR may identify EGFR T790M, but NGS methods may be required to detect the other 50% of the secondary resistance mechanisms (FIG. 18), such as MET amplification—which occurs in 5% of patients on EGFR inhibitors. CtDNA detection of MET amplification as a key resistance mechanism after EGFR TKI therapy is feasible with a targeted NGS method when tissue is not accessible or biopsy performed but was quantity not sufficient (QNS) for genotyping.

4. Example 5

Assaying ctDNA Utilizing a High-Sensitivity Panel Detects ERBB2 Mutations (e.g., Indels) in Breast Cancer and Guides Therapy Selection Two percent of metastatic breast cancer (MBC), predominantly HER2 non-amplified patients, harbor ERBB2 (HER2) single nucleotide variants or indels which may benefit from targeted tyrosine kinase inhibitors. ERBB2 mutations may be non-invasively identified and in treatment-refractory MBC with targeted next generation sequencing (NGS) of circulating tumor DNA (ctDNA).

Figure 19:
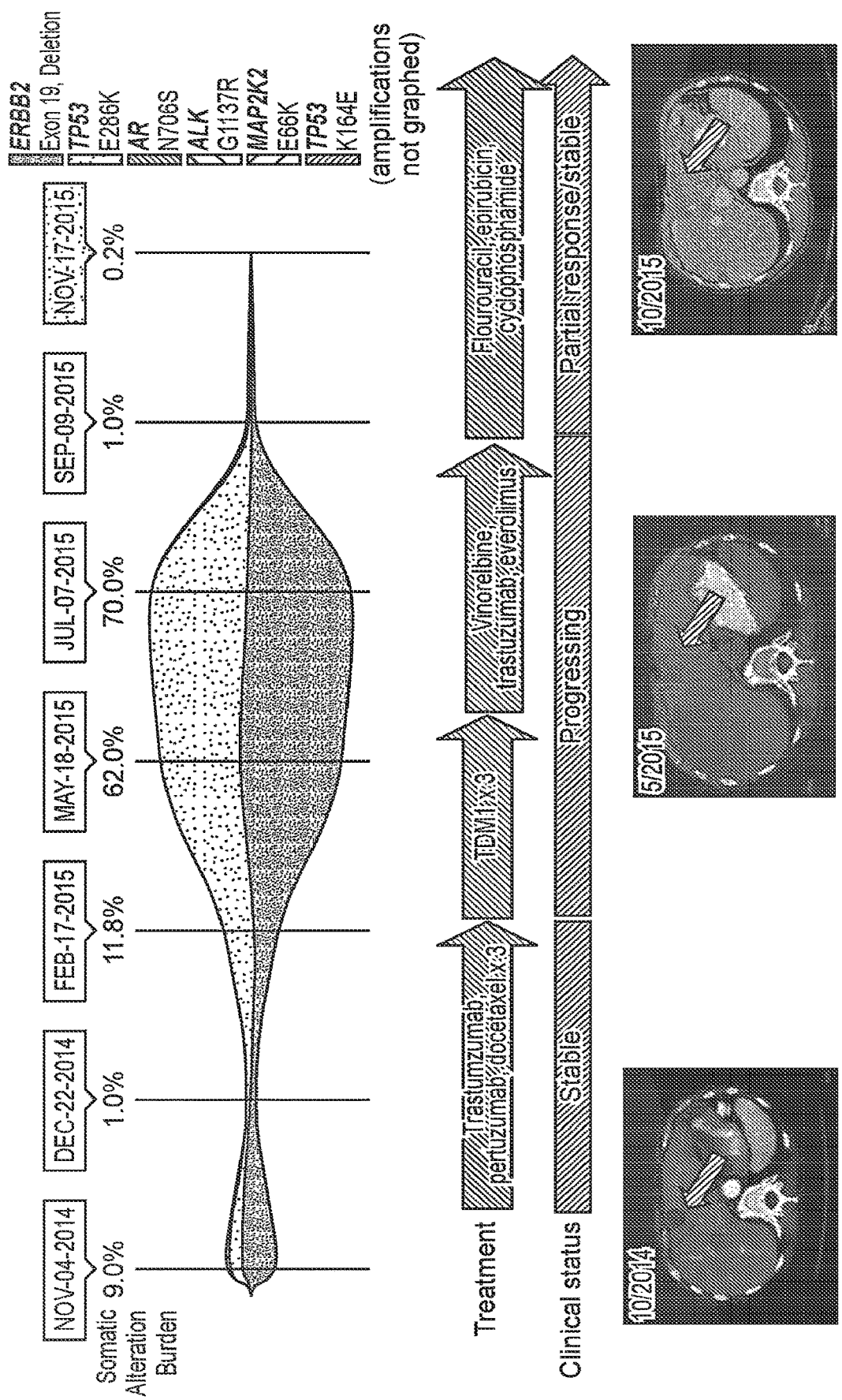
FIG. 19 describes an embodiment wherein genetic variations in circulating tumor DNA were monitored upon detection and through treatment of cancer.

Serial ctDNA testing was performed at the time of initial metastatic diagnosis and at each progression with a 70-gene ctDNA NGS panel (see Table 5) that includes all NCCN-recommended somatic genomic variants for solid tumors and sequences complete exons of 70 genes to report single nucleotide variants (SNVs), fusions, amplifications, and indels with high sensitivity (85% in stage III/IV solid tumors) and ultra-high specificity (>99.9999%). CT scans of the chest and abdomen were performed and correlated with ctDNA levels (FIG. 19).

The patient's initial blood draw detected the ERBB2 exon 19 indel p.Leu755_Glu757delinsSer with a mutant allele fraction of 9.0%. CT scan of the liver from October 2014 demonstrated moderate tumor burden in the liver. Based on identifying the mutation in the ctDNA, a treatment was identified to be administered to the subject to treat the breast cancer, and the treatment was administered to the subject to treat the breast cancer. After an initial molecular response to combined trastuzumab, pertuzumab and docetaxel, molecular evidence of tumor progression was present on the February 2015 ctDNA assay. The patient's tumor continued to progress clinically in the liver, as demonstrated by the CT scan from May 2015. ctDNA analysis in September 2015 showed drastic reduction in ctDNA levels, with all mutations dropping ≤1.0% mutant allele fraction. This molecular response correlated with marked reduction of disease in the liver as shown on the October 2015 CT scan. One or more mutations in the ctDNA from the subject may be identified with a sensitivity of at least 80%. One or more mutations in the ctDNA from the subject may be identified with a specificity of at least 99%, at least 99.9%, at least 99.99%, at least 99.999%, or at least 99.9999%.

In another case, a patient was initially diagnosed with ER/PR positive invasive breast cancer at age 44 and was treated with surgery, followed by hormonal therapy after a local recurrence. At age 61, she was found to have axillary adenopathy and liver metastases. Treatment details and the patient's clinical status following the diagnosis of MBC are shown in FIG. 19.

Analysis of ctDNA in this metastatic breast cancer patient identified an in-frame activating ERBB2 insertion/deletion in exon 19, analogous to EGFR activating mutations in lung adenocarcinoma. There was a molecular response to anti-HER2 therapy initially with the ERBB2 indel dropping from 9.0% to 1.0% mutant allele fraction. It is presumed that emerging clones acquired resistance mechanisms besides the ERBB2 indel, and drove progression.

Serial monitoring of ctDNA reflected clinical and radiographic progression and response to subsequent lines of chemotherapy. Knowing the specific ERBB2 variant is important, as specific ERBB2 variants may drive sensitivity or resistance to differing anti-HER2 monoclonal antibody or dual anti-EGFR/ERBB2 tyrosine kinase inhibitor therapies. In conclusion, NCCN guidelines should include recommendations for ctDNA NGS for treatment-refractory MBC patients to identify actionable ERBB2 mutations as is recommended for metastatic non-small cell lung cancer.

5. Example 6

Assaying ctDNA Utilizing a High-Sensitivity Panel Detects ERBB2 Mutations (e.g., Indels) in Lung Cancer and Guides Therapy Selection Genotyping of metastatic non-small cell lung cancer (NSCLC) has become standard of care, targeting the canonical driver mutations in seven genes: EGFR, BRAF, MET and fusions in ALK, RET, and ROS 1 and "HER2 [ERBB2 gene] mutations". Unlike the EGFR gene where mutation and amplification co-occur 80% of the time, ERBB2 indels and single nucleotide variants (SNVs) are generally mutually exclusive from ERBB2 gene amplification and suggest different treatments.

ERBB2 in-frame indels between codons 775 and 881 in exon 19 and 20 of the ERBB2 gene, of which a 12 base pair exon 20 YVMA insertion is the most common, are activating mutations in 2% of NSCLC, especially lung adenocarcinoma (LUAD). Targeted next generation sequencing (NGS) of cell-free circulating tumor DNA (ctDNA) provides a non-invasive means of identifying these potential ERBB2 driver mutations, especially when tissue biopsies are quantity not sufficient (QNS) for analysis or are undergenotyped.

A single ERBB2 exon 19 deletion p.Arg756 Glu757delinsLys at 3.9% mutant allele fraction (MAF) was noted in one patient, for whom outcome data was available. Initial tissue was immunohistochemistry (IHC) negative for HER2 overexpression at the referring hospital where the archival tissue biopsy was exhausted and thus could not be sequenced. Based on the cfDNA finding of an ERBB2 indel, the patient was switched from cytotoxic chemotherapy to trastuzumab with objective response on PET/CT and a repeat Guardant360™ showed the ERBB2 indel MAF had dropped below the test limit of detection. After four months the patient's tumor progressed and the ERBB2 indel MAF rose to 0.4%. It was decided to switch to ado-emtansine trastuzumab (T-DM1).

Guardant360™ is a targeted cfDNA NGS panel using hybrid capture and complete exon sequencing for single nucleotide variant detection in 70 genes, copy number amplifications (CNA) in 16 genes, fusions in six genes, and small indels in EGFR, ERBB2 and MET exon 14 skipping (see FIG. 20).

Indels are detected down to 0.04% mutant allele fraction with ultra-high specificity (>99.998%). CNAs are detected at 99.8% specificity down to 2.2 copies. De-identified pathology and genotyping reports were reviewed for consecutive NSCLC patients in whom ERBB2 indels and gene amplifications were identified in clinical practice.

5,684 consecutive samples from 5,211 unique patients with advanced NSCLC or lung adenocarcinoma were genotyped. 57 unique patients were found with ERBB2 indels (1.09%) and 8 (14.04%) of these were also ERBB2 amplified (see Table 1). 9 patients had pathology reports with tissue-based NGS results, 7 confirming the ERBB2 indel (78% PPV). The two discordant tissue NGS samples were 10 and 21 months older than the plasma-based test. Known function SNVs are shown in FIG. 2: codons 143 and 340 (not shown) were also recurrently mutated; ERBB2 SNVs occurred at 0.5% frequency. One or more ERBB2 indels in the ctDNA from the subject may be identified with a sensitivity of at least 80%. One or more ERBB2 indels in the ctDNA from the subject may be identified with a specificity of at least 99%, at least 99.9%, at least 99.99%, at least 99.999%, or at least 99.9999%.

Conclusions: 1) ERBB2 indels were found at a lower frequency (1.1% vs. 2%) than reported in the literature, perhaps reflecting that some of the NSCLC patients were not LUAD. 2) ERBB2 indels were not exclusive of ERBB2 amplification, perhaps reflecting this clinical cohort where >80% of patients have progressed on treatment and where copy number amplification may be a mechanism of treatment resistance. 3) ERBB2 indels, SNVs, and CNAs can be identified without tissue biopsy in NSCLC patients in this large series of over 5,000 patients. 4) In a patient whose tissue was not available for sequencing, an objective response with trastuzumab was obtained for an ERBB2 exon 19 indel.

While embodiments of the present disclosure have been shown and described herein, it will be obvious to those skilled in the art that such embodiments are provided by way of example only. It is not intended that the disclosure be limited by the specific examples provided within the specification. While the disclosure has been described with reference to the aforementioned specification, the descriptions and illustrations of the embodiments herein are not meant to be construed in a limiting sense. Numerous variations, changes, and substitutions will now occur to those skilled in the art without departing from the disclosure. Furthermore, it shall be understood that all aspects of the disclosure are not limited to the specific depictions, configurations or relative proportions set forth herein which depend upon a variety of conditions and variables. It should be understood that various alternatives to the embodiments of the disclosure described herein may be employed in practicing the disclosure. It is therefore contemplated that the disclosure shall also cover any such alternatives, modifications, variations or equivalents. It is intended that the following claims define the scope of the disclosure and that methods and structures within the scope of these claims and their equivalents be covered thereby.

What is claimed is:

1. A method for preparing and sequencing nucleic acids, the method comprising:
   a) providing a sample of cell-free deoxyribonucleic acid (cfDNA) molecules from a subject;
   b) attaching adapters to a plurality of the cfDNA molecules by ligation to produce adapted nucleic acids;
   c) amplifying a plurality of the adapted nucleic acids by polymerase chain reaction (PCR)-based amplification to provide amplified nucleic acids;
   d) enriching the amplified nucleic acids for a panel of genomic regions, wherein the panel comprises one or more genomic regions from each of at most 20 genes, wherein the at most 20 genes comprises one or more genes selected from AKT1, ALK, APC, ATM, BRAF, CTNNB1, EGFR, ERBB2, ESR1, FGFR2, GATA3, GNAS, IDH1, IDH2, KIT, KRAS, MET, NRAS, PDGFRA, PIK3CA, PTEN, RB1, SMAD4, STK11, and TP53; and
   e) sequencing the enriched set of amplified nucleic acids to generate sequence reads, wherein the sequencing is performed at a sequence read depth of at least 50,000 sequence reads per base, and wherein the sequencing is performed within a read budget that allocates a pre-determined total number of base reads, wherein the enriched set of amplified nucleic acids comprises no more than a pre-determined amount of DNA.

2. The method of claim 1, wherein the adapters comprise molecular barcodes having predetermined sequences.

3. The method of claim 1, wherein the cancer is selected from the group consisting of ovarian cancer, pancreatic cancer, breast cancer, colorectal cancer, and non-small cell lung carcinoma.

4. The method of claim 3, wherein the cancer is non-small cell lung carcinoma (NSCLC), and the non-small cell lung carcinoma is squamous cell carcinoma or adenocarcinoma.

5. The method of claim 1, wherein the cfDNA molecules are derived from blood, serum or plasma.

6. The method of claim 1, wherein the subject has previously received treatment for a cancer.

7. The method of claim 3, wherein the subject has received surgical treatment, radiation treatment, chemotherapy, targeted cancer therapeutics or a cancer immunotherapy.

8. The method of claim 1, wherein the enriching is performed by sequence capture using oligonucleotide probes that hybridize to the sequences in the panel of genomic regions.

9. The method of claim 8, wherein the oligonucleotide probes are 60 to 120 bases long.

10. The method of claim 1, wherein sequencing is performed at a read depth of at least 100,000 reads per base.

11. The method of claim 1, further comprising comparing sequence information from the cfDNA molecules to sequence information obtained from a cohort of healthy individuals, a cohort of cancer patients, or germline DNA from the subject.

12. The method of claim 1, wherein the panel comprises at least one exon from each of the genes.

13. The method of claim 1, wherein multiple samples comprising cfDNA are collected from the subject over a plurality of time points and enriched and sequenced.

14. The method of claim 1, wherein the sample comprises 10 to 300 nanograms (ng) of cfDNA molecules.

15. The method of claim 1, wherein the enriching is performed using amplification-based enrichment.

16. The method of claim 1, wherein the panel of genomic regions is selected using information derived from a cancer tumor biopsy of the subject indicating at least one of the genomic regions contain a tumor marker present in a greater proportion in the cancer tumor biopsy than a background population.

17. The method of claim 1, wherein the panel comprises 10 to 20 different genes.

* * * * *